United States Patent
Zech et al.

(10) Patent No.: US 9,834,521 B2
(45) Date of Patent: Dec. 5, 2017

(54) CHOLINE KINASE INHIBITORS

(71) Applicant: ARIAD Pharmaceuticals, Inc., Cambridge, MA (US)

(72) Inventors: Stephan G. Zech, Boston, MA (US); Anna Kohlmann, Winchester, MA (US); Feng Li, Winchester, MA (US); Yihan Wang, Newton, MA (US); Tianjun Zhou, Belmont, MA (US); David C. Dalgarno, Brookline, MA (US); William C. Shakespeare, Southborough, MA (US); Xiaotian Zhu, Newton, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/774,359

(22) PCT Filed: Mar. 13, 2014

(86) PCT No.: PCT/US2014/026404
§ 371 (c)(1),
(2) Date: Sep. 10, 2015

(87) PCT Pub. No.: WO2015/151761
PCT Pub. Date: Sep. 25, 2014

(65) Prior Publication Data
US 2016/0024024 A1 Jan. 28, 2016

Related U.S. Application Data

(60) Provisional application No. 61/800,428, filed on Mar. 15, 2013.

(51) Int. Cl.
| | | |
|---|---|---|
| *C07D 243/08* | (2006.01) | |
| *A61K 31/551* | (2006.01) | |
| *C07D 401/10* | (2006.01) | |
| *C07D 403/10* | (2006.01) | |
| *C07D 417/10* | (2006.01) | |
| *C07D 245/02* | (2006.01) | |
| *C07D 401/14* | (2006.01) | |
| *C07D 403/14* | (2006.01) | |
| *C07D 413/10* | (2006.01) | |
| *C07D 413/14* | (2006.01) | |
| *C07F 9/645* | (2006.01) | |

(52) U.S. Cl.
CPC .......... *C07D 243/08* (2013.01); *A61K 31/551* (2013.01); *C07D 245/02* (2013.01); *C07D 401/10* (2013.01); *C07D 401/14* (2013.01); *C07D 403/10* (2013.01); *C07D 403/14* (2013.01); *C07D 413/10* (2013.01); *C07D 413/14* (2013.01); *C07D 417/10* (2013.01); *C07F 9/645* (2013.01)

(58) Field of Classification Search
CPC .. C07D 243/08; C07D 401/10; C07D 403/10; A61K 31/551
USPC .......................................... 540/575; 514/218
See application file for complete search history.

(56) References Cited

U.S. PATENT DOCUMENTS

| | | | |
|---|---|---|---|
| 2003/0166690 A1* | 9/2003 | Ebdrup | ................. C07C 39/367 514/354 |
| 2009/0124596 A1* | 5/2009 | Bonnert | ............... C07D 213/80 514/211.15 |

FOREIGN PATENT DOCUMENTS

| | | | |
|---|---|---|---|
| WO | WO 00/39110 | * | 7/2000 |
| WO | WO 2007/053452 A1 | | 5/2007 |
| WO | WO 2008/037459 A1 | | 4/2008 |
| WO | WO 2012/125598 A1 | | 9/2012 |

OTHER PUBLICATIONS

Al-Saffar, Nada M.S., et al., Noninvasive Magnetic Resonance Spectroscopic Pharmacodynamic Markers of the Choline Kinase Inhibitor MN58b in Human Carcinoma Models, *Cancer Research*, 2006; 66(1), 427-434.

Al-Saffar, Nada M.S., et al., the Phosphoinositide 3-Kinase Inhibitor PI-103 Downregulates Choline Kinase a Leading to Phosphocholine and Total Choline Decrease Detected by Magnetic Resonance Spectroscopy, *Cancer Research*, 2011, 70(13), 5507-5517.

Brenner, Eric et al., Nickel-Catalysed Couplings of Aryl Chlorides with Secondary Amines and Piperazines, *Tetrahedron*, 1999, 55, 12829-12842.

Choubey, Vinay, et al., Inhibition of *Plasmodium falciparum* Choline Kinase by Hexadecyltrimethylammonium Bromide: a Possible Antimalarial Mechanism, *Antimicrobial Agents and Chemotherapy*, 2007, 51(2), 696-706.

Chua, Boon Tin, et al., Regulation of Akt(ser473) Phosphorylation by Choline Kinase in Breast Carcinoma Cells, *Molecular Cancer*, 2009, 8:131, DOI: 10.1186/1476-4598-8-131, 12 pages.

(Continued)

*Primary Examiner* — Deepak Rao
(74) *Attorney, Agent, or Firm* — Fangli Chen; Proskauer Rose LLP

(57) ABSTRACT

This invention relates to compounds of the general formula (I): in which the variable groups are as identified herein, and to preparation and use of the compounds.

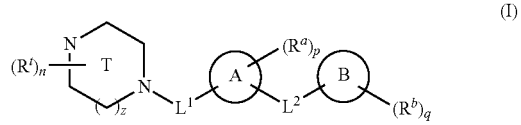

1 Claim, No Drawings

(56) References Cited

OTHER PUBLICATIONS

Database Registry No. 1317333-71-3, [1,1'-biphenyl]-2-carbonitrile, 4'-[[4(1,1-dimethylethyl)hexahydro-1H-1,4-diazepin-1-yl]methyl]-, entered STN: Aug. 14, 2011, 1 page.
Extended European Search Report dated Jul. 13, 2016, for EP Appl. 14770715.2, 10 pages.
Gallego-Ortega, David, et al., Differential Role of Human Choline Kinase α and β Enzymes in Lipid Metabolism: Implications in Cancer Onset and Treatment, *PLoS One*, 2009, 4(11), e7819, doi:10.1371/journal.pone.0007819, 11 pages.
Glunde, Kristine, et al., RNA Interference-Mediated Choline Kinase Suppression in Breast Cancer Cells Induces Differentiation and Reduces Proliferation, *Cancer Res*, 2005, 65(23), 11034-11043.
Glunde, Kristine, et al., Hypoxia Regulates Choline Kinase Expression through Hypoxia-Inducible Factor-1α Signaling in a Human Prostate Cancer Model, *Cancer Res*, 2008, 68(1), 172-180.
Hernandez-Alcoceba, Ruben, et al., Choline Kinase Inhibitors as a Novel Approach for Antiproliferative Drug Design, *Oncogene*, 1997, 15, 2289-2301.
Hernandez-Alcoceba, Ruben, et al., In Vivo Antitumor Activity of Choline Kinase Inhibitors: A Novel Target for Anticancer Drug Discovery, *Cancer Research*, 1999, 59, 3112-3118.
Hernando, E., et al., A Critical Role for Choline Kinase-α in the Aggressiveness of Bladder Carcinomas, *Oncogene*, 2009, 28, 2425-2435.
Hollestelle, Antoinette, et al., Phosphatidylinositol-3-OH Kinase or RAS Pathway Mutations in Human Breast Cancer Cell Lines, *Mol Cancer Res*, 2007, 5(2), 195-201.
Hong, Bum Soo, et al., Crystal Structures of Human Choline Kinase Isoforms in Complex with Hemicholinium-3, *The Journal of Biological Chemistry*, 2010, 285(21), 16330-16340.
International Search Report and Written Opinion of the International Searching Authority for PCT/US14/26404, dated Jul. 10, 2014, 11 pages.
Krishnamachary, Balaji, et al., Noninvasive Detection of Lentiviral-Mediated Choline Kinase Targeting in a Human Breast Cancer Xenograft, *Cancer Research*, 2009; 69(8), 3464-3471.
Mahoney, CL, et al., LKBI/KRAS Mutant Lung Cancers Constitute a Genetic Subset of NSCLC with Increased Sensitivity to MAPK and mTOR Signaling Inhibition, *British Journal of Cancer*, 2009, 100, 370-375.
Malito, Enrico, et al., Elucidation of Human Choline Kinase Crystal Structures in Complex with the Products ADP or Phosphocholine, *J. Mol. Biol.*, 2006, 364, 136-151.
Moestue, Siver A., et al., Distinct Choline Metabolic Profiles are Associated with Differences in Gene Expression for Basal-like and Luminal-like Breast Cancer Xenograft Models, *BMC Cancer*, 2010, 10:433, DOI: 10.1186/1471-2407-10-433, 12 pages.
Morish, F., et al., c-Myc Activates Multiple Metabolic Networks to Generate Substrates for Cell-Cycle Entry, *Oncogene*, 2009, 28, 2485-2491.
Nimmagadda, Sridhar, et al., Pharmacodynamic Markers for Choline Kinase Down-regulation in Breast Cancer Cells, *NEOPLASIA*, 2009, 11(5), 477-484.
Peisach, Daniel, et al., The Crystal Structure of Choline Kinase Reveals a Eukaryotic Protein Kinase Fold, *Structure*, 2003, 11, 703-713.
PubChem CID 67007161, SureCN1366240, 4-[3-[-(4-Methylpiperazin-1-yl)methyl]phenyl]benzoic acid, Record created Nov. 30, 2012, 3 pages.
PubChem CID 11348943, SureCN3983257, 4-[[4-[3-(Trifluoromethyl)phenyl]phenyl]methyl]-1,4-diazabicyclo[3.2.2]nonane, Record created Oct. 26, 2006, 3 pages.
PubChem CID 57849589, SureCN4476884, 1-[[4-[2-(Trifluoromethyl)phenyl]phenyl]methyl]piperazine, Record created Aug. 19, 2012, 4 pages.
PubChem CID 24857429, SureCN4790876, 4-[4-[(4-Methylpiperazin-1-yl)methyl]phenyl]-1H-pyrrolo[2,3-b]pyridine, Record created Jul. 28, 2008, 4 pages.
PubChem CID 69677724, SureCN6132979, 4-[4-(4-Cyclohexylpiperazin-1-yl)phenyl]benzoic acid;dihydrochloride, Record created Dec. 1, 2012, 3 pages.
PubChem CID 11617720, SureCN6404942, 1-Methyl-4-[7-[4-(trifluoromethyl)phenyl]-1,2,3,4-tetrahydronaphthalen-1-yl]piperazine, Record created Oct. 26, 2006, 3 pages.
PubChem CID 57665782, SureCN8260488, [4-[4-(Piperazine-1-carbonyl)phenyl]phenyl]-piperazin-1-ylmethanone, Record created Aug. 19, 2012, 5 pages.
PubChem CID 58080890, SureCN10135889, 6-(1,4-diazepan-1-ylmethyl)-5-phenylisoquinoline, Record created Aug. 19, 2012, 5 pages.
PubChem CID 413862, SureCN10724841, [4-(4-Methylpiperazine-1-carbonyl)phenyl]-(4-methylpiperazin-1-yl)methanone, Record created Mar. 26, 2005, 5 pages.
PubChem CID 70888319, SureCN13359565, Piperazin-1-yl-[4-[4-(piperazin-1-ylmethyl)phenyl]phenyl]methanone, Record created Mar. 21, 2013, 3 pages.
PubChem CID 57531137, SureCN13940629, 1-Ethyl-4-[[4-[3-(trifluoromethyl)phenyl]phenyl]methyl]-1,4-diazepane, Record created Aug. 18, 2012, 4 pages.
Ramirez De Molina, Ana, et al., Overexpression of Choline Kinase is a Frequent Feature in Human Tumor-Derived Cell Lines and in Lung, Prostate, and Colorectal Human Cancers, *Biochemical and Biophysical Research Communication*, 2002, 296, 580-583.
Ramirez De Molina, Ana, et al., Regulation of Choline Kinase Activity by Ras Proteins Involves Ral-GDS and PI3K, *Oncogene*, 2002, 21, 937-946.
Ramirez De Molina, Ana, et al., Choline Kinase is a Novel Oncogene that Potentiates RhoA-Induced Carcinogenesis, *Cancer Research*, 2005, 65(13), 5647-5653.
Ramirez De Molina, Ana et al., Choline Kinase as a Link Connecting Phospholipid Metabolism and Cell Cycle Regulations: Implications in Cancer Therapy, *The International Journal of Biochemistry & Cell Biology*, 2008, 40, 1753-1763.
Ramirez De Molina, Ana et al., Preclinical Development of Tcd-717, a Second Generation of Choline Kinase Inhibitors, as a New Anticancer-Agent, Oral Presentation from Outstanding Abstracts, 7th *Annual Cancer Drugs Research and Development Conferences* (San Diego, CA, Jan. 28-29, 2010), 1 page.
Ratnam, Shobha, et al., Early Increase in Choline Kinase Activity upon Induction of the H-ras Oncogene in Mouse Fibroblast Cell Lines, *Archives of Biochemistry and Biophysics*, 1995, 323(2), 313-322.
Raubenheimer, Peter J., et al., A Choline-Deficient Diet Exacerbates Fatty Liver but Attenuates Insulin Resistance and Glucose Intolerance in Mice Fed a High-Fat Diet, *Diabetes*, 2006, 55, 2015-2020.
Rodriguez-Gonzalez, Agustin, et al., Inhibition of Choline Kinase as a Specific Cytotoxic Strategy in Oncogene-Transformed Cells, *Oncogene*, 2003, 22, 8803-8812.
Rodriguez-Gonzalez, Agustin, et al., Choline Kinase Inhibition Induces the Increase in Ceramides Resulting in a Highly Specific and Selective Cytotoxic Antitumoral Strategy as a Potential Mechanism of Action, *Oncogene*, 2004, 23, 8247-8259.
Squillace R., et al., Small molecule inhibitors of choline kinase lead to reduced phosphocholine levels and induction of apoptosis in breast cancer cells, *Proceedings of the 103rd Annual Meeting of the American Association for Cancer Research* (Chicago, IL, Mar. 31-Apr. 4, 2012); *Cancer Res* 2012;72(8 Suppl):Abstract nr 3236 (Apr. 15, 2012), 1 page.
Vassar, Victor, et al., One-step Method of Phosphatidylcholine Extraction and Separation, *BioTechniques*, 2007, 42:442-444.
Wecker, Lynn et al., Adenosine Inhibits Choline Kinase Activity and Decreases the Phosphorylation of Choline in Striatal Synaptosomes, *Journal of Neurochemistry*, 1988, 50(6), 1945-1951.
Yalcin, A., et al., Selective Inhibition of Choline Kinase Simultaneously Attenuates MAPK and PI3K/AKT Signaling, *Oncogene*, 2009, 1-11.
Yalcin, A., et al., Selective Inhibition of Choline Kinase Simultaneously Attenuates MAPK and PI3K/AKT Signaling, *Oncogene*, 2010, 29, 139-149.

(56) References Cited

OTHER PUBLICATIONS

Yuan, Chong et al., Identification of Critical Residues of Choline Kinase A2 from *Caenorhabditis elegans*, *The Journal of Biological Chemistry*, 2004, 279(17), 17801-17809.

Zech, Stephan, G., et al., Novel Small Molecule Inhibitors of Choline Kinase Identified by Fragment-Based Drug Discovery, *Journal of Medicinal Chemistry*, 2016, 59, 671-686.

Zhuang, Z.-P., et al., Radioiodinated Styrylbenzenes and Thioflavins as Probes for Amyloid Aggregates, *Journal of Medicinal Chemistry*, 2001, 44, 1905-1914.

Belén Rubio Ruíz et al., "Design, synthesis, theoretical calculations and biological evaluation of new non-symmetrical choline kinase inhibitors", European Journal of Medicinal Chemistry, vol. 50, pp. 154-162, 2012.

Rubén N. Hernández-Alcoceba, et al., "Choline kinase inhibitors as a novel approach for antiproliferative drug design", Oncogene, vol. 15, pp. 2289-2301, 1997.

\* cited by examiner

CHOLINE KINASE INHIBITORS

CROSS-REFERENCE TO RELATED APPLICATIONS

This application claims priority under 35 U.S.C. §371 to International Application No. PCT/US2014/026404, filed Mar. 13, 2014, which claims priority to 35 U.S.C. §119(e) to U.S. Provisional Application Ser. No. 61/800,428 filed Mar. 15, 2013 which is hereby incorporated herein by reference in its entirety.

FIELD

The present disclosure relates to compounds having choline kinase modulatory activity, processes for the preparation of such compounds, compositions and methods of using such compounds.

BACKGROUND

Choline Kinase (ChoK) catalyzes the synthesis of phosphocholine (pCh) as the first step in the metabolic pathway towards synthesis of the major membrane phospholipid, phosphatidylcholine.

The choline kinase family is encoded by two separate genes, CHKα and CHKβ, resulting in three different proteins with variable choline/ethanolamine kinase (ChoK/EtnK) activity, namely, ChoKα1, ChoKα2 and ChoKβ1. Both ChoKα1 and ChoKα2 preferentially phosphorylate choline over ethanolamine, compared to ChoKβ.

ChoKα1 is a 457 amino acid polypeptide provided in the NCBI database under accession number NP 001268 (release of Jun. 17, 2012). The polypeptide is encoded by a 2733 base-pair (bp) transcript formed by alternative splicing from the ChoKα gene. The cDNA sequence of the transcript encoding ChoKα1 is provided in the NCBI database with accession number NM_001277 (release of Jun. 17, 2012).

ChoKα2 is a 439 amino acid polypeptide provided in the NCBI database under accession number NP 997634 (release of Jun. 17, 2012). The polypeptide is encoded by a 2679 bp transcript formed by alternative splicing from the ChoKα gene. The cDNA sequence of the transcript encoding ChoKα2 is provided in the NCBI database with accession number M_M 212469 (release of Jun. 17, 2012).

Abnormal choline metabolism is characteristic of oncogenesis and cancer progression in an array of cancer types. Exogenous expression of ChoKα1, but not ChoKβ1, is capable of driving tumor formation in non-transformed cells (Gallego-Ortega et al., *PLoS One,* 2009). It is known that increased phosphorylation of choline is a hallmark of certain malignant phenotypes. ChoK over-expression, (primarily ChoKα1), has been associated with certain human cancers, including breast, liver, lung, colorectal, ovary and prostate (Glunde et al. *Nat Rev Can,* 2011). For example, ChoKα, phosphocholine and total choline were increased in breast carcinomas compared with normal breast tissue, and this increase correlated with advanced tumor grade (Ramirez de Molina et al., *Oncogene,* 2002; Gribbestad et al., *Anticancer Res,* 1999). This finding suggests that any tumor type that displays elevated pCho or ChoK itself would be a candidate for ChoK inhibitor therapy.

In addition to tumor type, there is preclinical evidence that inhibition of ChoK expression in cell lines results in disruption of MAPK and AKT activity and decreased cell proliferation (Yalcin, et al. *Oncogene,* 2009; Clem et al. *Oncogene,* 2011). It has also been found that cell lines expressing activated RAS exhibit sensitivity to ChoK knockdown by siRNA or small molecule inhibition (Ramirez de Molina et al. *Biochem Biophys Res Commun,* 2001). These studies indicate that tumors demonstrating aberrant MAPK, AKT or RAS signaling may be used as a general target for ChoK anticancer drug design.

These observations have motivated efforts to develop anti-cancer agents targeting ChoK.

SUMMARY OF THE INVENTION

In various aspects and embodiments, the present invention comprises new ChoK modulating compounds and use of these compounds in treating certain cancers and other diseases.

In further aspects and embodiments, the present invention comprises the preparation of a compound of any of Formulas I through XLVIII or of any other of the compounds of this invention shown as Examples 1-160 herein.

In further aspects and embodiments, the present invention encompasses a composition comprising a compound of the invention or a salt, hydrate or other solvate thereof, including a compound of any of the described classes or subclasses, including those of any of the formulas discussed below, in association with at least one pharmaceutically acceptable carrier, adjuvant or diluent. Such compositions can be administered to a subject in need thereof to inhibit the growth, development and/or metastasis of cancers, including solid tumors (e.g., breast, colon, pancreatic, CNS and head and neck cancers, among others) and various forms of leukemia, including leukemias and other cancers which are resistant to other treatment, including those which are resistant to treatment, and generally for the treatment and prophylaxis of diseases or undesirable conditions.

In further aspects and embodiments, the compounds of the present invention are also useful in the manufacture of a medicament to attenuate or prevent disorders through inhibition of ChoK.

In various embodiments, the present invention comprises a method for treating cancer in a subject in need thereof, which comprises administering to the subject a treatment effective amount of a composition containing a compound of this invention. Various cancers which may be thus treated are noted elsewhere herein and include, among others, cancers which are or have become resistant to another anticancer agent or one of the other agents noted herein.

In various embodiments, the cancer treatment method of the present invention involves administering a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by choline kinase inhibited by one of the disclosed compounds or a pharmaceutically acceptable derivative thereof.

In various embodiments, compounds of the present invention are used as standards and reagents for characterizing various kinases, especially, but not limited to, choline kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

DETAILED DESCRIPTION OF THE INVENTION

1. General Description of Compounds of the Invention

In one aspect, the present disclosure provides compounds of Formula (I),

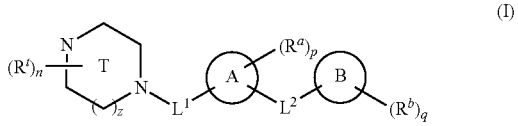

a tautomer, an individual isomer, a mixture of isomers or a pharmaceutically acceptable salt, solvate or hydrate thereof, wherein:

Ring T is optionally substituted on a C or N ring atom with $R^t$; (i) wherein $R^t$ is substituted on any two adjacent ring atoms, and, taken together with said ring atoms to which they are attached, form a 5-6 membered cycloalkyl, cycloalkenyl or heterocyclyl fused ring, (ii) wherein $R^t$ is substituted on any two non-adjacent ring atoms, and, taken together with the ring atoms to which they are attached, form a 1-3 carbon bridge, or (iii) wherein $R^t$ is substituted on a common ring atom, and, taken together with that ring atom to which it is attached, forms a 5-6 membered cycloalkyl, cycloalkenyl or hetrocyclyl spirocyclic ring; and wherein said Ring T or said ring formed by any adjacent or non-adjacent $R^t$ substituents is further optionally substituted with 1-4 $R^d$ groups;

$R^t$ is alkylenyl, alkenylenyl, heteroalkylenyl, or heteroalkenylenyl;

$R^d$ is alkyl, alkenyl or cycloalkyl;

$L^1$ is $(CH_2)_x$, $(CH_2)_xO(CH_2)_x$ or $(CH_2)_xNR^1(CH_2)_x$, wherein $L^1$ is present in either direction;

Ring A is a 5-6 membered aryl or heteroaryl ring containing 1-2 nitrogen ring atoms, with the remaining ring atoms being carbon, optionally substituted on any ring atom with $R^a$, wherein $R^a$, when substituted on any two adjacent ring atoms, and, taken together with said ring atoms to which they are attached, form a 5-6 membered cycloalkyl, heterocyclyl, aryl, or heteroaryl fused ring, wherein said heterocyclyl or heteroaryl fused ring contains 1-3 heteroatoms selected from O, N, and S and wherein said Ring A or the ring formed by adjacent $R^a$ substituents is further optionally substituted with 1-4 $R^e$ groups;

$R^a$ is alkylenyl, alkenylenyl, heteroalkylenyl, or heteroalkenylenyl;

$R^e$ is independently alkyl, alkenyl, alkynyl, cycloalkyl, heterocyclyl, aryl, heteroaryl, carbonyl, cyano, halo, nitro, oxo, —$OR^1$, -alkyl-C(O)—$R^1$, —C(O)—$R^1$, —$CO_2R^1$, —C(O)$NR^1R^2$, —$NR^1R^2$, —$SO_2R^1$, —$SO_2NR^1R^2$, —$NHSO_2R^1$;

$L^2$ is $(CH_2)_x$, $(CH_2)_xC(O)(CH_2)_x$, or $(CH_2)_xNR^1(CH_2)_x$, wherein $L^2$ is present in either direction;

Ring B is aryl, heterocyclyl, or heteroaryl, optionally substituted on any ring atom with $R^b$;

$R^b$ is independently selected from alkyl, cyano, halo, nitro, $R^1$, $R^2$, $OR^1$, —C(O)$NR^1R^2$, —C($R^1$)=$NR^2$, -alkyl-C(O)$NR^1R^2$, alkyl-$R^1$, $R^1$-alkyl-$R^2$, —$NR^1R^2$, -alkyl-$NR^1R^2$, —$SO_2R^1$, —$SO_2NR^1R^2$, —$NHSO_2R^1$, —C(O)—$R^1$, or $CO_2R^1$;

$R^1$ and $R^2$ are independently selected from H, alkyl, alkenyl, alkynyl, amino, amido, acetamido, acetyl, alkylaminocarbonyl, alkoxy, formyl, hydroxyl, cycloalkyl, heterocyclyl, aryl, heteroaryl, cyano, monoalkylamino, monocyclopropylamino, dialkylamino, dialkylphosphoryl, hydrazinyl, or acetyl hydrazinyl; or $R^1$ and $R^2$, taken together with the atom(s) to which they are attached, form a 5- or 6-membered cycloalkyl, heterocyclyl, aryl, or heteroaryl ring, wherein said heterocyclyl or heteroaryl ring contains 1-3 heteroatoms selected from O, N, and $S(O)_r$; or $R^1$ and $R^2$ when substituted on any two adjacent ring atoms of Ring B, and, taken together with the atoms to which they are attached, form a 5- or 6-membered cycloalkyl, heterocyclyl, aryl, or heteroaryl fused ring, wherein said heterocyclyl or heteroaryl fused ring contains at least one of (i) 1-3 O and S atoms; or (ii) 2-3 N atoms;

each of the alkyl, alkenyl, alkynyl, cycloalkyl, heterocyclyl, aryl and heteroaryl moieties is unsubstituted or substituted with one or more groups selected from amino, alkylamino, dialkylamino, aminocarbonyl, halo, acetyl, alkyl, alkenyl, alkynyl, cyanoalkyl, cycloalkyl, heterocyclyl, aryl, heteroaryl, alkylaminocarbonyl, dialkylaminocarbonyl, alkylaminocarbonyloxy, dialkylaminocarbonyloxy, alkylsulfonyl, alkylsulfonamido, nitro, cyano, carboxy, alkoxycarbonyl, alkylcarbonyl, hydroxy, hydroxyalkyl, alkoxy, alkoxyalkyl, acyloxy, haloalkoxy, =O, =S, NH, $NNR^1R^2$, $NNHC(O)R^1$, $NNHCO_2R^1$, $NNHSO_2R^1$, —YP(=O)($YR^1$)($YR^2$) wherein Y is independently a bond, —O—, —S— or —$NR^1$; and each of the cycloalkyl, heterocyclyl, aryl, heteroaryl moieties is unsubstituted or substituted with one or more groups selected from amino, alkylamino, dialkylamino, aminocarbonyl, halo, alkyl, alkenyl, alkynyl, aryl, heteroaryl, cycloalkyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

n is independently 0 to 2;
p is independently 0 to 2;
q is independently 0 to 5;
r is independently 0 to 2;
x is independently 0 to 5; and
z is independently 1 to 2;

with the proviso that where Ring B is substituted $R^b$, and $R^b$ is selected from $R^1$ and $R^2$ which are substituted on any two adjacent ring atoms of Ring B, and, taken together with the atoms to which they are attached, form a 5- or 6-membered cycloalkyl, heterocyclyl, aryl, or heteroaryl fused ring, said fused ring contains no further $R^b$ substituents; with the proviso that where both z=1 and Ring B is pyrazole, q=0; and with the proviso that where both $L^2$=—$(CH_2)_x$— and x=0, then either p or q is not equal to 0.

In certain embodiments, the present disclosure provides compounds of Formula (I),

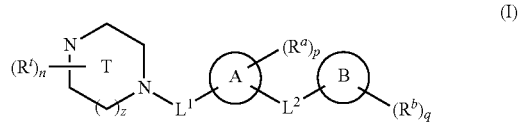

a tautomer, an individual isomer, a mixture of isomers or a pharmaceutically acceptable salt, solvate or hydrate thereof, wherein:

Ring T is optionally substituted on a C or N ring atom with $R^t$; (i) wherein $R^t$ is substituted on any two adjacent ring atoms, and, taken together with said ring atoms to which they are attached, form a 5-6 membered cycloalkyl, cycloalkenyl or heterocyclyl fused ring, (ii) wherein $R^t$ is substituted on any two non-adjacent ring atoms, and, taken together with the ring atoms to which they are attached, form a 1-3 carbon bridge, or (iii) wherein $R^t$ is substituted on a common ring atom, and, taken together with that ring atom to which it is attached, forms a 5-6 membered cycloalkyl, cycloalkenyl or hetrocyclyl spirocyclic ring; and wherein said Ring T or said ring formed by any adjacent or non-adjacent $R^t$ substituents is further optionally substituted with 1-4 $R^d$ groups;

$R^t$ is alkylenyl, alkenylenyl, heteroalkylenyl, or heteroalkenylenyl;

$R^d$ is alkyl, alkenyl or cycloalkyl;

$L^1$ is $(CH_2)_x$, $(CH_2)_xO(CH_2)_x$ or $(CH_2)_xNR^1(CH_2)_x$, wherein $L^1$ is present in either direction;

Ring A is a 5-6 membered aryl or heteroaryl ring containing 1-2 nitrogen ring atoms, with the remaining ring atoms being carbon, optionally substituted on any ring atom with $R^a$, wherein $R^a$, when substituted on any two adjacent ring atoms, and, taken together with said ring atoms to which they are attached, form a 5-6 membered cycloalkyl, heterocyclyl, aryl, or heteroaryl fused ring, wherein said heterocyclyl or heteroaryl fused ring contains 1-3 heteroatoms selected from O, N, and S and wherein said Ring A or the ring formed by adjacent $R^a$ substituents is further optionally substituted with 1-4 $R^e$ groups;

$R^a$ is alkylenyl, alkenylenyl, heteroalkylenyl, or heteroalkenylenyl;

$R^e$ is independently alkyl, alkenyl, alkynyl, cycloalkyl, heterocyclyl, aryl, heteroaryl, carbonyl, cyano, halo, nitro, oxo, —$OR^1$, -alkyl-C(O)—$R^1$, —C(O)—$R^1$, —$CO_2R^1$, —C(O)$NR^1R^2$, —$NR^1R^2$, —$SO_2R^1$, —$SO_2NR^1R^2$, —$NHSO_2R^1$;

$L^2$ is $(CH_2)_x$, $(CH_2)_xC(O)(CH_2)_x$, or $(CH_2)_xNR^1(CH_2)$, wherein $L^2$ is present in either direction;

Ring B is aryl, heterocyclyl, or heteroaryl, optionally substituted on any ring atom with $R^b$;

$R^b$ is independently selected from alkyl, cyano, halo, nitro, $R^1$, $R^2$, $OR^1$, —C(O)$NR^1R^2$, —C($R^1$)=$NR^2$, -alkyl-C(O)$NR^1R^2$, alkyl-$R^1$, $R^1$-alkyl-$R^2$, —$NR^1R^2$, -alkyl-$NR^1R^2$, —$SO_2R^1$, —$SO_2NR^1R^2$, —$NHSO_2R^1$, —C(O)—$R^1$, or $CO_2R^1$;

$R^1$ and $R^2$ are independently selected from H, alkyl, alkenyl, alkynyl, amino, amido, acetamido, acetyl, alkylaminocarbonyl, alkoxy, formyl, hydroxyl, cycloalkyl, heterocyclyl, aryl, heteroaryl, cyano, monoalkylamino, monocyclopropylamino, dialkylamino, dialkylphosphoryl, hydrazinyl, or acetyl hydrazinyl; or $R^1$ and $R^2$, taken together with the atom(s) to which they are attached, form a 5- or 6-membered cycloalkyl, heterocyclyl, aryl, or heteroaryl ring, wherein said heterocyclyl or heteroaryl ring contains 1-3 heteroatoms selected from O, N, and S(O)$_r$; or $R^1$ and $R^2$ when substituted on any two adjacent ring atoms of Ring B, and, taken together with the atoms to which they are attached, form a 5- or 6-membered cycloalkyl, heterocyclyl, aryl, or heteroaryl fused ring, wherein said heterocyclyl or heteroaryl fused ring contains at least one of (i) 1-3 O and S atoms; or (ii) 2-3 N atoms; each of the alkyl, alkenyl, alkynyl, cycloalkyl, heterocyclyl, aryl and heteroaryl moieties is unsubstituted or substituted with one or more groups selected from amino, alkylamino, dialkylamino, aminocarbonyl, halo, acetyl, alkyl, alkenyl, alkynyl, cyanoalkyl, cycloalkyl, heterocyclyl, aryl, heteroaryl, alkylaminocarbonyl, dialkylaminocarbonyl, alkylaminocarbonyloxy, dialkylaminocarbonyloxy, alkylsulfonyl, alkylsulfonamido, nitro, cyano, carboxy, alkoxycarbonyl, alkylcarbonyl, hydroxy, hydroxyalkyl, alkoxy, alkoxyalkyl, acyloxy, haloalkoxy, =O, =S, NH, $NNR^1R^2$, $NNHC(O)R^1$, $NNHCO_2R^1$, and $NNHSO_2R^1$; and each of the cycloalkyl, heterocyclyl, aryl, heteroaryl moieties is unsubstituted or substituted with one or more groups selected from amino, alkylamino, dialkylamino, aminocarbonyl, halo, alkyl, alkenyl, alkynyl, aryl, heteroaryl, cycloalkyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

n is independently 0 to 2;
p is independently 0 to 2;
q is independently 0 to 5;
r is independently 0 to 2;
x is independently 0 to 5; and
z is independently 1 to 2;

with the proviso that where Ring B is substituted $R^b$, and $R^b$ is selected from $R^1$ and $R^2$ which are substituted on any two adjacent ring atoms of Ring B, and, taken together with the atoms to which they are attached, form a 5- or 6-membered cycloalkyl, heterocyclyl, aryl, or heteroaryl fused ring, said fused ring contains no further $R^b$ substituents; with the proviso that where both z=1 and Ring B is pyrazole, q=0; and with the proviso that where both $L^2$=—$(CH_2)_x$— and x=0, then either p or q is not equal to 0.

The foregoing definitions are further elaborated upon and exemplified below and apply to all subsequent occurrences except to the extent otherwise specified.

2. Featured Classes of Compounds and Uses Generally

In various compounds, Ring T is a piperazinyl ring when z is 1, or a homopiperazinyl ring when z is 2. A nitrogen atom in Ring T is connected to Ring A with a linker designated $L^1$ and discussed below. The remaining nitrogen atom in Ring T is either unsubstituted (having hydrogen) or substituted with some substituent other than hydrogen, as discussed below.

Ring T is optionally substituted on any carbon or nitrogen ring atoms with at least two $R^t$ substituents, selected from alkylenyl, alkenylenyl, heteroalkylenyl or heteroalkenylenyl radicals, which combine to form various ring structures attached to Ring T. For example, when two $R^t$ groups are substituted on any two adjacent ring atoms of Ring T, the $R^t$ groups, along with the adjacent Ring T atoms to which they are attached, combine to form a 5-6 membered cycloalkyl, cycloalkenyl or heterocyclyl fused ring onto Ring T. In various embodiments, two alkylenyl $R^t$ groups are substituted on non-adjacent Ring T atoms, and the $R^t$ groups, along with the non-adjacent ring atoms to which they are attached, form a 1-3 carbon bridge across Ring T. Examples of such fused ring and carbon bridged bicyclic systems include, but are not limited to:

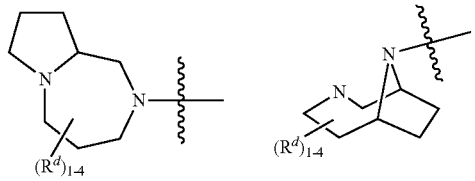

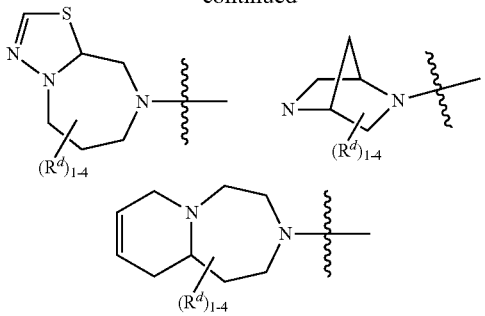

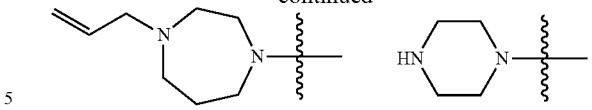

In various embodiments, one or more $R^t$ groups may be substituted on a common Ring T atom. In this case, the $R^t$ groups, taken together with the one atom to which they are attached, form a 5-6 membered cycloalkyl, cycloalkenyl or heterocyclyl spirocyclic ring with Ring T. Examples of spirocyclic systems resulting from the use of $R^t$ groups on a common Ring T atom include, but are not limited to:

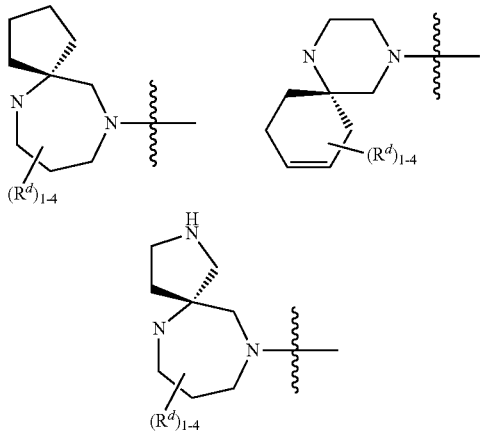

In various embodiments, Ring T, or the fused, bicyclic or spirocyclic ring system resulting from the modification of Ring T with various $R^t$ groups, is optionally substituted with 1-4 $R^d$ groups as indicated in the above ring system examples. In the case of fused, bicyclic and spirocyclic ring systems resulting from the operation of $R^t$ groups with Ring T, the optional 1-4 $R^d$ groups may be dispersed on the original 6-7 membered Ring T, on any ring formed from $R^t$ groups, or on both the original Ring T and any $R^t$ formed rings. That is, the optional 1-4 $R^t$ groups may be distributed anywhere around the fused, bicyclic or spirocyclic ring structure.

The optional 1-4 $R^d$ groups are selected from alkyl, alkenyl and cycloalkyl groups. If there are no $R^d$ groups, then any remaining unsubstituted nitrogen or carbon ring atoms are assumed bonded to hydrogen in order to fill the valence. The following non-limiting examples show an unmodified Ring T system (i.e., no $R^t$ group substitution) with and without various $R^d$ groups:

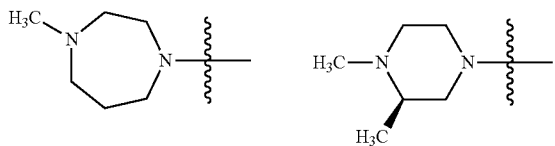

In various embodiments, the optional 1-4 $R^d$ groups are selected from alkyl, alkenyl and cycloalkyl groups, and each of the alkyl, alkenyl and cycloalkyl moieties may be unsubstituted or substituted with one or more groups selected from amino, alkylamino, dialkylamino, aminocarbonyl, halo, acetyl, alkyl, alkenyl, alkynyl, cyanoalkyl, cycloalkyl, heterocyclyl, aryl, heteroaryl, alkylaminocarbonyl, dialkylaminocarbonyl, alkylaminocarbonyloxy, dialkylaminocarbonyloxy, alkylsulfonyl, alkylsulfonamido, nitro, cyano, carboxy, alkoxycarbonyl, alkylcarbonyl, hydroxy, hydroxyalkyl, alkoxy, alkoxyalkyl, acyloxy, haloalkoxy, =O, =S, NH, $NNR^1R^2$, $NNHC(O)R^1$, $NNHCO_2R^1$, and $NNHSO_2R^1$, wherein each of the cycloalkyl, heterocyclyl, aryl, heteroaryl moieties recited above is unsubstituted or substituted with one or more groups selected from amino, alkylamino, dialkylamino, aminocarbonyl, halo, alkyl, alkenyl, alkynyl, aryl, heteroaryl, cycloalkyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy. In this way, the optional 1-4 $R^d$ groups on Ring T or the fused, bicyclic or spirocyclic ring systems derived from Ring T after operation of $R^t$ groups, take on functional complexity beyond bare alkyl, alkenyl and cycloalkyl options.

In various compounds, Ring T is 4-methylhomopiperazin-1-yl (i.e., where z is 2, n is 0, $R^d$ is $CH_3$, and $R^d$ is bonded to the 4-nitrogen atom of Ring T). In other embodiments, Ring T is 4-methylpiperazin-1-yl (i.e., where z is 1, n is 0, with no further $R^d$ substitution on Ring T other than $CH_3$ on the 4-nitrogen atom).

In various compounds, Ring T is linked to Ring A via the linker moiety designated $L^1$. $L^1$ is selected from $(CH_2)_x$, $(CH_2)_xO(CH_2)_x$ or $(CH_2)_xNR^1(CH_2)_x$, wherein $L^1$ is present in either direction. As used herein, any x in the $L^1$ linker is chosen independently to produce symmetrical or unsymmetrical linkages. For example, $(CH_2)_xNR^1(CH_2)_x$ may denote the linkage —$(CH_2)_2NH$—, where one x value is 2 and the other is zero. "Either direction" means that for an unsymmetrical linkage such as —$(CH_2)_2NH$—, the linkage can be arranged in either direction between Ring T and Ring A. That is, the N of Ring T may be covalently bonded to the carbon of the linkage —$(CH_2)_2NH$— and Ring A bonded to the N of the linker, or alternatively, the N of Ring T may be covalently bonded to the N of the linker —$(CH_2)_2NH$— and Ring A bonded to the carbon chain of the linker.

In various embodiments, $L^1$ is a covalent bond, where $L^1$ is $(CH_2)_x$ and x is zero.

In various embodiments, $L^1$ is an ether, where $L^1$ is $(CH_2)_x$—O—$(CH_2)_x$ and x is zero for each instance of x.

In various embodiments, Ring A is a 5-6 membered aryl or heteroaryl ring containing 1-2 nitrogen ring atoms. Thus, Ring A may include, for example, imidazolyl, phenyl, pyrazinyl, pyrazolyl, pyridazinyl, pyridinyl, pyrimidinyl or pyrrolyl. Since Ring A is attached to Ring T through linker $L^1$, and also attached to Ring B through linker $L^2$, there are already two positions of Ring A occupied by these bonds, as indicated in the examples of Ring A shown below:

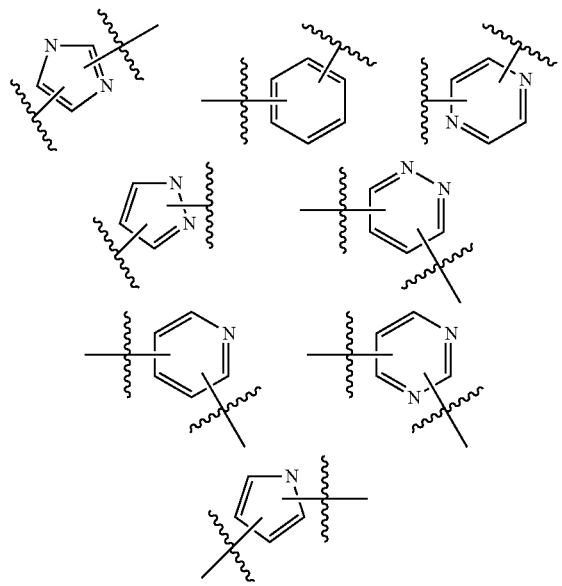

In various embodiments, Ring A is optionally substituted on any two adjacent ring atoms with $R^a$, where $R^a$ is selected from alkylenyl, alkenylenyl, heteroalkylenyl, or heteroalkenylenyl radicals, which together with the ring atoms to which they are attached, form a 5-6 membered cycloalkyl, heterocyclyl, aryl, or heteroaryl fused ring onto Ring A, wherein the resulting heterocyclyl or heteroaryl fused ring contains 1-3 heteroatoms selected in any combination from O, N, and S atoms.

Thus, when $R^a$ substitution on adjacent Ring A atoms operates to cyclize a 5-6 membered cycloalkyl, heterocyclyl, aryl, or heteroaryl ring onto Ring A, a fused ring system results, producing, for example, indene, 2,3-dihydro-1H-indenyl, indolyl, isoindolyl, benzpyrazolyl, benzimidazolyl, 1H-pyrrolo[2,3b]pyridinyl, 1H-pyrrolo[2,3c]pyridinyl, 1H-pyrrolo[3,2c]pyridinyl, 1H-pyrrolo[3,2b]pyridinyl, naphthalenyl, quinolinyl, isoquinolinyl, phthalazinyl, quinazolinyl, quinoxalinyl, 2,6-naphthyridinyl, 2,7-naphthyridinyl, 1,5-naphthyridinyl, 1,6-naphthyridinyl, 1,7-naphthyridinyl, or 1,8-naphthyridinyl from Ring A. Since Ring A is attached to Ring T through linker $L^1$, and also attached to Ring B through linker $L^2$, there are already two positions of a fused ring system resulting from Ring A occupied by these bonds, as indicated in the examples of fused ring systems from Ring A shown below:

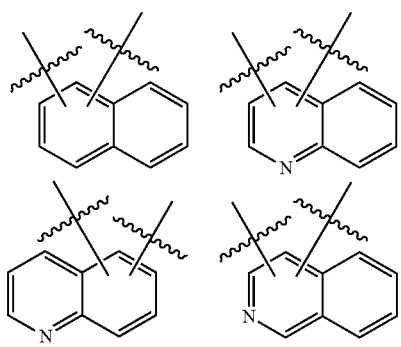

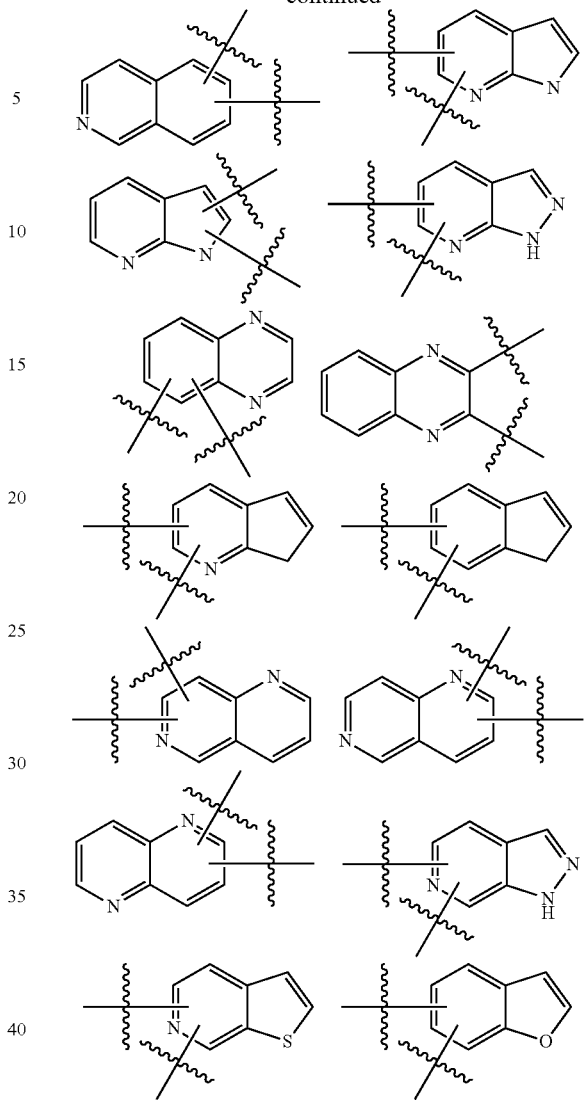

When no $R^a$ substitution operates to modify Ring A, Ring A remains a 5-6 membered aryl or heteroaryl ring containing 1-2 nitrogen ring atoms, such as for example, phenyl, pyrazinyl, pyrazolyl, pyridazinyl, pyridinyl, pyrimidinyl or pyrrolyl.

In various embodiments, Ring A, or the fused ring system resulting from the modification of Ring A with various $R^a$ groups, is optionally substituted with 1-4 $R^e$ groups. In the case of fused ring systems, the $R^e$ may be substituted on original Ring A, on any ring formed from $R^a$ groups, or on both original Ring A and any $R^a$ formed rings; i.e. anywhere on the fused ring structure.

In various embodiments, Ring B is aryl, heterocyclyl, or heteroaryl.

In various embodiments, Ring B is phenyl.

In various embodiments, Ring B may comprise 2-furanyl, 3-furanyl, 1-imidazolyl, 2-imidazolyl, 4-imidazolyl, 5-imidazolyl, 1-imidazolidinyl, 2-imidazolidinyl, 4-imidazolidinyl, 3-isothiazolyl, 4-isothiazolyl, 5-isothiazolyl, 3-isoxazolyl, 4-isoxazolyl, 5-isoxazolyl, 2-isoxazolidinyl, 3-isoxazolidinyl, 4-isoxazolidinyl, 5-isoxazolidinyl, 2-morpholinyl, 3-morpholinyl, 4-morpholinyl, 2-oxazolyl, 4-oxazolyl, 5-oxazolyl, phenyl, 1-piperadinyl, 2-piperadinyl, 3-piperadinyl, 4-piperadinyl, 1-piperazinyl, 2-piperazinyl, 1-pyrazolidinyl, 3-pyrazolidinyl, 4-pyrazolidinyl, 1-pyrazolyl, 3-pyrazolyl, 4-pyrazolyl, 2-pyridinyl, 3-pyridinyl, 4-pyridinyl, 2-pyrimidinyl, 4-pyrimidinyl, 5-pyrimidinyl, 1-pyrrolidinyl, 2-pyrrolidinyl, 3-pyrrolidinyl, 1-(2-pyrrolidonyl), 3-(2-pyrrolidonyl), 4-(2-pyrrolidonyl), 5-(2-pyrrolidonyl), 1-pyrrolyl, 2-pyrrolyl, 3-pyrrolyl, 2-(2,3,4,5-tetrahydropyridinyl), 3-(2,3,4,5-tetrahydropyridinyl), 4-(2,3,4,5-tetrahydropyridinyl), 5-(2,3,4,5-tetrahydropyridinyl), 6-(2,3,4,5-tetrahydropyridinyl), 1-(1,2,3,4-tetrahydropyridinyl), 2-(1,2,3,4-tetrahydropyridinyl), 3-(1,2,3,4-tetrahydropyridinyl), 4-(1,2,3,4-tetrahydropyridinyl), 5-(1,2,3,4-tetrahydropyridinyl), 6-(1,2,3,4-tetrahydropyridinyl), 1-(1,2,3,6-tetrahydropyridinyl), 2-(1,2,3,6-tetrahydropyridinyl), 3-(1,2,3,6-tetrahydropyridinyl), 4-(1,2,3,6-tetrahydropyridinyl), 5-(1,2,3,6-tetrahydropyridinyl), 6-(1,2,3,6-tetrahydropyridinyl), 2-thiazolyl, 4-thiazolyl, 5-thiazolyl, 2-thiazolidinyl, 3-thiazolidinyl, 4-thiazolidinyl, 5-thiazolidinyl, 2-thiomorpholinyl, 3-thiomorpholinyl, 4-thiomorpholinyl, 2-(thiomorpholinyl-1,1-dione), 3-(thiomorpholinyl-1,1-dione), 4-(thiomorpholinyl-1,1-dione), 1-(1,2,4-triazolyl), 3-(1,2,4-triazolyl), 4-(1,2,4-triazolyl), 1-(1,2,3-triazolyl), 2-(1,2,3-triazolyl), or 4-(1,2,3-triazolyl).

Ring B is optionally substituted on any two adjacent ring atoms with $R^b$ groups, $R^{b1}$ and $R^{b2}$. In the case where $R^{b1}$ is $R^1$ and $R^{b2}$ is $R^2$, $R^1$ and $R^2$, along with the two Ring B atoms to which they are attached, may form a 5 or 6-membered cycloalkyl, heterocyclyl, aryl or heteroaryl ring, wherein the heterocyclyl or heteroaryl ring contains at least one of: (i) 1-3 O and S atoms; or (ii) 2-3 N atoms. In this way, a fused ring system may be formed from Ring B with adjacent $R^b$ substituents. If adjacent $R^{b1}$ and $R^{b2}$ groups are selected in this way, then it is implied that $R^1$ and $R^2$ are independently selected from alkylenyl, alkenylenyl, heteroalkylenyl, or heteroalkenylenyl radicals such that a 5 or 6-membered cycloalkyl, heterocyclyl, aryl or heteroaryl ring can be fused onto Ring B to produce a fused ring system.

In various embodiments, when $R^b$ substitution on adjacent Ring B atoms operates to cyclize a 5 or 6-membered cycloalkyl, heterocyclyl, aryl or heteroaryl ring onto Ring B, wherein the heterocycyl or heteroaryl ring contains at least one of: (i) 1-3 O and S atoms; or (ii) 2-3 N atoms, the resulting fused ring system may include, for example, naphthalenyl.

In various embodiments, when $R^b$ substitution on adjacent Ring B atoms operates to cyclize a 5 or 6-membered cycloalkyl, heterocyclyl, aryl or heteroaryl ring onto Ring B, wherein the heterocycyl or heteroaryl ring contains at least one of: (i) 1-3 O and S atoms; or (ii) 2-3 N atoms, the resulting fused ring system may include, for example, benzotriazolyl, indazolyl, indenyl, 2,3-dihydro-1H-indenyl, benzopyrazolyl, benzimidazolyl, 1H-pyrrolo[2,3b]pyridinyl, 1H-pyrrolo[2,3c]pyridinyl, 1H-pyrrolo[3,2c]pyridinyl, 1H-pyrrolo[3,2b]pyridinyl, quinolinyl, isoquinolinyl, phthalazinyl, quinazolinyl, quinoxalinyl, 2,6-naphthyridinyl, 2,7-naphthyridinyl, 1,5-naphthyridinyl, 1,6-naphthyridinyl, 1,7-naphthyridinyl, and 1,8-naphthyridinyl.

Where a heterocycyl or heteroaryl ring resulting from $R^b$ substitution is a 5 or 6-membered cycloalkyl, heterocyclyl, aryl or heteroaryl ring, such ring contains at least one of: (i) 1-3 O and S atoms; or (ii) 2-3 N atoms, which eliminates the possibility for $R^b$ substitution to form a 4-, 5-, 6- or 7-indolyl, or the 4-, 5-, 6-, or 7-isoindolyl fused ring system from Ring B. However, when Ring B is a pyrrole ring, $R^b$ substitution may operate to fuse an aryl ring onto Ring B to arrive at 1-, 2-, or 3-indolyl or 1-, 2-, or 3-isoindolyl ring structures from Ring B. Additionally, when Ring B is a pyrrolidine ring, $R^b$ substitution may operate to fuse an aryl ring onto Ring B to arrive at 1-, 2-, or 3-indolinyl or 1-, 2-, or 3-isoindolinyl ring structures from Ring B.

In various embodiments, any one or more $R^b$ groups on Ring B may be selected from alkyl, cyano, halo, nitro, $R^1$, $R^2$, $OR^1$, —$C(O)NR^1R^2$, —$C(R^1)$=$NR^2$, -alkyl-C(O)NR$^1$R$^2$, alkyl-R$^1$, R$^1$-alkyl-R$^2$, —NR$^1$R$^2$, -alkyl-NR$^1$R$^2$, —SO$_2$R$^1$, —SO$_2$NR$^1$R$^2$, —NHSO$_2$R$^1$, —C(O)—R$^1$, or CO$_2$R$^1$, wherein: $R^1$ and $R^2$ are independently selected from H, alkyl, alkenyl, alkynyl, amino, amido, acetamido, acetyl, alkylaminocarbonyl, alkoxy, formyl, hydroxyl, cycloalkyl, heterocyclyl, aryl, heteroaryl, cyano, monoalkylamino, monocyclopropylamino, dialkylamino, dialkylphosphoryl, hydrazinyl, or acetyl hydrazinyl; or $R^1$ and $R^2$, taken together with the atom(s) to which they are attached, form a 5- or 6-membered cycloalkyl, heterocyclyl, aryl, or heteroaryl ring, wherein said heterocyclyl or heteroaryl ring contains 1-3 heteroatoms selected from O, N, and $S(O)_r$; and wherein each of the alkyl, alkenyl, alkynyl, cycloalkyl, heterocyclyl, aryl and heteroaryl moieties is unsubstituted or substituted with one or more groups selected from amino, alkylamino, dialkylamino, aminocarbonyl, halo, acetyl, alkyl, alkenyl, alkynyl, cyanoalkyl, cycloalkyl, heterocyclyl, aryl, heteroaryl, alkylaminocarbonyl, dialkylaminocarbonyl, alkylaminocarbonyloxy, dialkylaminocarbonyloxy, alkylsulfonyl, alkylsulfonamido, nitro, cyano, carboxy, alkoxycarbonyl, alkylcarbonyl, hydroxy, hydroxyalkyl, alkoxy, alkoxyalkyl, acyloxy, haloalkoxy, =O, =S, NH, NNR$^1$R$^2$, NNHC(O)R$^1$, NNHCO$_2$R$^1$, and NNHSO$_2$R$^1$; and each of the cycloalkyl, heterocyclyl, aryl, heteroaryl moieties is unsubstituted or substituted with one or more groups selected from amino, alkylamino, dialkylamino, aminocarbonyl, halo, alkyl, alkenyl, alkynyl, aryl, heteroaryl, cycloalkyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy.

With the above mentioned options for $R^b$ noted, in various embodiments $R^b$ is —C(O)NR$^1$R$^2$ (i.e., an amide bonded to Ring B). In various embodiments, $R^1$, $R^2$ along with the N atom to which they are attached, form a heterocyclic ring and the heterocyclic ring is further optionally substituted as described herein. For example, in various embodiments, —C(O)NR$^1$R$^2$ may be selected from 4-methyl-1,4-diazepan-1-carbonyl and 4-methylpiperazin-1-carbonyl.

In various embodiments, $R^b$ is -alkyl-NR$^1$R$^2$. In the case where -alkyl- is —(CH$_2$)—, $R^b$ may be —CH$_2$—NR$^1$R$^2$. Of the many possibilities for this disubstitued aminomethyl substituent, one example is where $R^1$, $R^2$ and the N atom to which they are attached form a heterocyclic ring, and the heterocyclic ring is optionally substituted with a methyl group. Therefore, in various embodiments, —CH$_2$—NR$^1$R$^2$ may be selected from (4-methyl-1,4-diazepan-1-yl)methyl or (4-methylpiperazin-1-yl)methyl.

In various embodiments, $R^b$ is $R^1$ and $R^1$ is "aryl." Therefore $R^b$ may be, for example, phenyl, with phenyl optionally substituted as described above.

In various embodiments, $R^b$ may be selected from:

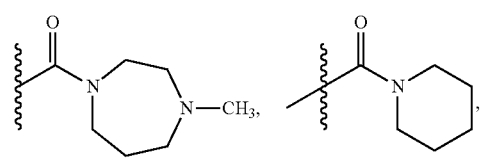

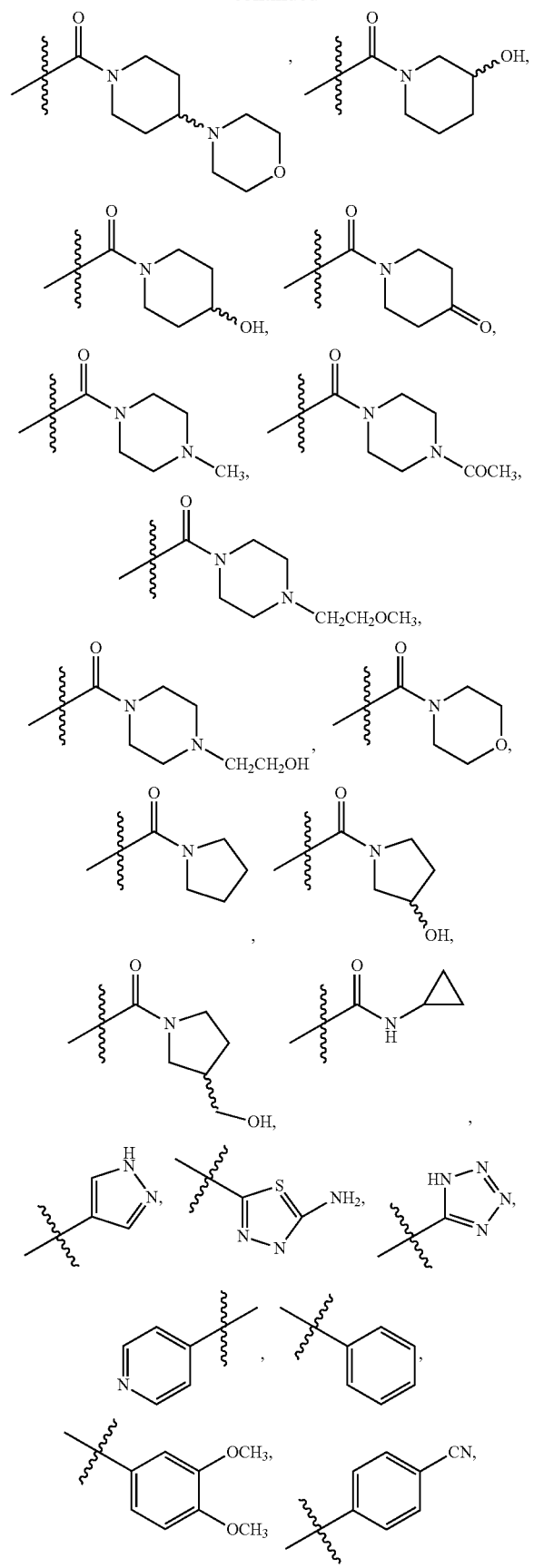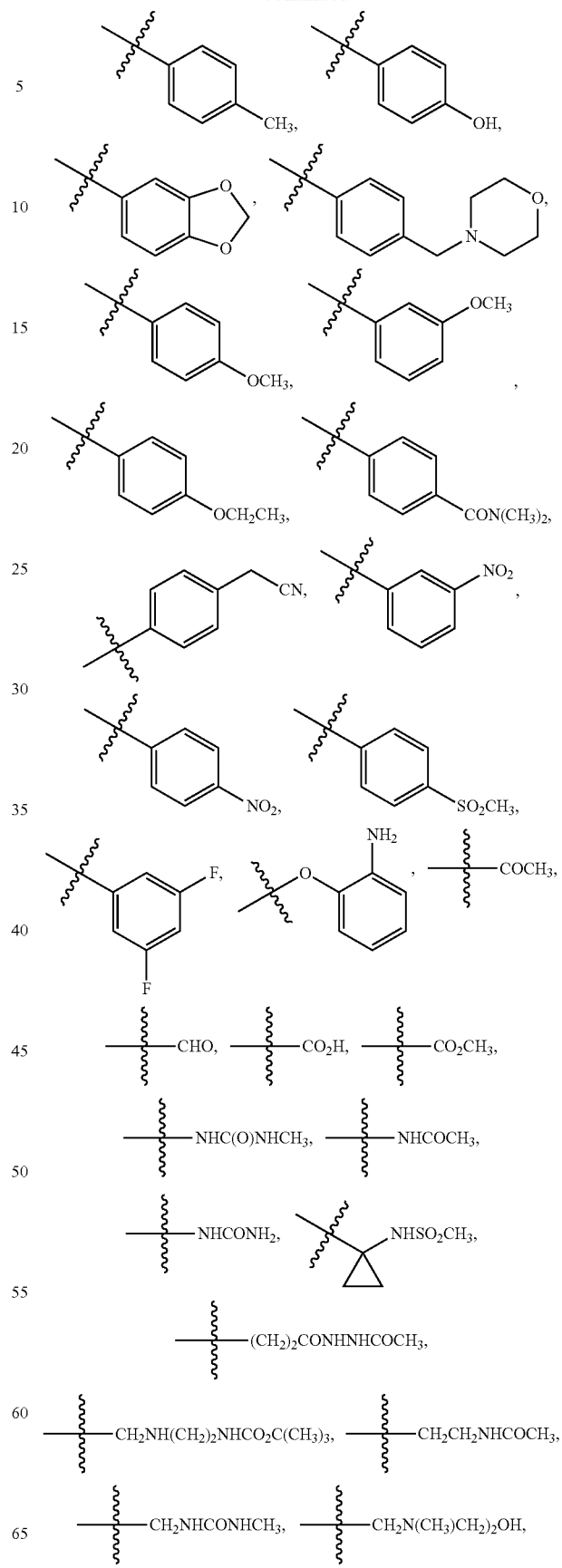

-continued
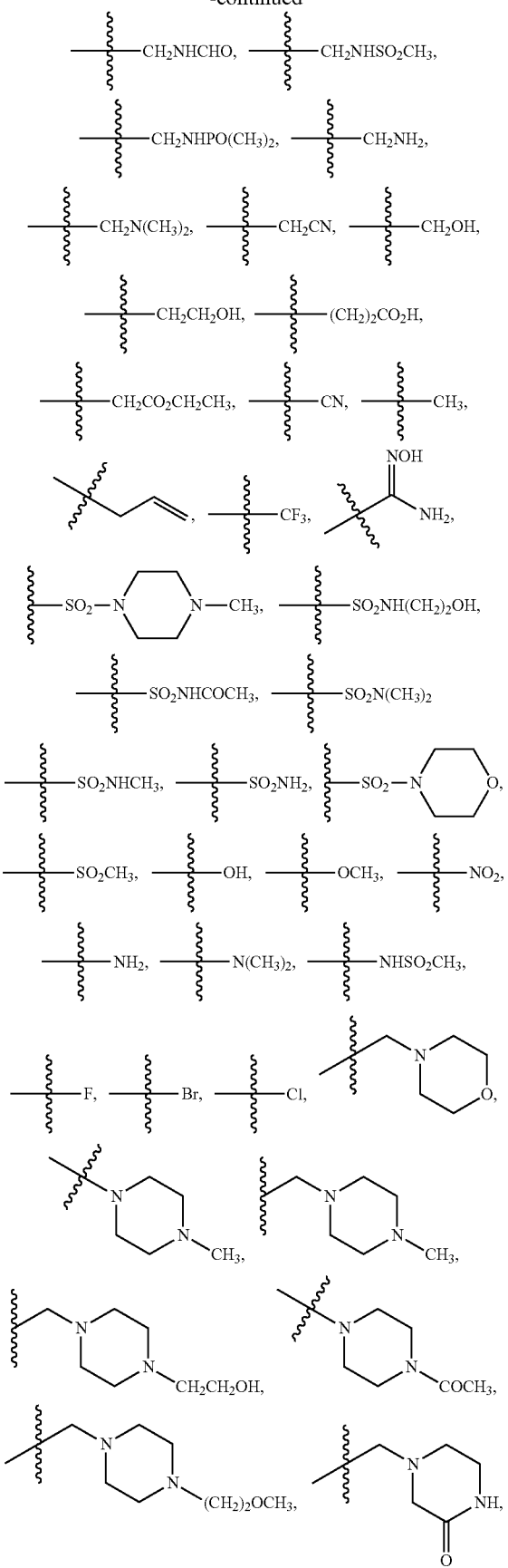
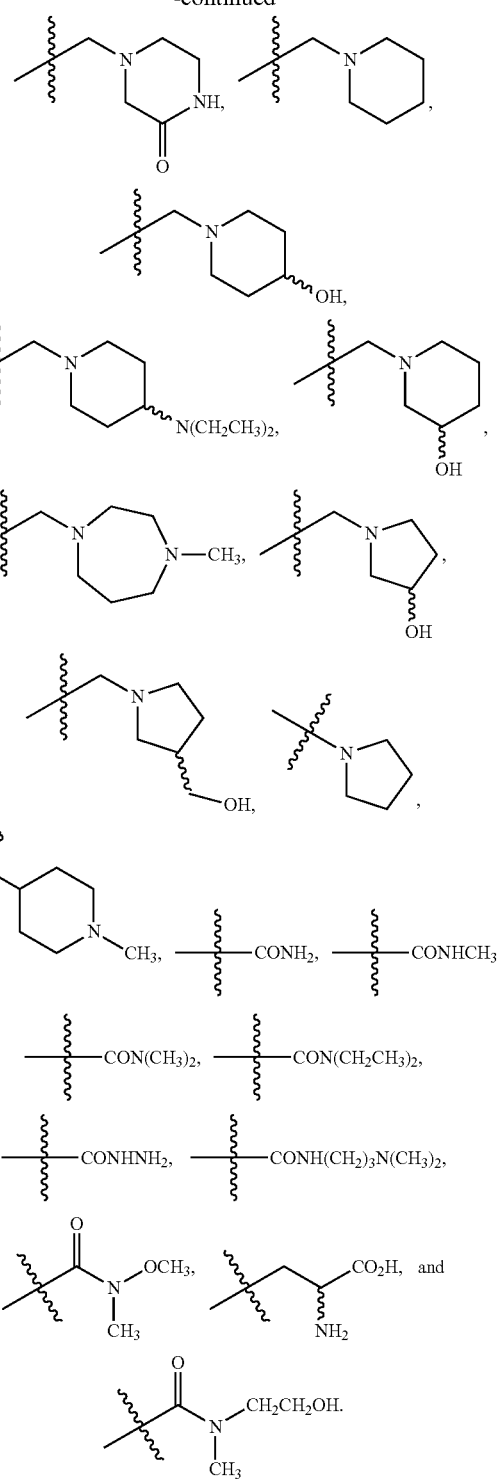
In various embodiments, any one or more $R^b$ groups may comprise the following general structure:
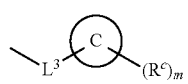

wherein:

Ring C represents a cyclopropyl ring, aryl, or a 5, 6 or 7 membered heterocyclyl or heteroaryl ring comprising 1-4 heteroatoms independently selected from N, O and S(O)$_r$;

L$^3$ is selected from —CH$_2$—, —O—, —SO$_2$—, —C(O)—, —C(O)—NH—, —HN—C(O)—, or a covalent bond;

R$^c$, at each occurrence, is selected from —R$^3$, —OR$^3$, =O, —CN, —C(O)—R$^3$, halo, —NR$^3$R$^4$, —NO$_2$, —SO$_2$R$^3$, —C(O)NR$^3$R$^4$ and —NR$^3$SO$_2$R$^4$;

R$^3$ and R$^4$ are independently selected from H, alkyl, alkenyl, alkynyl, cycloalkyl, cycloalkenyl, cycloalkynyl, aryl, heteroaryl and heterocyclyl;

each of the foregoing alkyl, alkenyl, alkynyl, cycloalkyl, cycloalkenyl, cycloalkynyl, aryl, heteroaryl and heterocyclyl moieties is further optionally substituted; and m is 0, 1, 2, 3 or 4.

In various embodiments, the following substructure:

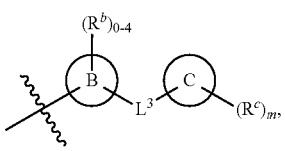

may be, for example,

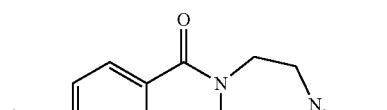

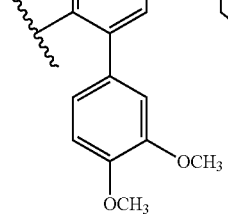

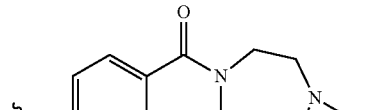

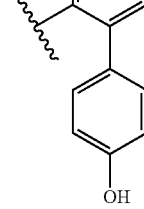

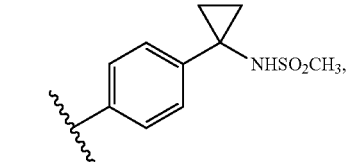

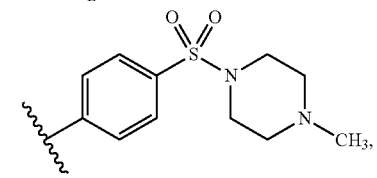

-continued

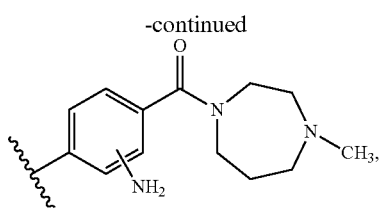

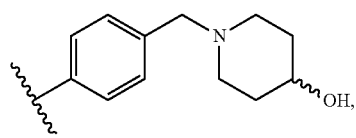

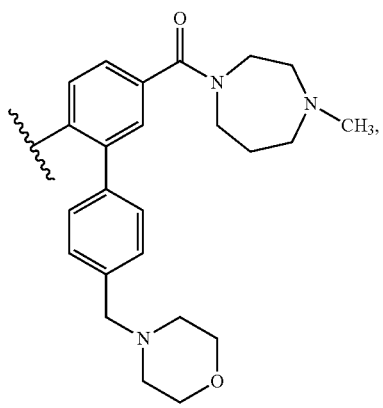

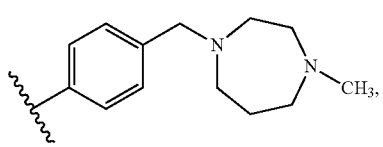

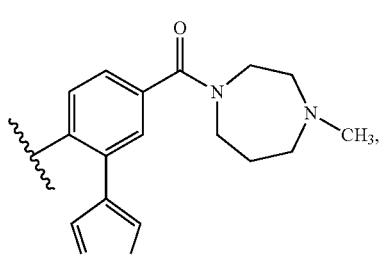

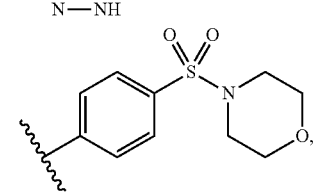

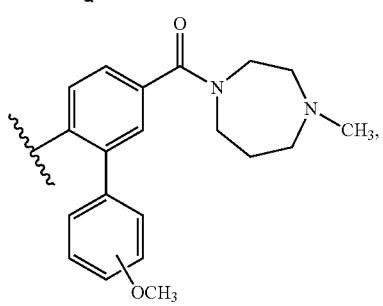

-continued
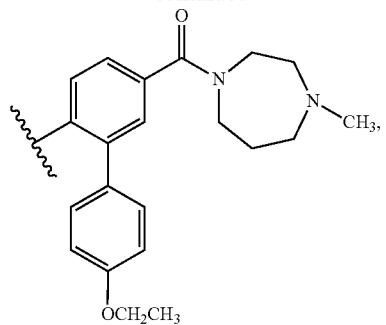
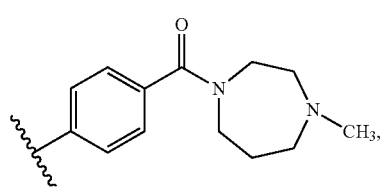
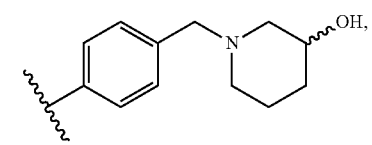
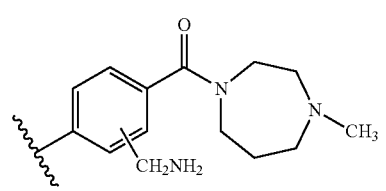
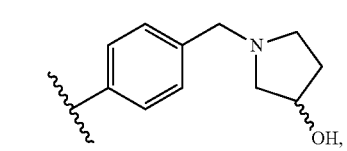
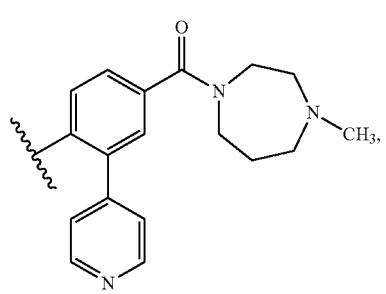
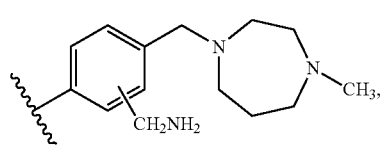
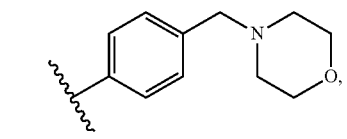
-continued
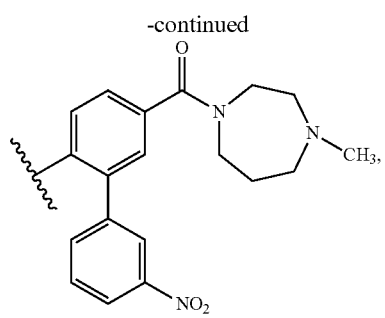
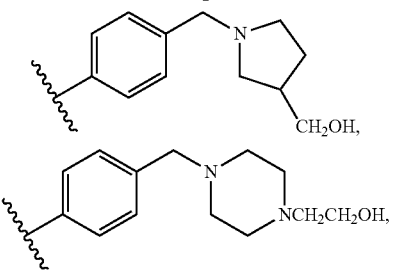
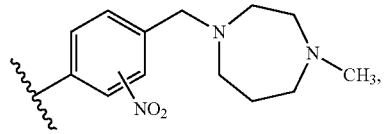
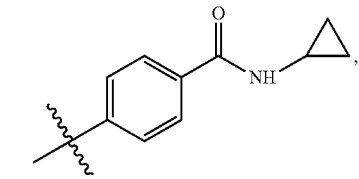
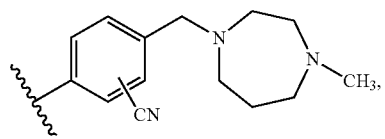
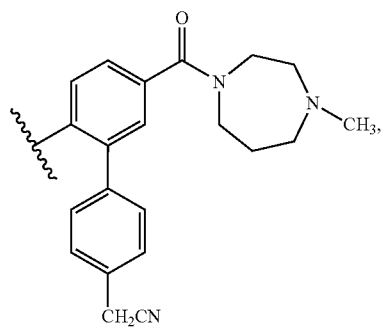
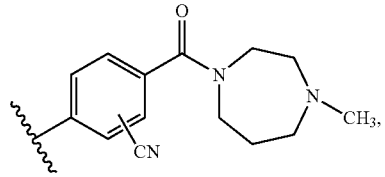
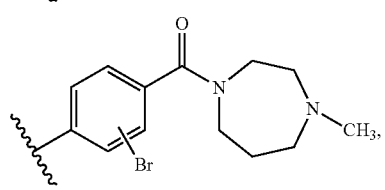

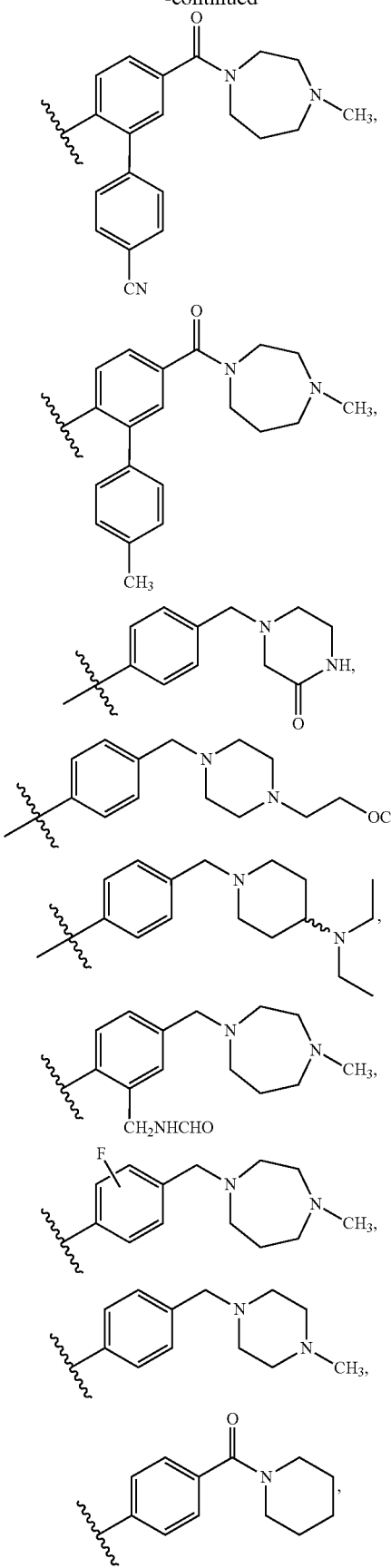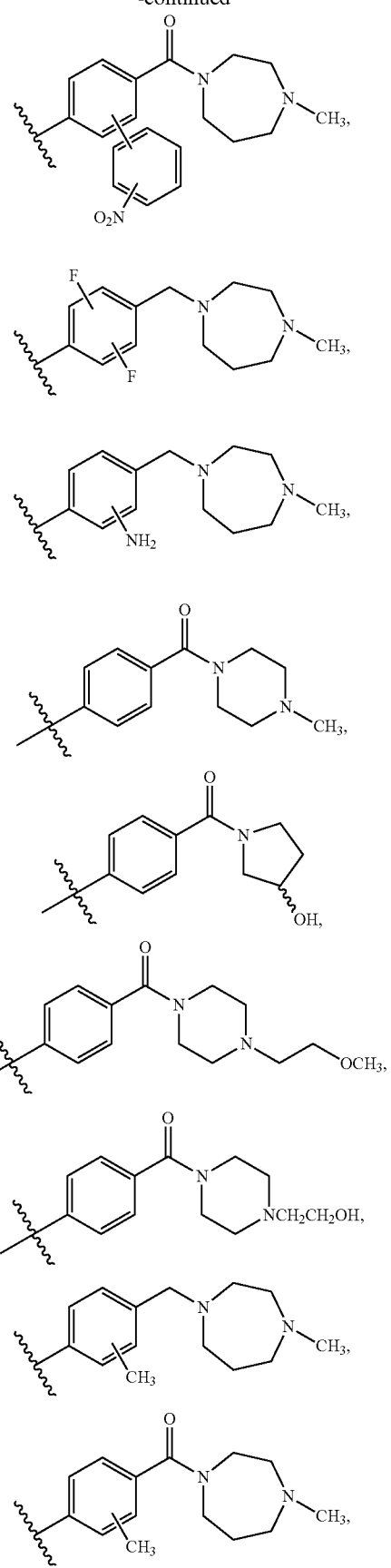

-continued
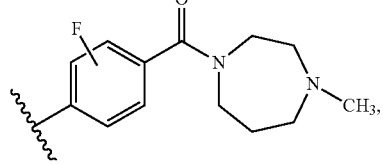
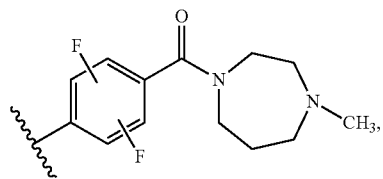
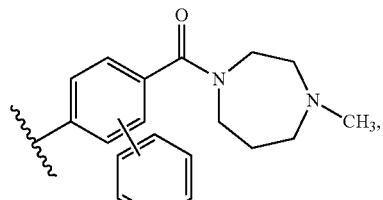
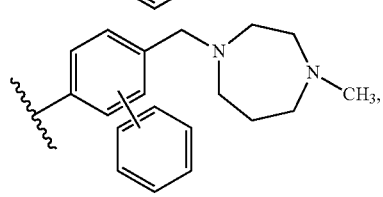
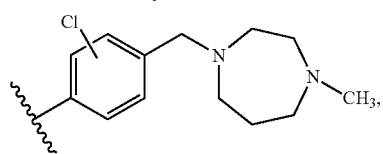
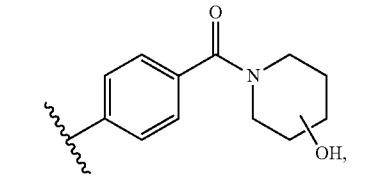
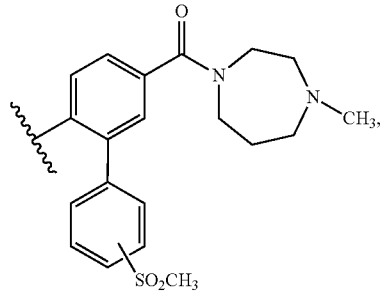
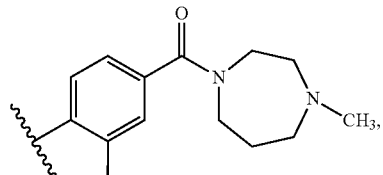
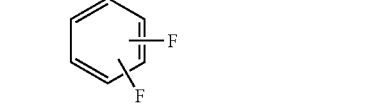
-continued
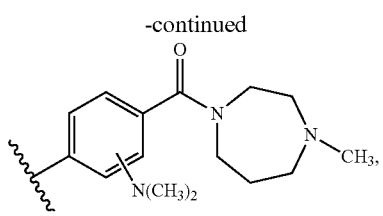
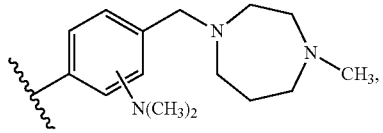
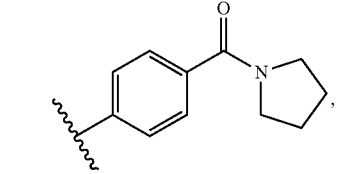
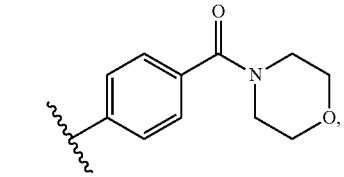
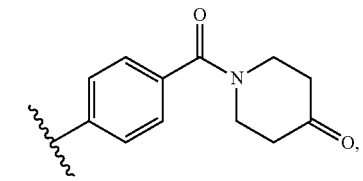
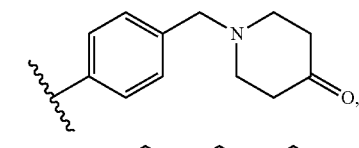
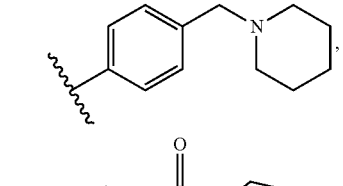
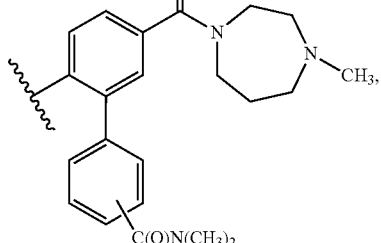
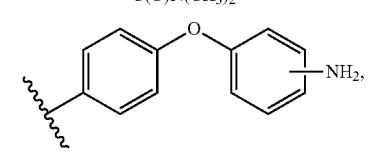
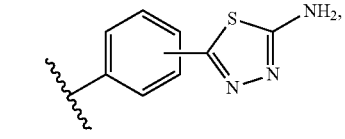

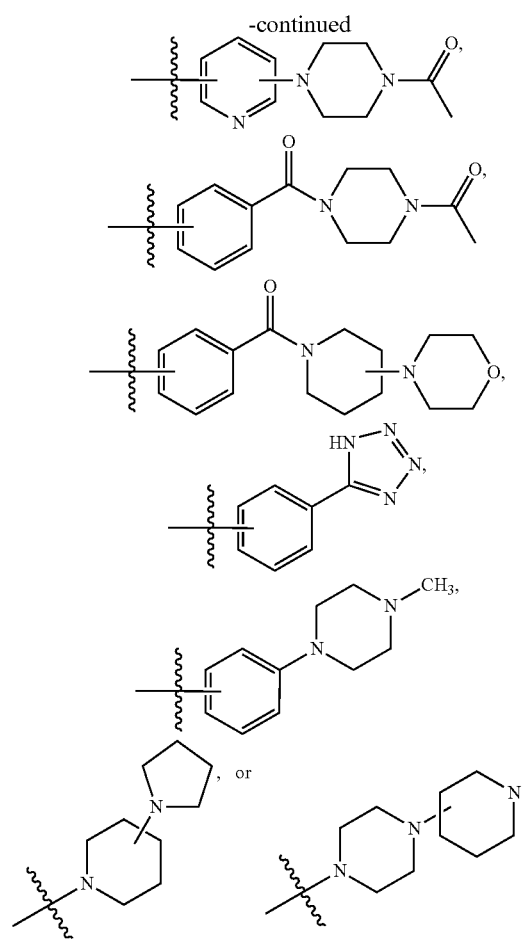
In various embodiments, the compounds of the present invention have the Formula (II), with all substituents defined as above:
In Formula (II), Ring A, substituted with $R^a$ on two adjacent ring atoms, and, taken together with said ring atoms to which they are attached, to form a 5-6 membered aryl or heteroaryl fused ring, may be selected from, for example:
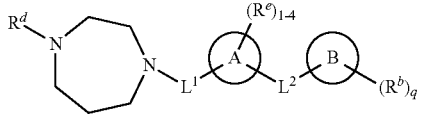
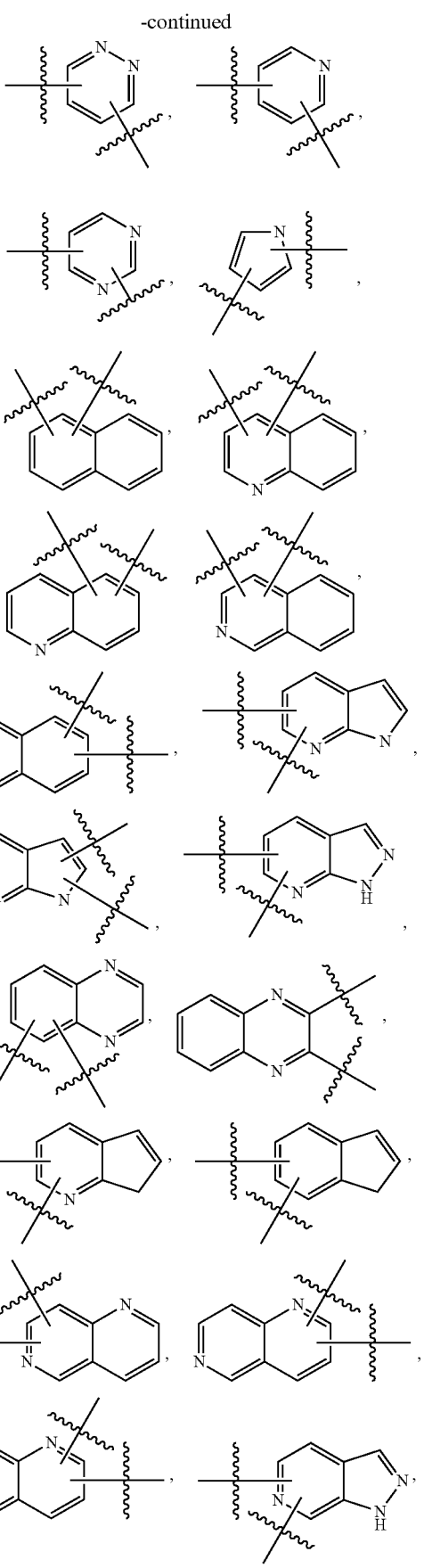

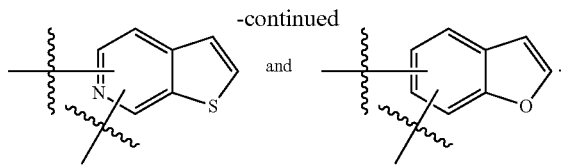

In various embodiments, compounds of the present invention have the Formula (III), with all substituents defined as above:

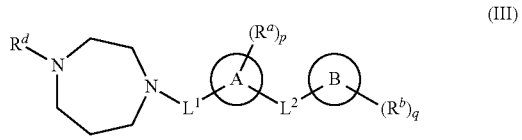

(III)

Formula (III) represents compounds of the present invention wherein Ring T is a 4-substituted-homopiperazin-1-yl moiety. $R^d$ is on the 4-position of the homopiperazine, and in various embodiments, is alkyl, alkenyl or cycloalkyl.

In various embodiments, compounds of the present invention have Formula (IV), with all substituents defined as above:

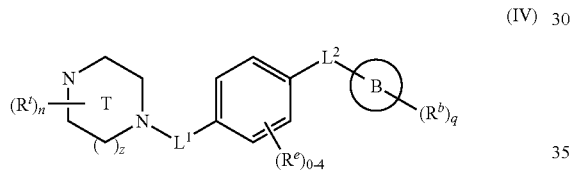

(IV)

In Formula (IV), Ring A is phenyl, and the connectivity of linkers $L^1$ and $L^2$ to Ring A is selected in the para position.

In various embodiments, compounds of the present invention have Formula (V), with all substituents defined as above:

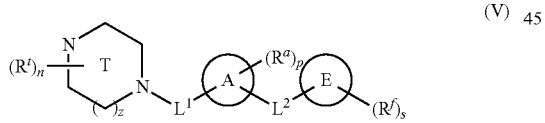

(V)

In Formula (IV), Ring E is selected from:
(i) phenyl, or a 5-6 membered heterocyclyl or heteroaryl ring containing 1-3 nitrogen atoms and 0-2 sulfur atoms with the remaining ring atoms being carbon; where s is from 1 to 5;
(ii) naphthalenyl; where s is 0; and
(iii) a 9-10 membered bicyclic hetero-aromatic ring containing 1-4 nitrogen ring atoms with the remaining ring atoms being carbon; where s is 0.

$R^f$ is selected from alkyl, cyano, halo, nitro, —$R^5$, —$R^6$, —$OR^5$, —$C(O)NR^5R^6$, —$C(R^5)$=$NR^6$, —$CH_2$—$C(O)NR^5R^6$, —$CH_2CH_2$—$C(O)NR^5R^6$, —$CH_2$—$R^5$, —$CH_2CH_2$—$R^5$, —$C_6H_4$—$CH_2$—$R^5$, —$NR^5R^6$, —$CH_2$—$NR^5R^6$, —$CH_2CH_2$—$NR^5R^6$, —$CH_2NHCH_2CH_2$—$NR^5R^6$, —$SO_2R^5$, —$SO_2NR^5R^6$, —$NHSO_2R^5$, —$C(O)$—$R^5$, and —$CO_2R^5$.
$R^5$ and $R^6$ are independently selected from H, alkyl, alkenyl, alkynyl, amino, amido, acetamido, acetyl, alkylaminocarbonyl, alkoxy, formyl, hydroxyl, cycloalkyl, heterocyclyl, aryl, heteroaryl, cyano, monoalkylamino, monocyclopropylamino, dialkylamino, dialkylphosphoryl, hydrazinyl, and acetyl hydrazinyl; and each of the alkyl, cycloalkyl, heterocyclyl, aryl and heteroaryl moieties is unsubstituted or substituted with one or more groups selected from alkyl, alkylsulfonamido, alkylsulfonyl, amino, n-butoxycarbonyl, t-butoxycarbonyl, carboxy, cyano, 1-cyanoethyl, 2-cyanoethyl, cyanomethyl, dialkylamino, dialkylaminocarbonyl, ethoxycarbonyl, 1-ethoxyethyl, 2-ethoxyethyl, ethoxymethyl, halo, 1-hydroxyethyl, 2-hydroxyethyl, hydroxyl, hydroxymethyl, methanesulfonyl, methoxycarbonyl, 1-methoxyethyl, 2-methoxyethyl, methoxymethyl, 4-morpholinyl, NH, nitro, i-propoxycarbonyl, and n-propoxycarbonyl; with the proviso that if z is 1 and Ring C is pyrazole, then s is 0.

In various embodiments, compounds of the present invention have Formula (VI):

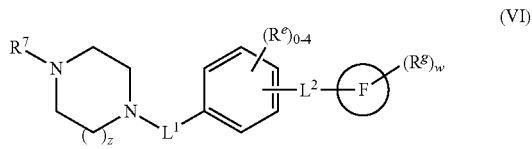

(VI)

wherein:
$R^7$ is alkyl or alkenyl;
$L^1$ is —$(CH_2)_x$—;
$R^e$ is selected from alkyl, cyano, halo, hydroxyl and nitro;
$L^2$ is selected from —$(CH_2)_x$—, —$(CH_2)_x$—NH—, or —NH—$(CH_2)_x$—;
Ring F is selected from 2-furan, 3-furan, 1-imidazole, 2-imidazole, 4-imidazole, 5-imidazole, 1-imidazolidine, 2-imidazolidine, 4-imidazolidine, 3-isothiazole, 4-isothiazole, 5-isothiazole, 3-isoxazole, 4-isoxazole, 5-isoxazole, 2-isoxazolidine, 3-isoxazolidine, 4-isoxazolidine, 5-isoxazolidine, 2-morpholinyl, 3-morpholinyl, 4-morpholinyl, 2-oxazole, 4-oxazole, 5-oxazole, phenyl, 1-piperadinyl, 2-piperadinyl, 3-piperadinyl, 4-piperadinyl, 1-piperazinyl, 2-piperazinyl, 1-pyrazolidine, 3-pyrazolidine, 4-pyrazolidine, 1-pyrazolyl, 3-pyrazolyl, 4-pyrazolyl, 2-pyridinyl, 3-pyridinyl, 4-pyridinyl, 2-pyrimidinyl, 4-pyrimidinyl, 5-pyrimidinyl, 1-pyrrolidinyl, 2-pyrrolidinyl, 3-pyrrolidinyl, 1-(2-pyrrolidonyl), 3-(2-pyrrolidonyl), 4-(2-pyrrolidonyl), 5-(2-pyrrolidonyl), 1-pyrrolyl, 2-pyrrolyl, 3-pyrrolyl, 2-(2,3,4,5-tetrahydropyridinyl), 3-(2,3,4,5-tetrahydropyridinyl), 4-(2,3,4,5-tetrahydropyridinyl), 5-(2,3,4,5-tetrahydropyridinyl), 6-(2,3,4,5-tetrahydropyridinyl), 1-(1,2,3,4-tetrahydropyridinyl), 2-(1,2,3,4-tetrahydropyridinyl), 3-(1,2,3,4-tetrahydropyridinyl), 4-(1,2,3,4-tetrahydropyridinyl), 5-(1,2,3,4-tetrahydropyridinyl), 6-(1,2,3,4-tetrahydropyridinyl), 1-(1,2,3,6-tetrahydropyridinyl), 2-(1,2,3,6-tetrahydropyridinyl), 3-(1,2,3,6-tetrahydropyridinyl), 4-(1,2,3,6-tetrahydropyridinyl), 5-(1,2,3,6-tetrahydropyridinyl), 6-(1,2,3,6-tetrahydropyridinyl), 2-thiazole, 4-thiazole, 5-thiazole, 2-thiazolidine, 3-thiazolidine, 4-thiazolidine, 5-thiazolidine, 2-thiomorpholinyl, 3-thiomorpholinyl, 4-thiomorpholinyl, 2-(thiomorpholinyl-1,1-dione), 3-(thiomorpholinyl-1,1-dione), 4-(thiomorpholinyl-1,1-dione), 1-(1,2,4-triazolyl), 3-(1,2,4-triazolyl), 4-(1,2,4-triazolyl), 1-(1,2,3-triazolyl), 2-(1,2,3-triazolyl), or 4-(1,2,3-triazolyl);

$R^g$ is selected from alkyl, cyano, halo, nitro, —$R^8$, —$R^9$, —$OR^8$, —C(O)$NR^8R^9$, —C($R^8$)=$NR^9$, —$CH_2$—C(O)$NR^8R^9$, —$CH_2CH_2$—C(O)$NR^8R^9$, —$CH_2$—$R^8$, —$CH_2CH_2$—$R^8$, —$C_6H_4$—$CH_2$—$R^8$, —$NR^8R^9$, —$CH_2$—$NR^8R^9$, —$CH_2CH_2$—$NR^8R^9$, —$CH_2NHCH_2CH_2$—$NR^8R^9$, —$SO_2R^8$, —$SO_2NR^8R^9$, —$NHSO_2R^8$, —C(O)—$R^8$, and $CO_2R^8$;

$R^8$ and $R^9$ are independently selected from H, alkyl, alkenyl, alkynyl, amino, amido, acetamido, acetyl, alkylaminocarbonyl, alkoxy, formyl, hydroxyl, cycloalkyl, heterocyclyl, aryl, heteroaryl, cyano, monoalkylamino, monocyclopropylamino, dialkylamino, dialkylphosphoryl, hydrazinyl, or acetyl hydrazinyl; each of the alkyl, cycloalkyl, heterocyclyl, aryl and heteroaryl moieties is unsubstituted or substituted with one or more groups selected from alkyl, alkylsulfonamido, alkylsulfonyl, amino, n-butoxycarbonyl, t-butoxycarbonyl, carboxy, cyano, 1-cyanoethyl, 2-cyanoethyl, cyanomethyl, dialkylamino, dialkylaminocarbonyl, ethoxycarbonyl, 1-ethoxyethyl, 2-ethoxyethyl, ethoxymethyl, halo, 1-hydroxyethyl, 2-hydroxyethyl, hydroxyl, hydroxymethyl, methanesulfonyl, methoxycarbonyl, 1-methoxyethyl, 2-methoxyethyl, methoxymethyl, 4-morpholinyl, NH, nitro, i-propoxycarbonyl, and n-propoxycarbonyl; and w is from 0 to 5, with the proviso that if z is 1 and Ring B is pyrazole, then w is 0; and with the proviso that if $L^2$ is —$(CH_2)_x$— and x is 0, then at least one $R^e$ or $R^g$ is present. This last proviso excludes the possibility that the phenyl ring and Ring F are both unsubstituted in Formula (VI).

In various embodiments of Formula (VI), the heterocyclyl moieties are selected from: 1-(4-methylhomopiperazinyl), 1-(4-methylpiperazinyl), 1-(4-acetylpiperazinyl), 1-[4-(2-methoxyethyl)piperazinyl], 4-morpholinyl, 1-piperidinyl, 1-(piperidin-4-onyl), 4-(piperazin-2-onyl), and 1-pyrrolidinyl. Any aryl is limited to only phenyl, and each of the above heteroaryl moieties is limited to 4-(1H-pyrazolyl), 2-(1,3,4-thiadiazolyl), 5-(1H-tetrazolyl), 2-pyridinyl, 3-pyridinyl, or 4-pyridinyl.

In various embodiments, compounds of the present invention have Formula (VII):

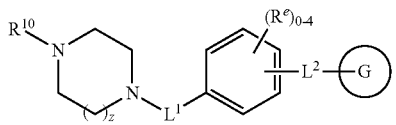

(VII)

In Formula (VII), $R^{10}$ is alkyl or alkenyl;

$R^e$ is selected from —$CH_3$, cyano, halo, hydroxyl and nitro;

$L^2$ is selected from —$(CH_2)_x$—, a covalent bond, —O—, —$CH_2$—NH—, and —NH—$CH_2$—; and Ring G is selected from unsubstituted indenyl, 2,3-dihydro-1H-indenyl, 1-indolinyl, 2-indolinyl, 3-indolinyl, 1-indolyl, 2-indolyl, 3-indolyl, 1-isoindolinyl, 2-isoindolinyl, 3-isoindolinyl, 1-isoindolyl, 2-isoindolyl, 3-isoindolyl, benzpyrazolyl, benzimidazolyl, 1H-pyrrolo[2,3b]pyridinyl, 1H-pyrrolo[2,3c]pyridinyl, 1H-pyrrolo[3,2c]pyridinyl, 1H-pyrrolo[3,2b]pyridinyl, naphthalenyl, quinolinyl, isoquinolinyl, phthalazinyl, quinazolinyl, quinoxalinyl, 2,6-naphthyridinyl, 2,7-naphthyridinyl, 1,5-naphthyridinyl, 1,6-naphthyridinyl, 1,7-naphthyridinyl, and 1,8-naphthyridinyl.

In various embodiments, compounds of the present invention may be represented by the general Formula (VIII):

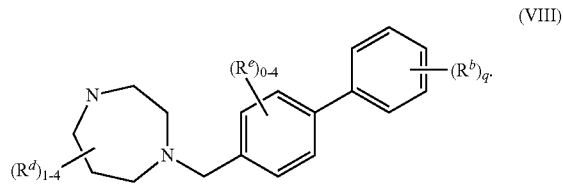

(VIII)

For the compounds having Formula (VIII):

$R^d$ is alkyl or alkenyl;

$R^e$ is selected from —$CH_2R^{11}$, —$OR^{12}$, —$NHSO_2CH_3$, —$CO_2H$, —$CO_2CH_3$, —$CF_3$, —CN, halo and —$NO_2$;

$R^{11}$ is selected from —$NH_2$, —OH and —$N(CH_3)_2$;

$R^{12}$ is selected from —$CH_3$, —$CH_2CH_3$, —$CH_2CH_2OH$, —$CH_2CN$, —$CH_2OCH_3$ and —$CH_2CONH_2$; and, $R^b$ is selected from:

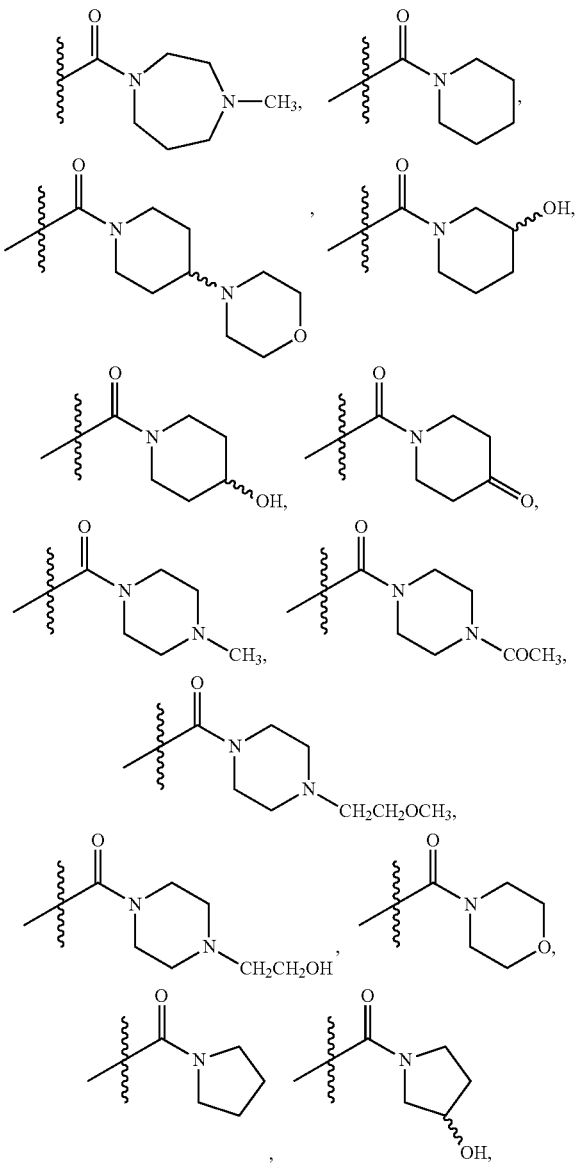

-continued

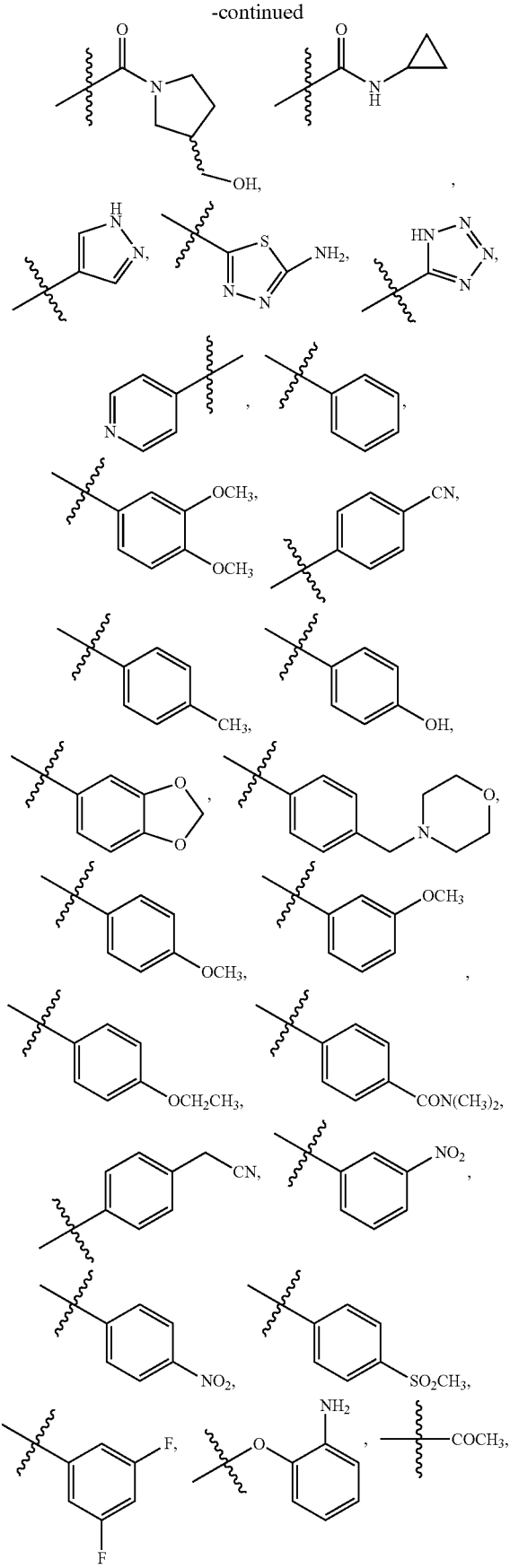

-continued

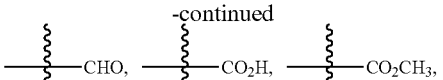

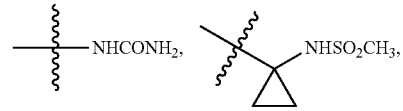

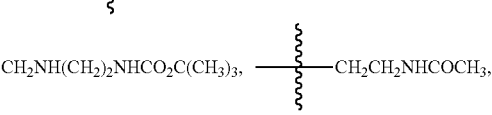

Compounds of Formula (VIII) exclude compounds devoid of substitution on the biphenyl rings. That is, compounds of Formula (VIII) have at least one $R^e$ or $R^b$ group.

3. Definitions

As used herein, the term "alkyl" means acyclic linear and branched hydrocarbon groups, e.g. "$(C_1$-$C_8)$alkyl". Examples of alkyl groups include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, Isohexyl, cyclohexyl, etc. Other alkyl groups will be readily apparent to those of skill in the art given the benefit of the present disclosure. An alkyl group may be optionally substituted with one or more functional groups, discussed below.

As used herein, "-alkyl-", when embedded within substituents such as, for example, -alkyl-C(O)—$R^1$, -alkyl-C(O)$NR^1R^2$, -alkyl-$R^1$, $R^1$-alkyl-$R^2$, and -alkyl-$NR^1R^2$, means a divalent hydrocarbon residue of any carbon length and any degree of unsaturation, optionally substituted with one or more functional groups, discussed below.

As used herein, "alkenyl" means any linear or branched hydrocarbon chains having one or more unsaturated carbon-carbon bonds that may occur in any stable point along the chain, e.g. "$(C_2$-$C_8)$alkenyl". For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. Furthermore, an alkenyl groups may be substituted with one or more functional groups, discussed below.

As used herein, "alkynyl" means any hydrocarbon chain of either linear or branched configuration, having one or more carbon-carbon triple bonds occurring in any stable point along the chain, e.g. "$(C_2$-$C_8)$alkynyl". Examples of an alkynyl group includes prop-2-ynyl, but-2-ynyl, but-3-ynyl, pent-2-ynyl, 3-methylpent-4-ynyl, hex-2-ynyl, hex-5-ynyl, etc. "Alkynyl" groups may be substituted with one or more functional groups, discussed below.

As used herein, the term "cycloalkyl" means a nonaromatic, saturated, monocyclic or multicyclic substituent, e.g. "$(C_3$-$C_{10})$cycloalkyl." Multicyclic, individual rings can be fused, bridged, or spirocyclic, in addition to having covalent bond substitution. Examples of a cycloalkkyl group includes cyclopropyl, cyclobutyl, cyclopentyl, cyclohexyl, norbornanyl, bicyclo[3.2.1]octanyl, octahydro-pentalenyl, and spiro[4.5]decanyl, and the like. The term "cycloalkyl" may be used interchangeably with the term "carbocycle". A cycloalkyl group may be optionally substituted with one or more functional groups, discussed below.

As used herein, the term "cycloalkenyl" means a nonaromatic, unsaturated, monocyclic or multicyclic substituent, e.g. "($C_5$-$C_{13}$)cycloalkenyl." Examples a cycloalkenyl group includes cyclopent-1-en-1-yl, and cyclohex-1-en-1-yl, and the like. A cycloalkenyl groups may be optionally substituted with one or more functional groups discussed below.

As used herein, the term "cycloalkynyl" means a stable cyclic or polycyclic hydrocarbon groups of from 5 to 13 carbon atoms, containing at least one carbon-carbon triple bond, e.g. "($C_5$-$C_{13}$)cycloalkynyl". Examples include cycloct-5-yn-1-yl, and the like. A cycloalkynyl group may be optionally substituted with one or more functional groups discussed below.

As used herein, the term "alkylenyl" means the divalent, saturated hydrocarbon radicals —$(CH_2)_x$—, e.g., "($C_1$-$C_8$) alkylenyl". Examples include —$CH_2$—, —$CH_2$—CH($CH_3$)—$CH_2$— and —$CH_2CH_2CH_2$—, and the like, with any degree of branching. An alkylenyl group may be optionally substituted with one or more functional groups discussed below.

As used herein, the term "alkenylenyl" means the divalent, hydrocarbon alkylenyl radicals described above having any degree of unsaturation in any position, e.g., "($C_1$-$C_8$) alkenylenyl". Examples include —CH=CH—, —CH=CHCH$_2$—, —CH$_2$CH$_2$CH=CH—, and —CH$_2$CH=CHCH$_2$—, and the like. An alkenylenyl group may be optionally substituted with one or more functional groups, discussed below.

As used herein, the term "heteroalkylenyl" means the divalent, saturated hydrocarbon alkylenyl radicals described above having any number of any types of heteroatoms in any position, e.g. "($C_1$-$C_8$)heteroalkylenyl". Examples include —CH$_2$—NH—CH$_2$—, —S—CH$_2$—NH—CH$_2$—, —CH$_2$—O—CH$_2$—, —O—CH$_2$—CH$_2$—CH$_2$—O—, and —O—C(CH$_3$)$_2$—C(CH$_3$)$_2$—O—, and the like. A heteroalkylenyl group may be optionally substituted with one or more functional groups discussed below.

As used herein, the term "heteroalkenylenyl" means the divalent, unsaturated hydrocarbon alkenylenyl radicals described above having any number of any types of heteroatoms in any position, e.g. "($C_1$-$C_8$)heteroalkenylenyl". Examples include —CH$_2$—N=CH— and —CH$_2$—S—CH$_2$—NH=CH—CH$_2$—, and the like. A heteroalkenylenyl group may be optionally substituted with one or more functional groups, discussed below.

As used herein, the term "alkoxy" means an alkyl, or an alkenyl group, linear, branched or cyclic, attached through an oxygen bridge, e.g., "($C_1$-$C_8$)alkoxy". Examples include —OCH$_3$, —OCH$_2$CH$_3$, —O—CH(CH$_3$)$_2$, —OCH$_2$CH=CH$_2$, and the like. An alkoxy group may be optionally substituted with one or more functional groups discussed below.

As used herein, the term "aryl" means a single ring structure that is polyunsaturated and aromatic, such as for example phenyl. The term "aryl" may be used alone or as part of a larger moiety as in "aralkyl", "aralkoxy", or "aryloxy-alkyl", indicating the inclusion of "aryl" as a divalent radical. Anryl group may be optionally substituted with one or more functional groups discussed below.

As used herein, the term "heterocyclyl" means a nonaromatic, single ring structure having at least one of any type of heteroatom as ring atoms, and having any degree of unsaturation, e.g. "($C_3$-$C_{10}$)heterocycloalkyl", (excluding aromatic heterocyclic rings that are defined as "heteroaryl" below). The one or more heteroatoms may be selected from nitrogen, sulfur, and oxygen. The heterocycloalkyl group can be attached as a substituent via a carbon atom or a heteroatom, e.g. a nitrogen atom. Examples include 2-tetrahydrofuranyl, 3-tetrahydrofuranyl, dihydrofuranyl, tetrahydropyranyl, pyranyl, thiopyranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 1,3-oxazolidin-3-yl, isothiazolidinyl, 1,3-thiazolidin-3-yl, 1,2-pyrazolidin-2-yl, 1,3-pyrazolidin-1-yl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperizin-2-onyl, piperizin-3-onyl, 2-pyrrolinyl, 3-pyrrolinyl, imidazolidinyl, 2-imidazolidinyl, 1,4-dioxanyl, and 4-thiazolidinyl, and the like. The term "heterocycle", "heterocyclyl", "heterocyclic", and "heterocyclic ring" are used interchangeable herein. A heterocyclyl group may be optionally substituted with one or more functional groups discussed below.

As used herein, the term "heteroaryl" means a single ring polyunsaturated and aromatic moiety having at least one of any type of heteroatom, e.g. "($C_5$-$C_{14}$)heteroaryl". Examples include 5-membered monocyclic rings such as thienyl, pyrrolyl, imidazolyl, pyrazolyl, furyl, isothiazolyl, furazanyl, isoxazolyl, thiazolyl and the like; and 6-membered monocyclic rings such as pyridyl, pyrazinyl, pyrimidinyl, pyridazinyl, triazinyl and the like. For further examples, see e.g. Katritzky, Handbook of Heterocyclic Chemistry. Further specific examples of heteroaryl rings include 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl and carbazolyl. The term "heteroaryl" also refers to rings that are optionally substituted. The term "heteroaryl" may be used interchangeably with the term "heteroaryl ring" or the term "heteroaromatic". A heteroaryl group may be optionally substituted with one or more functional groups discussed below.

As used herein, the term "halo" means fluorine, chlorine, bromine, or iodine.

As used herein, the term "amino" means a free radical having a nitrogen atom and 1 to 2 hydrogen atoms. As such, the term amino generally refers to primary and secondary amines. In that regard, as used herein and in the appended claims, a tertiary amine substituent is represented by the general formula RR'N—, wherein R and R' are carbon radicals that may or may not be identical, and that may or may not connect into a N-heterocyclic ring. Nevertheless, the term "amino" generally may be used herein to describe a primary, secondary, or tertiary amine, and those of skill in the art will readily be able to ascertain the identification of which in view of the context in which this term is used in the present disclosure.

As used herein, a circle having a capital letter designation in the circle, such as A, B or C, means a generic single ring structure having no specific number or type of ring atoms and no particular stereochemistry or regiochemistry with regard to any substitution or connectivity to other rings.

Any of the above defined substitutents may be optionally substituted with one or more functional groups. When an acyclic or cyclic substituent is optionally substituted, (e.g., an alkyl, alkenyl, alkynyl, cycloalkyl, cycloalkenyl, heterocyclyl, aryl, or heteroaryl substituent), it is understood that the total number of substituents does not exceed the normal available valencies or the carbon or heteroatom substituted under the existing conditions. Thus, for example, a phenyl ring substituted with "p" substituents (where "p" ranges from 0 to 5) can have 0 to 5 substituents, whereas it is understood that a pyridinyl ring substituted with "p" substituents has a number of substituents ranging from 0 to 4. Also, nitrogen may be quaternized as a quaternium salt. The maximum number of substituents that a group in the compounds of the invention may have can be easily determined. In the instances where there is no further substitution on a carbon or heteroatom, hydrogen atoms are presumed present to fill the remaining valence. Thus for example, an "unsubstituted phenyl ring" is presumed to be $-C_6H_5$, i.e., having hydrogen atoms in place of optional substitution in order to fill the requisite valence.

In general, the present invention encompasses substituents and variables that result in those compounds that are stable and/or chemically feasible. A stable compound or chemically feasible compound is one that has stability sufficient to permit its preparation and detection. Preferred compounds of this invention are sufficiently stable that they are not substantially altered when kept at a temperature of 40° C. or less, in the absence of moisture or other chemically reactive conditions, for at least a week.

Exemplary "optional substitution" is set out herein below for the various substituents defined above.

As used herein, the phrase "optionally substituted with one or more functional groups" means that any substituent defined above, such as for example "alkyl", "heteroalkyl", "aryl" and the like, can have any number of functional groups appended onto the particular substituent. Examples of functional groups usable as "optional substitution" include —H, amino, alkylamino, dialkylamino, aminocarbonyl, halo, acetyl, alkyl, alkenyl, alkynyl, cycloalkyl, cycloalkenyl, cycloalkynyl, cyanoalkyl, heterocyclyl, aryl, heteroaryl, alkylaminocarbonyl, dialkylaminocarbonyl, alkylaminocarbonyloxy, dialkylaminocarbonyloxy, alkylsulfonyl, alkoxysulfonyl, alkylsulfonamido, nitro, cyano, carboxy, alkoxycarbonyl, alkylcarbonyl, hydroxy, hydrogen, hydroxyalkyl, haloalkyl, alkoxy, alkoxyalkyl, acyloxy, haloalkoxy, =O, =S, —SO$_2$R', =NH, =N—OH, =N—R', —N—NR'R''', —N—NHC(O)R', —N—NHCO$_2$R', —N—NHSO$_2$R', R', —C(O)SR', —C(=NR')NR'R'', —C(=NR')OR'', —C(=NR')R''', —C(O)—C(O)R', —P(O)R'R'', —Si—R'R''R''', —Si—NR'SO$_2$R'', and —NR'SO$_2$NR'R'', wherein R', R'' and R''' at each occurrence are independently hydrogen, hydroxyl, alkyl, alkenyl, alkynyl, cycloalkyl, cycloalkenyl, cycloalkynyl, aryl, heteroaryl or heterocyclyl, or wherein any two of R', R'' and R''', taken together with the single carbon or heteroatom to which they attach, form a carbocyclic, heterocyclic, aryl, or heteroaryl ring. Hydroxy may be protected by any protecting group. Any two hydroxyl groups may be part of a cyclic protecting group.

"Alkyl" groups, along with -alkyl-divalent radicals, may be substituted anywhere in the chain of carbon atoms with any number of heteroatoms selected from N, O and S. That is, any carbon atom can be replaced by a heteroatom. Thus for example, "alkyl" includes —CH$_2$NHCH$_3$, —CH$_2$—S—CH$_3$, and the like. Also for example, the general substituent -alkyl-NR'R'' necessarily includes the specific substituent —CH$_2$NHCH$_2$CH$_2$—NHCO$_2$$^t$Bu, where the "-alkyl-" portion of the substituent is "—CH$_2$NHCH$_2$CH$_2$—", a butylene residue, ("alkyl" in the broader definition), with the second carbon replaced with "NH".

In various embodiments, optional halo substitution on "alkyl" provides for such groups as fluoromethyl, difluoromethyl, trifluoromethyl, perfluoroethyl, and the like Heterocyclic substituents as defined above may be optionally substituted with one or more divalent heteroatoms replacing hydrogen atoms or pairs of electrons. Thus for example, thiomorpholine-1,1-dione is included within "optionally substituted heterocyclyl" as it is a heterocyclic ring, (thiomorpholine), substituted two "=O" groups on the same sulfur atom of the ring. In another exemplary embodiment, 2-pyrrolidinone is also included within "optionally substituted heterocyclyl". Pyrrolidine comprises a heterocyclyl; the substitution of a single "=O" group on a carbon atom adjacent to the ring nitrogen atom provides 2-pyrrolidinone.

Certain compounds of this invention may exist in tautomeric forms, and this invention includes all such tautomeric forms of those compounds unless otherwise specified. Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers. Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. Optically active compounds of the invention can be obtained by using active starting materials. These isomers may be in the form of a free acid, a free base, an ester or a salt. The compounds of this invention can exist in radiolabelled form, i.e., said compounds may contain one or more atoms containing an atomic mass or mass number different from the atomic mass or mass number: ordinarily found in nature. Radioisotopes of hydrogen, carbon, phosphorous, fluorine and chlorine include $^3$H, $^{14}$C, $^{32}$P, $^{35}$S, $^{43}$F and $^{36}$Cl, respectively. Compounds of this invention which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability. Radiolabelled compounds of this invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

As used herein, the term "pharmaceutically acceptable salt" means either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained. It includes those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds are well known in the art. For example, S. M. Berge, et al. describes pharmaceutically acceptable salts in detail in J. Pharmaceutical Sciences, 66: 1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methane-sulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue (MW>300) thereof. Pharmaceutically acceptable derivatives thus include among others pro-drugs.

As used herein, the term "prodrug" means a pharmacological derivative of a parent drug molecule that requires biotransformation, either spontaneous or enzymatic, within the organism to release the active drug. For example, prodrugs are variations or derivatives of the compounds of Formula (I) that have groups cleavable under certain metabolic conditions, which when cleaved, become the compounds of Formula (I). Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, *Design of Prodrugs*, pp. 7-9, 21-24, Elsevier, Amsterdam 1985; Silverman, *The Organic Chemistry of Drug Design and Drug Action*, pp. 352-401, Academic Press, San Diego, Calif., 1992; T. Higuchi and V. Stella, Pro-drugs as Novel Delivery Systems, Vol. 14 of the A.C.S. Symposium Series; and Edward B. Roche, ed., Bioreversible Carriers in Drug Design, American Pharmaceutical Assocn. and Pergamon Press, 1987, each incorporated herein by reference. Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

As used herein, the term "pharmaceutically acceptable carrier or adjuvant" means a carrier or adjuvant that may be administered to a patient together with a compound of this invention, which does not destroy the pharmacological activity thereof and is nontoxic when administered in doses sufficient to deliver a therapeutic amount of the compound. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

A "pharmaceutically acceptable ester" includes esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

Various abbreviations used herein include: ACN refers to acetonitrile; DMF refers to N,N-dimethylformamide; DMSO refers to dimethylsulfoxide; EtOAc refers to ethyl acetate; EtOH refers to ethanol; Hunig's Base refers to diisopropylethyl amine ("DIPEA"); MeOH refers to methanol; NaOH refers to sodium hydroxide; THF refers to tetrahydrofuran; and TFA refers to trifluoroacetic acid.

"Administration," as used herein, refers to the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

The expression "dosage unit form," as used herein, refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; and like factors well known in the medical arts.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, and the like.

4. Pharmaceutical Methods; Compositions; Formulations; Uses

The method of the invention comprises administering to a subject in need thereof a therapeutically effective amount of a compound of the present invention.

A compound of the present invention, or a composition comprising at least one compound of the present invention, may be administered using any amount and any route of administration effective for killing or inhibiting the growth of tumors or other forms of cancer.

The anticancer compounds of the present invention are preferably formulated in dosage unit form for ease of administration and uniformity of dosage.

Furthermore, after formulation with at least one pharmaceutically acceptable carrier in a desired dosage, the compositions of this invention can be administered to humans and other animals, orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the compound will typically be in the range of 0.01 to 500 mg of compound per kg of patient body weight, preferably 0.1 to 125 mg/kg, and in some cases, 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

Compounds

Compounds of present invention can exist in free form for treatment, or where appropriate, as a pharmaceutically acceptable salt or other derivative, defined and discussed above.

Compositions

Compositions are provided which comprise at least one of the compounds described herein (or a prodrug, pharmaceutically acceptable salt or other pharmaceutically acceptable derivative thereof), and one or more pharmaceutically acceptable carriers or excipients. These compositions may further comprise one or more additional therapeutic agents.

As described herein, a pharmaceutically acceptable carrier includes for example any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except where a conventional carrier medium is incompatible with the compounds of the invention, such as when producing any undesirable biological effect or otherwise interacting in a deleterious manner with any other component(s) of the pharmaceutical composition, the use of any carrier medium is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention in association with one or more pharmaceutically-acceptable carriers and/or diluents and/or adjuvants (collectively referred to herein as "carrier" materials), and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of compounds administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the phase may comprise merely an emulsifier, it may comprise a mixture of at least one emulsifier with a fat or an oil, or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10%, and particularly about 1.5% w/w. Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature, and will therefore melt in the rectum and release the drug.

The pharmaceutical compositions may be subjected to conventional pharmaceutical operations such as sterilization and/or may contain conventional adjuvants, such as, preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, anti-inflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein, or a pharmaceutically acceptable salt thereof, and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, anti-inflammatory agents, antifungal agents, antibiotics, or anti-vascular hyperproliferation compounds.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which are known in the art.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The compounds of the present invention are thus of interest for the treatment of cancers, including both primary and metastatic cancers, including solid tumors as well as lymphomas and leukemias, and including cancers which are resistant to other therapies.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers and leukemias (e.g., myeloid, lymphocytic, myelocytic and lymphoblastic leukemias) including cases which are resistant to one or more other therapies.

Resistance to various anticancer agents can arise from one or more mutations in a mediator or effector of the cancer (e.g., mutation in a choline kinase) which correlate with alteration in the protein's drug binding properties, phosphate binding properties, protein binding properties, autoregulation or other characteristics.

Compounds of this invention are contemplated to be useful against various cancers, including those which are resistant in whole or part to other anticancer agents, and specifically including leukemias involving one or more mutations in choline kinase, within or outside the kinase domain, including but not limited to those noted in any of the known literature.

5. Synthetic Overview; Examples

The practitioner has a well-established literature of heterocyclic, heteroaryl, aryl and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for the R substituents, Ring T, Ring A, Ring B, Ring C, Ring D, and Ring E.

Various synthetic approaches may be used to produce the compounds described herein, including those approaches depicted schematically below. The practitioner will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new chiral centers); and the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and removal) and other synthetic chemistry transformations useful in producing the compounds described herein, see in R. Larock, Comprehensive Organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire contents of these references are hereby incorporated by reference.

Also, one may choose reagents enriched for a desired isotope, e.g. deuterium in place of hydrogen, to create compounds of this invention containing such isotope(s). Compounds containing deuterium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of this invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent system appropriate to the reagents and materials employed and suitable for the transformation being effected. It will be understood by those skilled in the art of organic synthesis that the functionality present on the molecule should be consistent the transformations proposed. This will sometimes require some judgment in modifying the order of the synthetic steps or the selection of a particular process scheme over another in order to obtain a desired compound of the invention.

In various embodiments, compounds of the present invention may be prepared as outlined in Scheme I below, supplemented and/or modified with any necessary methods known to those skilled in the art.

The following representative examples contain important additional information, exemplification and guidance, which can be adapted to the practice of this invention in its various embodiments and equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of this invention, the chemical elements are identified in accordance with the Periodic Table of the Elements, CAS version, Handbook of Chemistry and Physics, 75.sup.th Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

a brief heating the reaction mixture may be extracted with DCM and the reaction product XII purified by thin layer chromatography (e.g. DCM/methanol solvent). Reaction 2 is a reductive amination reaction of intermediate XII, when Y=H, with an amine $HNR^{10}R^{11}$, sodium triacetoxyborohydride and molecular sieves in DCM. The reaction mixture is diluted with aqueous sodium bicarbonate and extracted with DCM to give the crude product XIII. Amine XIII may be purified by thin layer chromatography. Reaction 3 is a

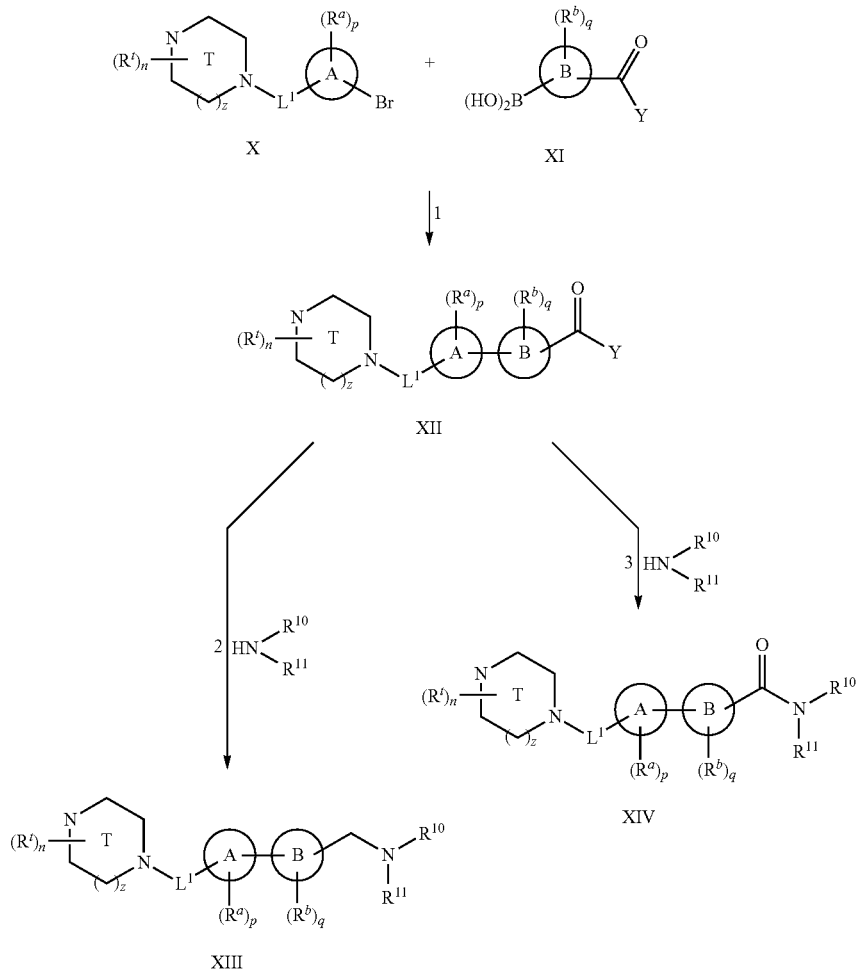

Scheme I

Scheme I is suitable for the preparation of compounds where Ring A and Ring B are directly bonded together, (i.e. $L^2$ in structural formula I above is a covalent bond). In Scheme I, Y is either H or any alkoxy group, such as methoxy. $R^{10}$ and $R^{11}$ are independently selected from H, alkyl, alkenyl, alkynyl, cycloalkyl, cycloalkenyl, cycloalkynyl, aryl, heteroaryl and heterocyclyl, or, $R^{10}$ and $R^{11}$ together with the nitrogen atom to which they are attached, form a heterocyclic amine. Each of the foregoing alkyl, alkenyl, alkynyl, cycloalkyl, cycloalkenyl, cycloalkynyl, aryl, heteroaryl and heterocyclyl moieties is optionally substituted.

Scheme I begins with coupling Reaction 1 between an aryl or heteroaryl bromide X and an aryl or heteroaryl boronic acid XI using palladium acetate, triphenylphosphine and potassium carbonate in aqueous acetonitrile. Following direct amidation reaction of the ester XII, when Y=alkoxy such as $OCH_3$, with the amine $HNR^{10}R^{11}$ in the presence of trimethylaluminum in 1,2-dichloroethane. The reaction mixture is poured onto wet sodium bicarbonate and extracted with DCM. The amide XIV may be purified by thin layer chromatography. In various embodiments, the use of trimethylaluminum as the amidation catalyst in Reaction 3 may also result in various methylation reactions.

The following exemplary compounds, provided in Examples 1-16, may be synthesized by the coupling Reaction 1 followed by the reductive amination Reaction 2 in accordance with Scheme I, wherein Ring T is 4-methylhomopiperazine, Ring A and Ring B are phenyl, Y=H, and $L^1$ is methylene:

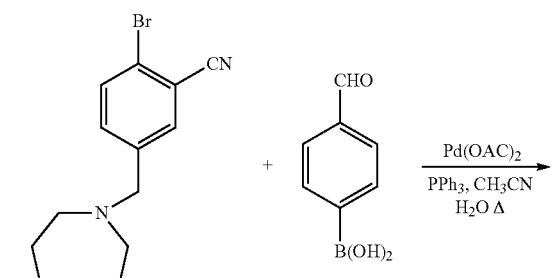

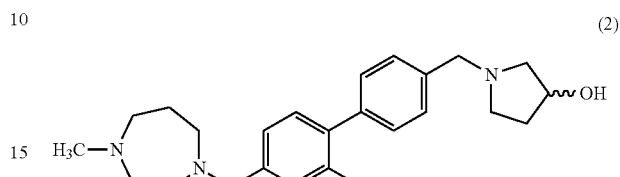

Example 1

4'-((3-hydroxypiperidin-1-yl)methyl)-4-((4-methyl-1,4-diazepan-1-yl)methyl)-[1,1'-biphenyl]-2-carbonitrile (1)

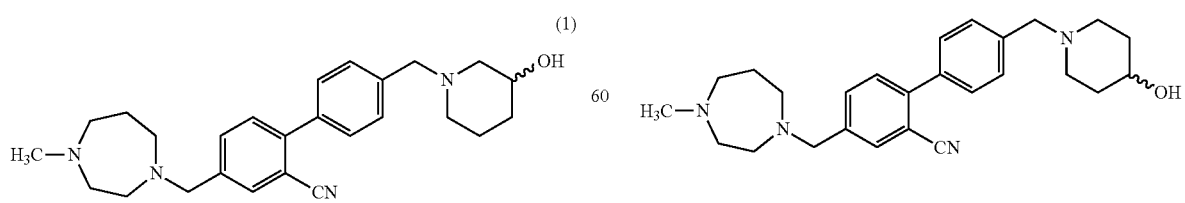

wherein the amine HNR[10]R[11] used for Reaction 2 was 3-hydroxypiperidine.

Example 2

4'-((3-hydroxypyrrolidin-1-yl)methyl)-4-((4-methyl-1,4-diazepan-1-yl)methyl)-[1,1'-biphenyl]-2-carbonitrile

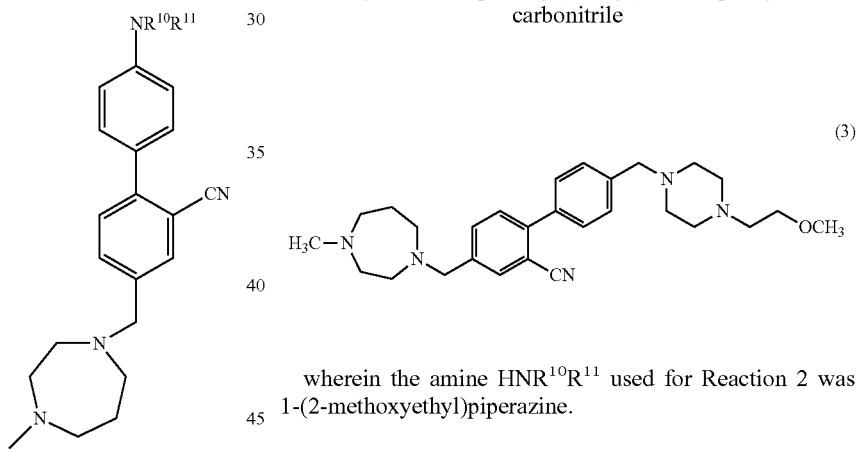

wherein the amine HNR[10]R[11] used for Reaction 2 was 3-hydroxypyrrolidine.

Example 3

4'-((4-(2-methoxyethyl)piperazin-1-yl)methyl)-4-((4-methyl-1,4-diazepan-1-yl)methyl)-[1,1'-biphenyl]-2-carbonitrile wherein the amine HNR[10]R[11] used for Reaction 2 was 1-(2-methoxyethyl)piperazine.

Example 4

4'-((4-hydroxypiperidin-1-yl)methyl)-4-((4-methyl-1,4-diazepan-1-yl)methyl)-[1,1'-biphenyl]-2-carbonitrile wherein the amine HNR[10]R[11] used for Reaction 2 was 4-hydroxypiperidine.

Example 5

4'-((3-(hydroxymethyl)pyrrolidin-1-yl)methyl)-4-((4-methyl-1,4-diazepan-1-yl)methyl)-[1,1'-biphenyl]-2-carbonitrile

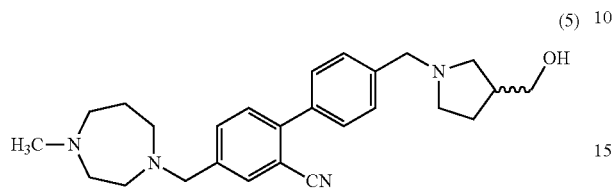
(5)

wherein the amine $HNR^{10}R^{11}$ used for Reaction 2 was 3-(hydroxymethyl)pyrrolidine.

Example 6

4'-((4-(2-hydroxyethyl)piperazin-1-yl)methyl)-4-((4-methyl-1,4-diazepan-1-yl)methyl)-[1,1'-biphenyl]-2-carbonitrile

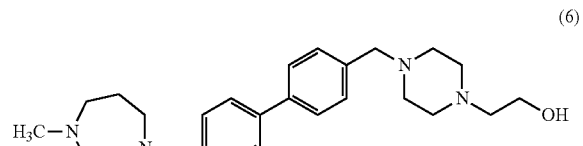
(6)

wherein the amine $HNR^{10}R^{11}$ used for Reaction 2 was 1-(2-hydroxyethyl)piperazine.

Example 7

4-((4-methyl-1,4-diazepan-1-yl)methyl)-4'-((3-oxopiperazin-1-yl)methyl)-[1,1'-biphenyl]-2-carbonitrile

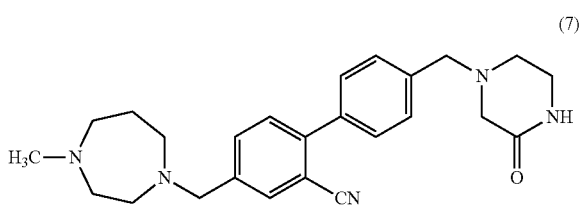 [SMILES: CN1CCCN(Cc2ccc(-c3ccc(CN4CCNC(=O)C4)cc3)c(C#N)c2)CC1]
(7)

wherein the amine $HNR^{10}R^{11}$ used for Reaction 2 was piperazin-2-one.

Example 8

4'-(((2-hydroxyethyl)(methyl)amino)methyl)-4-((4-methyl-1,4-diazepan-1-yl)methyl)-[1,1'-biphenyl]-2-carbonitrile

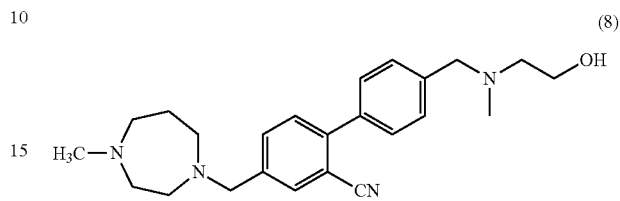
(8)

wherein the amine $HNR^{10}R^{11}$ used for Reaction 2 was 2-(methylamino)ethanol.

Example 9

4-((4-methyl-1,4-diazepan-1-yl)methyl)-4'-(morpholinomethyl)-[1,1'-biphenyl]-2-carbonitrile

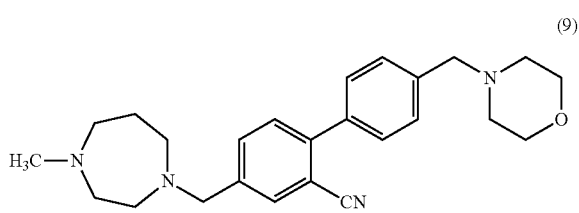 [SMILES: CN1CCCN(Cc2ccc(-c3ccc(CN4CCOCC4)cc3)c(C#N)c2)CC1]
(9)

wherein the amine $HNR^{10}R^{11}$ used for Reaction 2 was morpholine.

Example 10 tert-butyl(2-(((2'-cyano-4'-((4-methyl-1,4-diazepan-1-yl)methyl)-[1,1'-biphenyl]-4-yl)methyl)amino)ethyl)carbamate

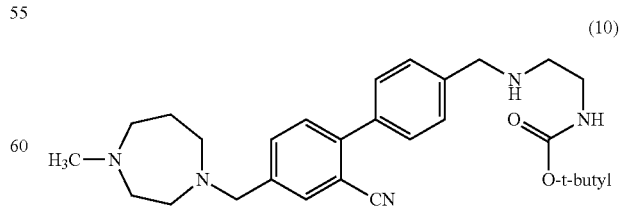
(10)

wherein the amine $HNR^{10}R^{11}$ used for Reaction 2 was tert-butyl(2-aminoethyl)carbamate.

Example 11

4-((4-methyl-1,4-diazepan-1-yl)methyl)-4'-((4-methylpiperazin-1-yl)methyl)-[1,1'-biphenyl]-2-carbonitrile

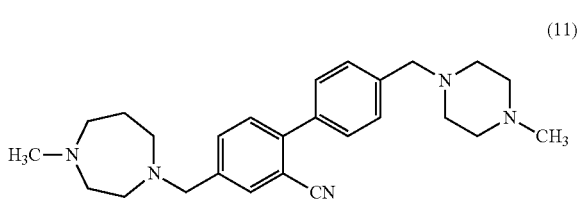
(11)

wherein the amine $HNR^{10}R^{11}$ used for Reaction 2 was 1-methylpiperazine.

Example 12

4'-((dimethylamino)methyl)-4-((4-methyl-1,4-diazepan-1-yl)methyl)-[1,1'-biphenyl]-2-carbonitrile

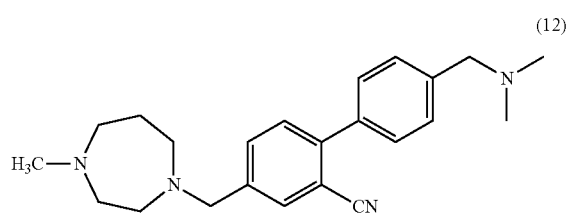
(12)

wherein the amine $HNR^{10}R^{11}$ used for Reaction 2 was dimethylamine.

Example 13

4-((4-methyl-1,4-diazepan-1-yl)methyl)-4'-(piperidin-1-ylmethyl)-[1,1'-biphenyl]-2-carbonitrile

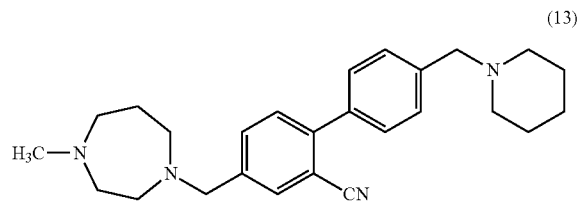 [SMILES: CN1CCCN(Cc2ccc(-c3ccc(CN4CCCCC4)cc3)c(C#N)c2)CC1]
(13)

wherein the amine $HNR^{10}R^{11}$ used for Reaction 2 was piperidine.

Example 14

4,4'-bis((4-methyl-1,4-diazepan-1-yl)methyl)-[1,1'-biphenyl]-2-carbonitrile

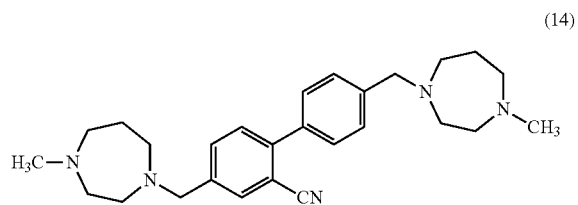
(14)

wherein the amine $HNR^{10}R^{11}$ used for Reaction 2 was 1-methylhomopiperazine. This compound may also be prepared by reacting 1-methylhomopiperazine with 4-(bromomethyl)phenylboronic acid pinacol ester at room temperature and coupling the reaction product with 2-bromo-5-((4-methyl-1,4-diazepan-1-yl)methyl)benzonitrile.

Example 15

4'-((4-(diethylamino)piperidin-1-yl)methyl)-4-((4-methyl-1,4-diazepan-1-yl)methyl)-[1,1'-biphenyl]-2-carbonitrile

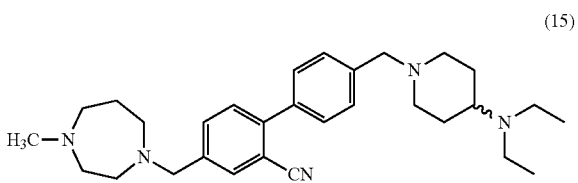 [SMILES: CCN(CC)C1CCN(Cc2ccc(-c3ccc(CN4CCCN(C)CC4)cc3C#N)cc2)CC1]
(15)

wherein the amine $HNR^{10}R^{11}$ used for Reaction 2 was 4-(diethylamino)piperidine.

Example 16

4'-(aminomethyl)-4-((4-methyl-1,4-diazepan-1-yl)methyl)-[1,1'-biphenyl]-2-carbonitrile

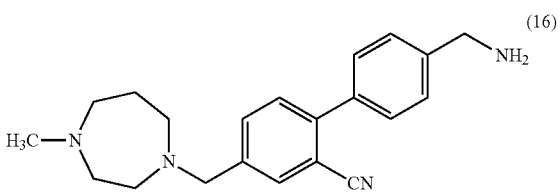 [SMILES: CN1CCCN(Cc2ccc(-c3ccc(CN)cc3)c(C#N)c2)CC1]
(16)

wherein the amine $HNR^{10}R^{11}$ used for Reaction 2 was ammonia.

The following exemplary compounds, provided in Examples 17-36, may be synthesized by the coupling Reaction 1 followed by the amidation Reaction 3 in accordance with Scheme I, wherein Ring T is 4-methylhomopiperazine, Ring A and Ring B are phenyl, Y=OCH$_3$, and $L^1$ is methylene:

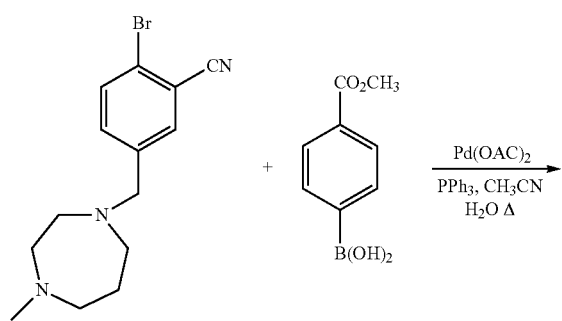

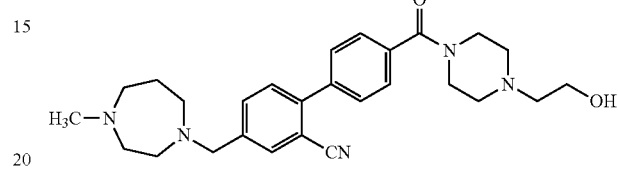

Example 17

2'-cyano-N-(2-hydroxyethyl)-N-methyl-4'-((4-methyl-1,4-diazepan-1-yl)methyl)-[1,1'-biphenyl]-4-carboxamide (17)

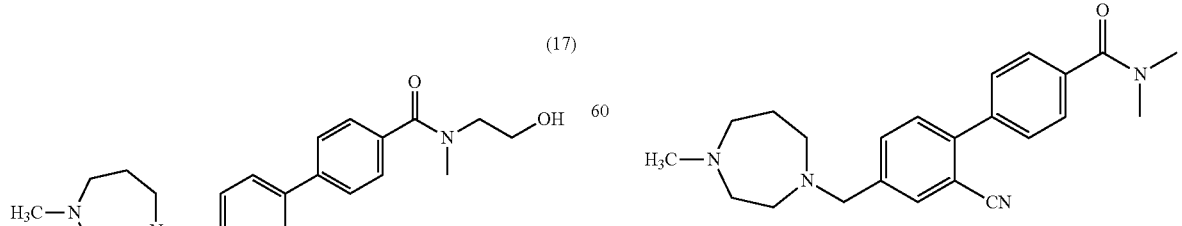

wherein the amine HNR$^{10}$R$^{11}$ used for Reaction 3 was 2-(methylamino)ethanol.

Example 18

4'-(4-(2-hydroxyethyl)piperazine-1-carbonyl)-4-((4-methyl-1,4-diazepan-1-yl)methyl)-[1,1'-biphenyl]-2-carbonitrile (18)

wherein the amine HNR$^{10}$R$^{11}$ used for Reaction 3 was 1-(2-hydroxyethyl)piperazine.

Example 19

4'-(4-hydroxypiperidine-1-carbonyl)-4-((4-methyl-1,4-diazepan-1-yl)methyl)-[1,1'-biphenyl]-2-carbonitrile (19)

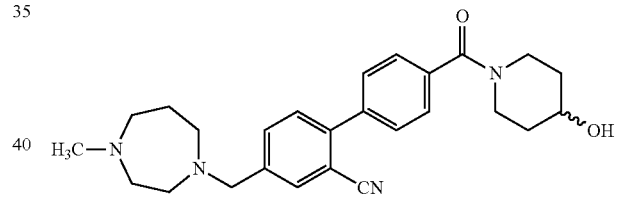

wherein the amine HNR$^{10}$R$^{11}$ used for Reaction 3 was 4-hydroxypiperidine.

Example 20

2'-cyano-N,N-dimethyl-4'-((4-methyl-1,4-diazepan-1-yl)methyl)-[1,1'-biphenyl]-4-carboxamide (20)

wherein the amine HNR$^{10}$R$^{11}$ used for Reaction 3 was dimethylamine.

Example 21

4'-(4-(2-methoxyethyl)piperazine-1-carbonyl)-4-((4-methyl-1,4-diazepan-1-yl)methyl)-[1,1'-biphenyl]-2-carbonitrile (21)

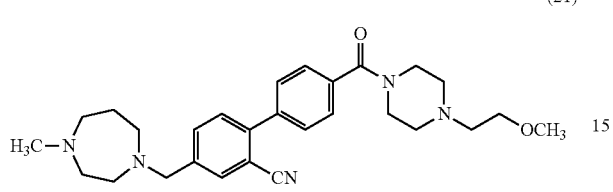

wherein the amine $HNR^{10}R^{11}$ used for Reaction 3 was 1-(2-methoxyethyl)piperazine.

Example 22

4'-(3-(hydroxymethyl)pyrrolidine-1-carbonyl)-4-((4-methyl-1,4-diazepan-1-yl)methyl)-[1,1'-biphenyl]-2-carbonitrile (22)

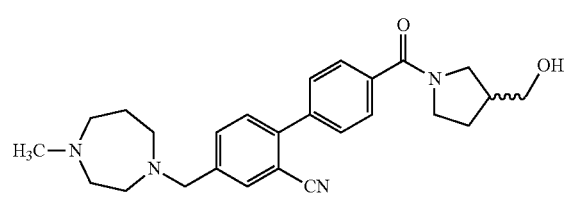

wherein the amine $HNR^{10}R^{11}$ used for Reaction 3 was 3-(hydroxymethyl)pyrrolidine.

Example 23

4'-(3-hydroxypiperidine-1-carbonyl)-4-((4-methyl-1,4-diazepan-1-yl)methyl)-[1,1'-biphenyl]-2-carbonitrile (23)

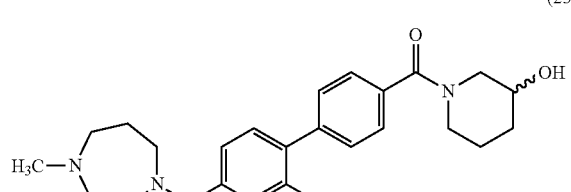

wherein the amine $HNR^{10}R^{11}$ used for Reaction 3 was 3-hydroxypiperidine.

Example 24

4-((4-methyl-1,4-diazepan-1-yl)methyl)-4'-(4-methylpiperazine-1-carbonyl)-[1,1'-biphenyl]-2-carbonitrile (24)

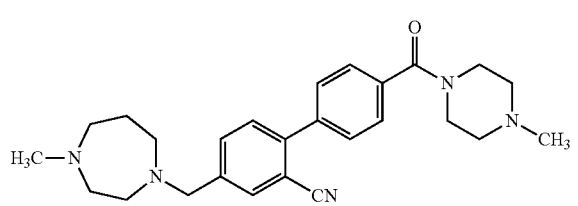

wherein the amine $HNR^{10}R^{11}$ used for Reaction 3 was 1-methylpiperazine.

Example 25

4'-(3-hydroxypyrrolidine-1-carbonyl)-4-((4-methyl-1,4-diazepan-1-yl)methyl)-[1,1'-biphenyl]-2-carbonitrile (25)

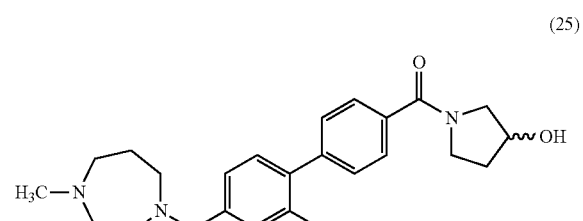

wherein the amine $HNR^{10}R^{11}$ used for Reaction 3 was 3-hydroxypyrrolidine.

Example 26

4-((4-methyl-1,4-diazepan-1-yl)methyl)-4'-(pyrrolidine-1-carbonyl)-[1,1'-biphenyl]-2-carbonitrile (26)

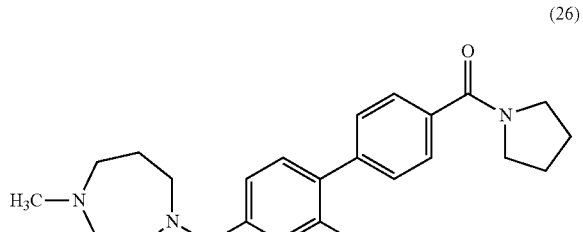

wherein the amine $HNR^{10}R^{11}$ used for Reaction 3 was pyrrolidine.

Example 27

2'-cyano-N,N-diethyl-4'-((4-methyl-1,4-diazepan-1-yl)methyl)-[1,1'-biphenyl]-4-carboxamide

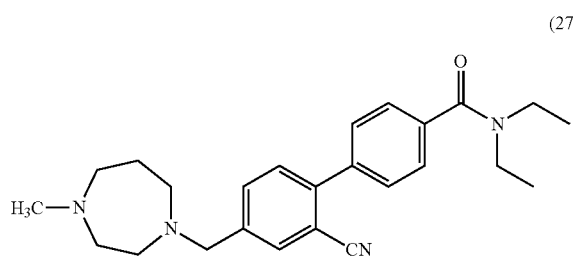
(27)

wherein the amine $HNR^{10}R^{11}$ used for Reaction 3 was diethylamine.

Example 28

2'-cyano-4'-((4-methyl-1,4-diazepan-1-yl)methyl)-[1,1'-biphenyl]-4-carboxamide

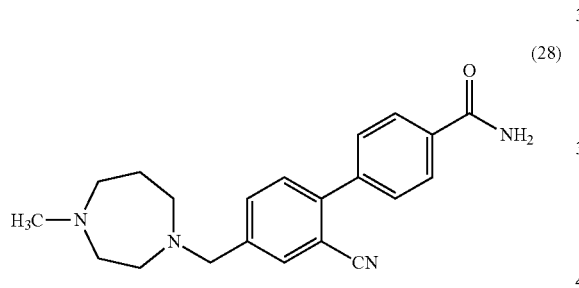
(28)

wherein the amine $HNR^{10}R^{11}$ used for Reaction 3 was ammonia.

Example 29

2'-cyano-N-methyl-4'-((4-methyl-1,4-diazepan-yl)methyl)-[1,1'-biphenyl]-4-carboxamide

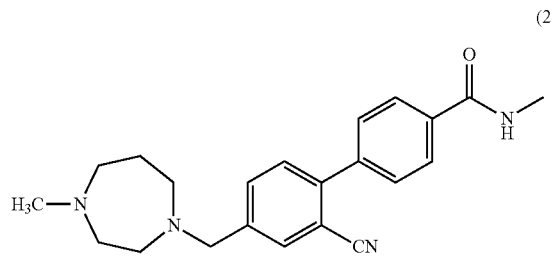
(29)

wherein the amine $HNR^{10}R^{11}$ used for Reaction 3 was methylamine.

Example 30

2'-cyano-N-(3-(dimethylamino)propyl)-4'-((4-methyl-1,4-diazepan-1-yl)methyl)-[1,1'-biphenyl]-4-carboxamide

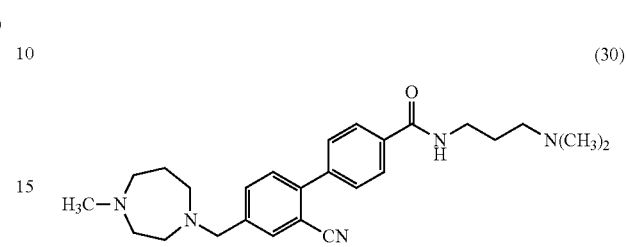
(30)

wherein the amine $HNR^{10}R^{11}$ used for Reaction 3 was $N^1,N^1$-dimethylpropane-1,3-diamine.

Example 31

4-((4-methyl-1,4-diazepan-1-yl)methyl)-4'-(4-oxopiperidine-1-carbonyl)-[1,1'-biphenyl]-2-carbonitrile

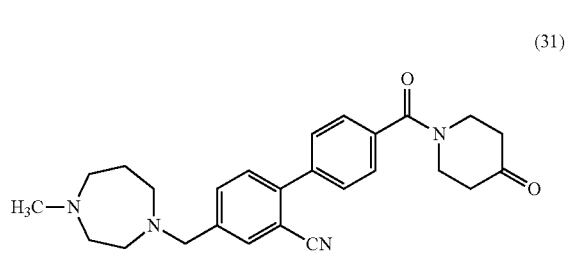 [SMILES: CN1CCCN(Cc2ccc(-c3ccc(C(=O)N4CCC(=O)CC4)cc3)c(C#N)c2)CC1]
(31)

wherein the amine $HNR^{10}R^{11}$ used for Reaction 3 was piperidin-4-one.

Example 32

2'-cyano-N-cyclopropyl-4'-((4-methyl-1,4-diazepan-1-yl)methyl)-[1,1'-biphenyl]-4-carboxamide

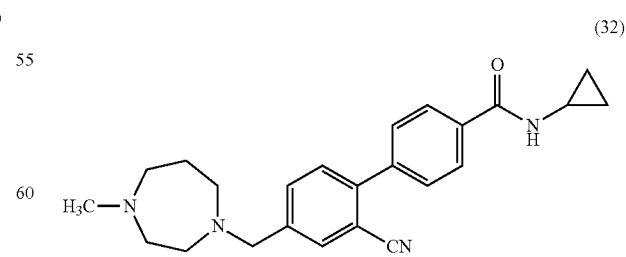
(32)

wherein the amine $HNR^{10}R^{11}$ used for Reaction 3 was cyclopropylamine.

Example 33

4-((4-methyl-1,4-diazepan-1-yl)methyl)-4'-(4-methyl-1,4-diazepane-1-carbonyl)-[1,1'-biphenyl]-2-carbonitrile

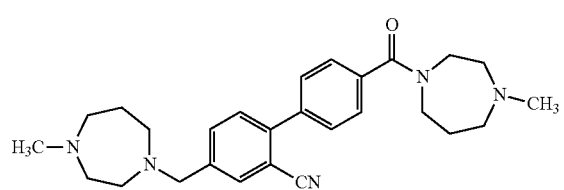
(33)

wherein the amine HNR$^{10}$R$^{11}$ used for Reaction 3 was 1-methylhomopiperazine.

Example 34

4-((4-methyl-1,4-diazepan-1-yl)methyl)-4'-(piperidine-1-carbonyl)-[1,1'-biphenyl]-2-carbonitrile

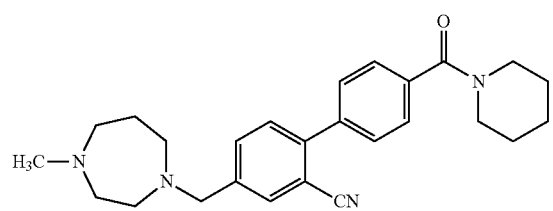
(34)

wherein the amine HNR$^{10}$R$^{11}$ used for Reaction 3 was piperidine.

Example 35

2'-cyano-N-methoxy-N-methyl-4'-((4-methyl-1,4-diazepan-1-yl)methyl)-[1,1'-biphenyl]-4-carboxamide

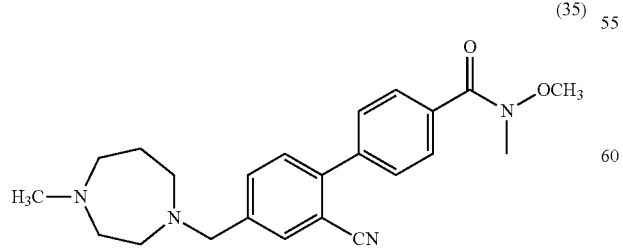
(35)

wherein the amine HNR$^{10}$R$^{11}$ used for Reaction 3 was N,O-dimethylhydroxylamine.

Example 36

4-((4-methyl-1,4-diazepan-1-yl)methyl)-4'-(morpholine-4-carbonyl)-[1,1'-biphenyl]-2-carbonitrile

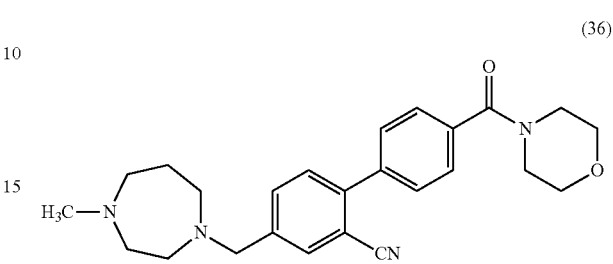
(36)

wherein the amine HNR$^{10}$R$^{11}$ used for Reaction 3 was morpholine.

In various embodiments, compounds of the present invention may be prepared as outlined in Scheme II below, supplemented and/or modified with any necessary methods known to those skilled in the art:

Scheme II:

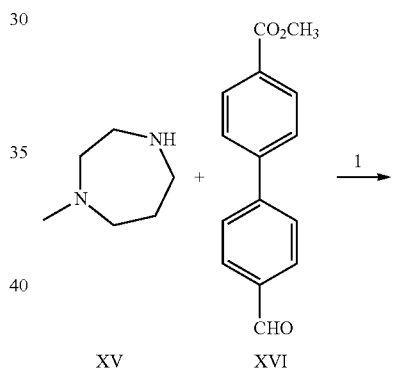

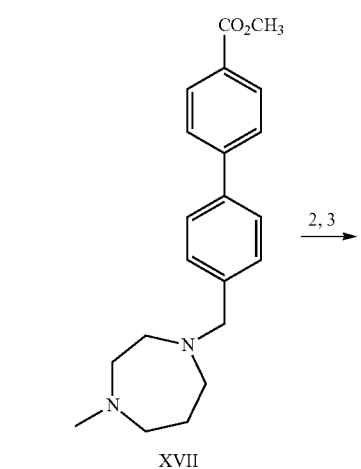

63

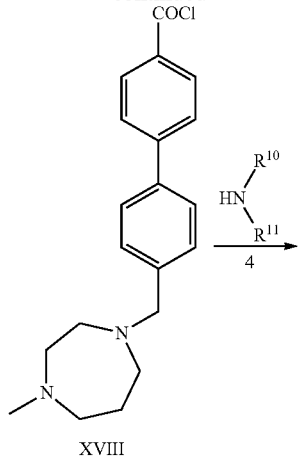

XVIII

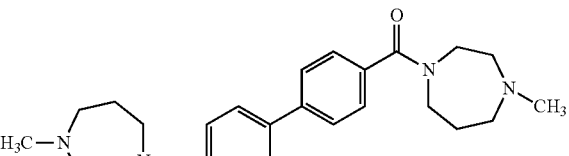

XIX

Scheme II is suitable for the preparation of compounds wherein both Ring A and Ring B are phenyl and directly bonded together, ($L^2$ in structural formula I above is a covalent bond). Scheme II may also be used to prepare compounds wherein Ring A is devoid of substitution. For Scheme II, $R^{10}$ and $R^{11}$ are the same as defined for Scheme I above.

Scheme II begins with Reaction 1, a reductive amination reaction between 1-methylhomopiperazine XV and 4'-formylbiphenyl-4-carboxylic acid methyl ester XVI with sodium triethoxyborohydride and molecular sieves in DCM. After 5 hours at room temperature, the mixture is diluted with aqueous sodium bicarbonate and extracted with DCM. After evaporation of volatiles, the ester XVII may be purified by column chromatography. Reactions 2 and 3 of Scheme II comprise alkaline hydrolysis of the ester to the carboxylic acid and conversion of the carboxylic acid to the acyl chloride using thionyl chloride. Reaction 4 comprises the reaction of the acyl chloride XVIII with an amine $HNR^{10}R^{11}$ in the presence of triethylamine at room temperature. After removal of volatiles, the amide XIX may be purified by thin layer chromatography.

The following exemplary compounds, provided in Examples 37-39, may be synthesized by reaction of acyl chloride XVIII with various amines in accordance with Scheme II:

64

Example 37

(4-methyl-1,4-diazepan-1-yl)(4'-((4-methyl-1,4-diazepan-1-yl)methyl)-[1,1'-biphenyl]-4-yl)methanone

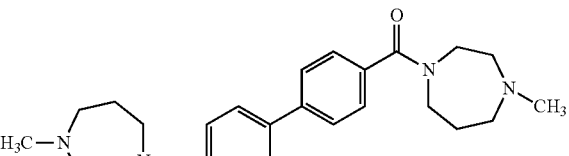

(37)

wherein the amine $HNR^{10}R^{11}$ used for Reaction 4 in Scheme II was 1-methylhomopiperazine.

Example 38

1-(4-(4'-((4-methyl-1,4-diazepan-1-yl)methyl)-[1,1'-biphenyl]-4-carbonyl)piperazin-1-yl)ethanone

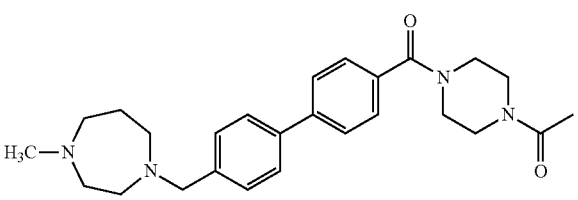

(38)

wherein the amine $HNR^{10}R^{11}$ used for Reaction 4 in Scheme II was 1-acetylpiperazine.

Example 39

(4'-((4-methyl-1,4-diazepan-1-yl)methyl)-[1,1'-biphenyl]-4-yl)(4-morpholinopiperidin-1-yl)methanone

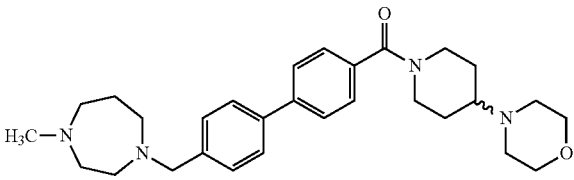

(39)

wherein the amine $HNR^{10}R^{11}$ used for Reaction 4 in Scheme II was 4-(piperidin-4-yl)morpholine.

In various embodiments, compounds of the present invention may be prepared as outlined in Scheme III below, supplemented and/or modified with any necessary methods known to those skilled in the art.

Scheme III:

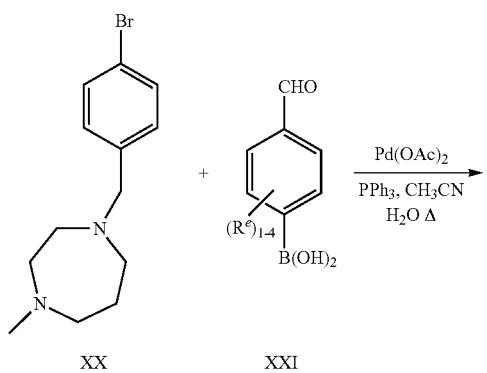

XX      XXI

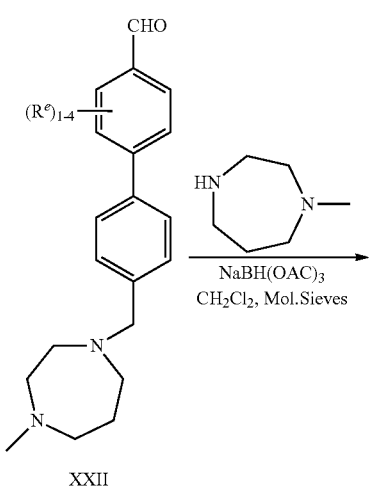

XXIII

Scheme III is suitable for the preparation of compounds wherein both Ring A and Ring B are phenyl and directly bonded together, ($L^2$ in structural formula I above is a covalent bond), and where Ring A is substituted with one or more halogens and Ring B is devoid of substitution.

Scheme III begins with a coupling reaction between 1-(4-bromobenzyl)-4-methyl-1,4-diazepane XX and a 4-formylphenylboronic acid XXI that is substituted with 1-4 $R^e$ groups using palladium acetate, triphenylphosphine and potassium carbonate in aqueous acetonitrile. Following a brief heating the reaction mixture may be extracted with DCM and the reaction product XXII purified by thin layer chromatography (e.g. DCM/methanol solvent). The second reaction of Scheme III is a reductive amination reaction of intermediate XXII and 1-methylhomopiperiazine with sodium triacetoxyborohydride and molecular sieves in DCM. The reaction mixture is diluted with aqueous sodium bicarbonate and extracted with DCM to give the crude product XXIII. The amines XXIII XIII may be purified by thin layer chromatography.

The following exemplary compounds, provided in Examples 40-44, may be synthesized by using various substituted phenylboronic acids XXI in accordance with Scheme III:

Example 40

4,4'-((3,5-difluoro-[1,1'-biphenyl]-4,4'-diyl)bis(methylene))bis(1-methyl-1,4-diazepane)

(40)

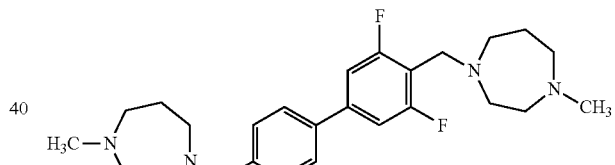

wherein the phenylboronic acid XXI used in Scheme III was (3,5-difluoro-4-formylphenyl)boronic acid.

Example 41

4,4'-((2,3-difluoro-[1,1'-biphenyl]-4,4'-diyl)bis(methylene))bis(1-methyl-1,4-diazepane)

(41)

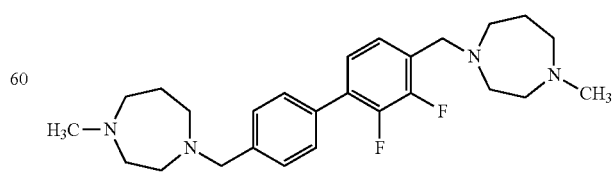

wherein the phenylboronic acid XXI used in Scheme III was (2,3-difluoro-4-formylphenyl)boronic acid.

Example 42

4,4'-((3-fluoro-[1,1'-biphenyl]-4,4'-diyl)bis(methylene))bis(1-methyl-1,4-diazepane)

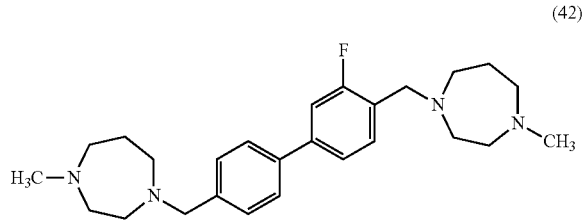
(42)

wherein the phenylboronic acid XXI used in Scheme III was (3-fluoro-4-formylphenyl)boronic acid.

Example 43

4,4'-((3-chloro-[1,1'-biphenyl]-4,4'-diyl)bis(methylene))bis(1-methyl-1,4-diazepane)

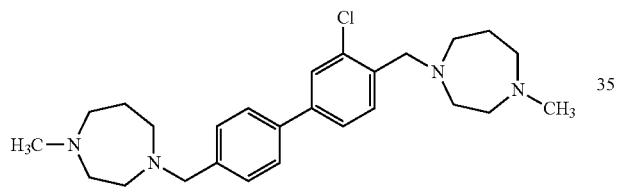
(43)

wherein the phenylboronic acid XXI used in Scheme III was (3-chloro-4-formylphenyl)boronic acid.

Example 44

4,4'-((2-fluoro-[1,1'-biphenyl]-4,4'-diyl)bis(methylene))bis(1-methyl-1,4-diazepane)

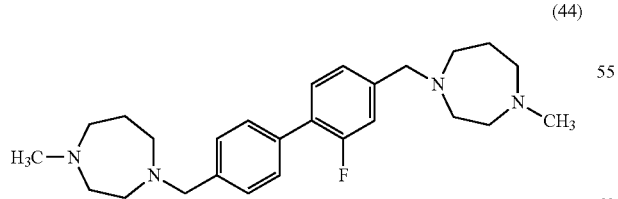
(44)

wherein the phenylboronic acid XXI used in Scheme III was (2-fluoro-4-formylphenyl)boronic acid.

In various embodiments, compounds of the present invention may be prepared as indicated below:

Example 45

4,4'-bis((4-methyl-1,4-diazepan-1-yl)methyl)-1,1'-biphenyl

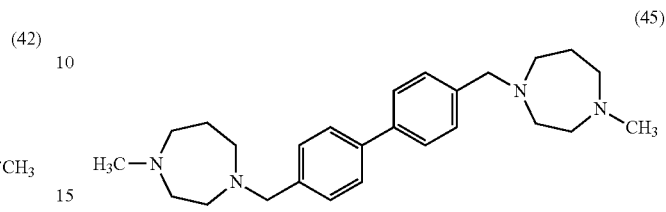
(45)

may be prepared by treating a mixture of 4,4'-biphenyldialdehyde and 1-methylhomopiperazine with sodium triacetoxyborohydride in DCM. The mixture was diluted with aqueous sodium bicarbonate and extracted with DCM. After removal of volatiles the product may be purified by thin layer chromatography.

Example 46

N-((2'-cyano-4'-((4-methyl-1,4-diazepan-1-yl)methyl)-[1,1'-biphenyl]-4-yl)methyl)-P,P-dimethylphosphinic amide

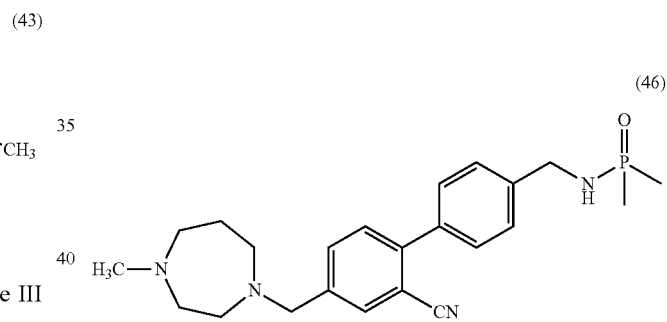
(46)

may be prepared by reacting 4'-(aminomethyl)-4-((4-methyl-1,4-diazepan-1-yl)methyl)-[1,1'-biphenyl]-2-carbonitrile, (Example 16), with dimethylphosphoryl chloride, $(CH_3)_2P(O)Cl$.

Example 47

1-((2'-cyano-4'-((4-methyl-1,4-diazepan-1-yl)methyl)-[1,1'-biphenyl]-4-yl)methyl)-3-methylurea

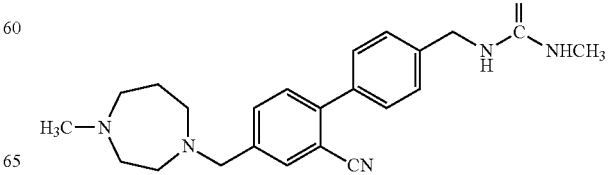
(47)

may be prepared by reacting 4'-(aminomethyl)-4-((4-methyl-1,4-diazepan-1-yl)methyl)-[1,1'-biphenyl]-2-carbonitrile, (Example 16), with N-methyl carbamoyl chloride, CH₃NHC(O)Cl.

Example 48

N-((2'-cyano-4'-((4-methyl-1,4-diazepan-1-yl)methyl)-[1,1'-biphenyl]-4-yl)methyl)methanesulfonamide

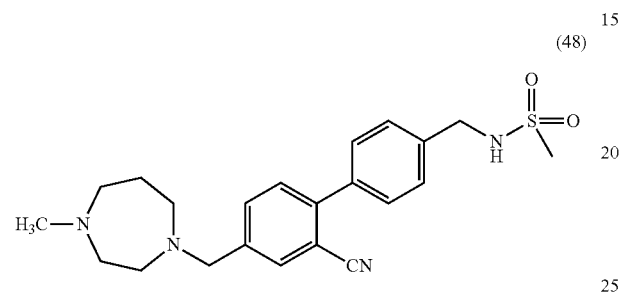
(48)

may be prepared by reacting 4'-(aminomethyl)-4-((4-methyl-1,4-diazepan-1-yl)methyl)-[1,1'-biphenyl]-2-carbonitrile, (Example 16), with methanesulfonyl chloride, CH₃SO₂Cl.

In various embodiments, compounds of the present invention may be prepared in accordance with Scheme IV below:

Scheme IV:

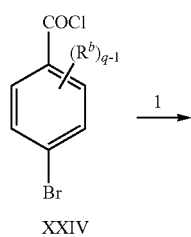
XXIV

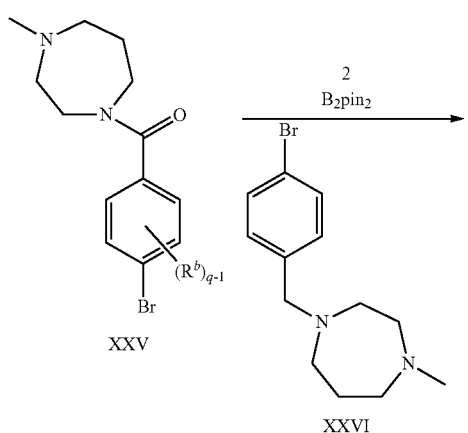
XXV

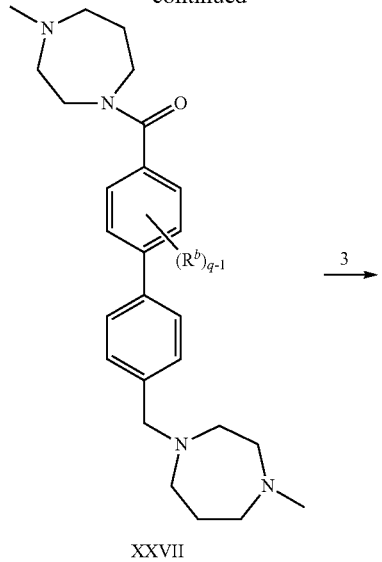
XXVII

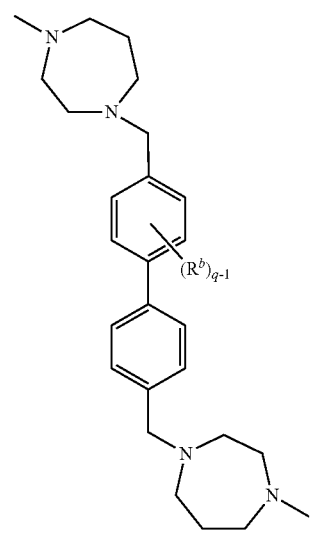
XXVIII

Scheme IV is suitable for the preparation of compounds where both Ring A and Ring B form a biphenyl system and only one of the rings, Ring B, carries any substitution. Scheme IV also finds use in preparing compounds of the present invention where any $R^b$ is alkyl.

Scheme IV begins with Reaction 1, the acylation of a para-bromo acylchloride XXIV with 1-methylhomopiperazine. The resulting amide XXV is then coupled in Reaction 2 with 1-(4-bromobenzyl)-4-methylhomopiperazine XXVI using diboron pinacol ester, B₂pic₂. Lastly in Reaction 3, the resulting biphenyl XXVII may be treated with lithium aluminum hydride in dioxane to produce XXVIII.

The following exemplary compounds, provided in Examples 49 and 50, may be synthesized by using a substituted bromobenzoylchloride XXIV in accordance with Scheme IV:

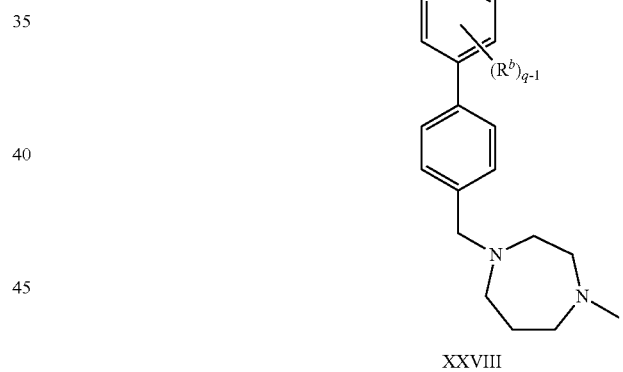
XXVI

Example 49

4,4'-((2-methyl-[1,1'-biphenyl]-4,4'-diyl)bis(methylene))bis(1-methyl-1,4-diazepane)

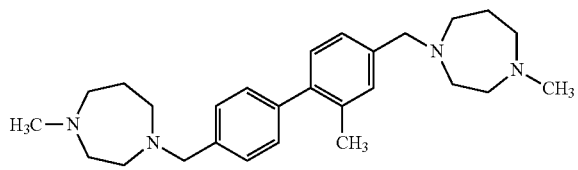
(49)

may be prepared in accordance with Scheme IV beginning with 4-bromo-3-methylbenzoyl chloride as compound XXIV.

Example 50

(4-methyl-1,4-diazepan-1-yl)(2-methyl-4'-((4-methyl-1,4-diazepan-1-yl)methyl)-[1,1'-biphenyl]-4-yl)methanone

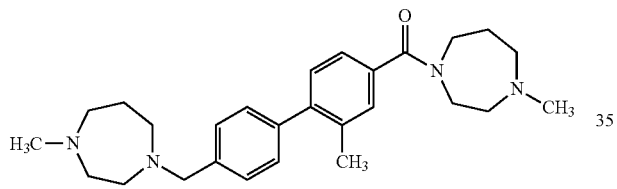
(50)

may be prepared in accordance with Scheme IV, beginning with 4-bromo-3-methylbenzoyl chloride as compound XXIV but omitting the Reaction 3 (the LAH reduction).

In another embodiment, an intermediate from Scheme IV may be converted to a compound of the present invention.

Example 51

(2'-methyl-4'-((4-methyl-1,4-diazepan-1-yl)methyl)-[1,1'-biphenyl]-4-yl)methanol

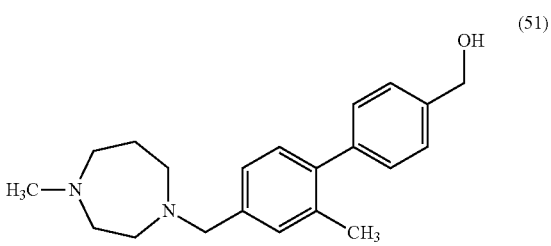 [SMILES: Cc1cc(CN2CCCN(C)CC2)ccc1-c1ccc(CO)cc1]
(51)

may be synthesized from (4-bromo-3-methylphenyl)(4-methyl-1,4-diazepan-1-yl)methanone (XXV) by first coupling XXV with 4-formylphenylboronic acid (XXI of Scheme III, without $R^e$ substitution) using palladium acetate, triphenylphosphine and potassium carbonate in aqueous acetonitrile. The resulting biphenyl aldehyde is then reduced with lithium aluminum hydride in dioxane to produce Example 51.

In various embodiments, exemplary compounds discussed above, or derivatives or precursors thereof, may be converted to other compounds in accordance with the present invention. The following exemplary compounds, provided in Examples 52-57, may be prepared by using the various synthetic methods indicated:

Example 52

(4,4'-bis((4-methyl-1,4-diazepan-1-yl)methyl)-[1,1'-biphenyl]-2-yl)methanamine

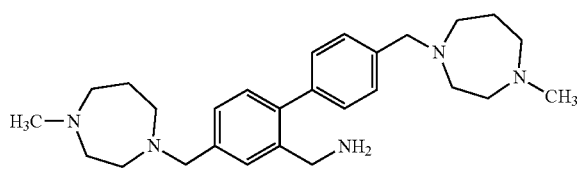
(52)

may be prepared by treating 4,4'-bis((4-methyl-1,4-diazepan-1-yl)methyl)-[1,1'-biphenyl]-2-carbonitrile, Example 14, with lithium aluminum hydride.

Example 53

N-((4,4'-bis((4-methyl-1,4-diazepan-1-yl)methyl)-[1,1'-biphenyl]-2-yl)methyl)formamide

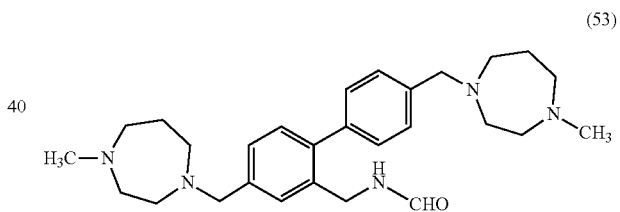
(53)

may be prepared by reacting (4,4'-bis((4-methyl-1,4-diazepan-1-yl)methyl)-[1,1'-biphenyl]-2-yl)methanamine (Example 52) with ethyl formate.

Example 54

4,4'-((3-methyl-[1,1'-biphenyl]-4,4'-diyl)bis(methylene))bis(1-methyl-1,4-diazepane)

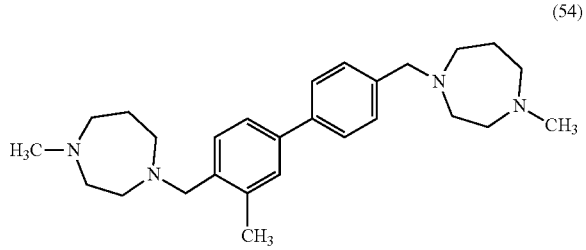
(54)

may be prepared by coupling 4-formyl-3-methylphenylboronic acid (XXI with $R^e$=CH$_3$) with intermediate XX to produce a biphenyl compound that is subsequently converted to Example 54 through reductive amination using 1-methylhomopiperazine and sodium triacetoxyborohydride.

Example 55

2'-fluoro-4,4'-bis((4-methyl-1,4-diazepan-1-yl)methyl)-[1,1'-biphenyl]-2-carbonitrile

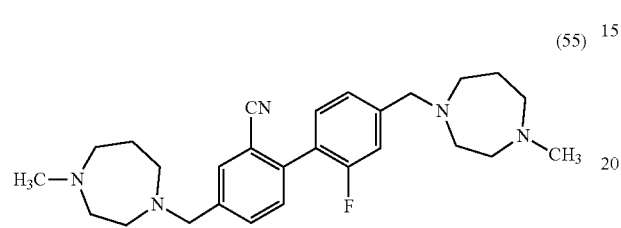

(55)

may be prepared by coupling 2-fluoro-4-formylphenylboronic acid (XXI with $R^e$=F) with 2-bromo-5-((4-methyl-1,4-diazepan-1-yl)methyl)benzonitrile to form and intermediate biphenyl that is subsequently treated with 1-methylhomopiperazine and sodium triacetoxyborohydride in a reductive amination reaction.

Example 56

4,4'-bis((4-methyl-1,4-diazepan-1-yl)methyl)-[1,1'-biphenyl]-2,2'-dicarbonitrile

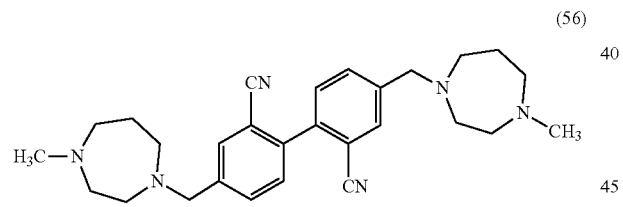

(56)

may be prepared by dimerization of 2-bromo-5-((4-methyl-1,4-diazepan-1-yl)methyl)benzonitrile in the presence of diboron pinacol ester, B$_2$pin$_2$.

Example 57

4,4'-((2-nitro-[1,1'-biphenyl]-4,4'-diyl)bis(methylene))bis(1-methyl-1,4-diazepane)

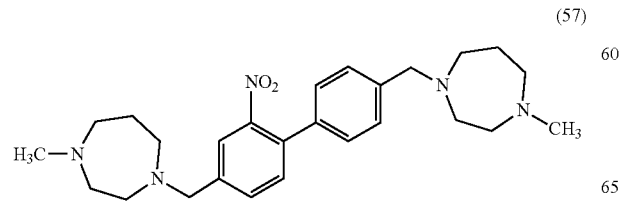

(57)

may be prepared by first subjecting 4-bromo-3-nitrobenzaldehyde to reductive amination with 1-methylhomopiperazine in the presence of triacetoxyborohydride, secondly coupling the reaction product with 4-formylphenylboronic acid, and lastly subjecting the reaction product to reductive amination with 1-methylhomopiperazine in the presence of triacetoxyborohydride.

In various embodiments, compounds of the present invention may be prepared in accordance with Scheme V below.

Scheme V:

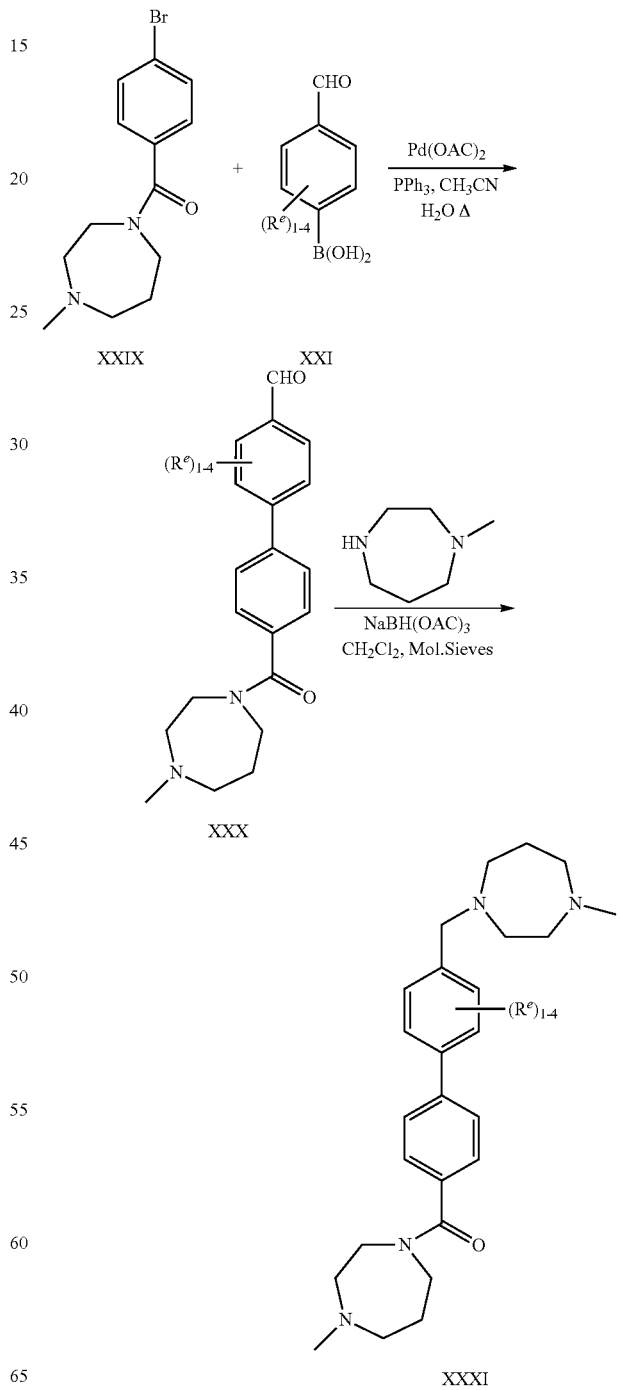

Scheme V is suitable for the preparation of compounds where both Ring A and Ring B form a biphenyl system and only one of the rings, Ring A, carries any substitution. Scheme V also finds use in preparing compounds XXXI of the present invention where any $R^e$ is halogen.

Scheme V begins with the formation of amide XXIX by reaction of 4-bromobenzoylchloride with 1-methylhomopiperazine. Amide XXIX is then coupled with a 4-formylphenylboronic acid XXI in the presence of palladium acetate and triphenylphosphine to form the biphenyl compound XXX. Lastly, intermediate XXX is treated with 2-methylhomopiperazine and sodium triacetoxyborohydride to form compound XXXI.

The following exemplary compound, Example 58, may be synthesized by using a substituted 4-formylphenylboronic acid XXI in accordance with Scheme V:

Example 58

(2'-fluoro-4'-((4-methyl-1,4-diazepan-1-yl)methyl)-[1,1'-biphenyl]-4-yl)(4-methyl-1,4-diazepan-1-yl)methanone

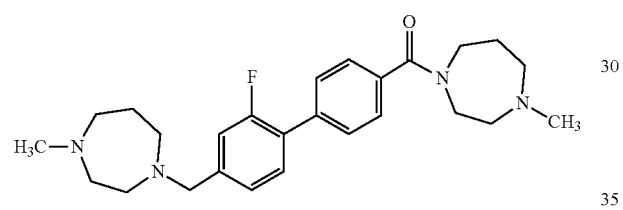

(58)

may be prepared using 2-fluoro-4-formylphenylboronic acid (XXI with $R^e$=F) in the coupling reaction.

In various embodiments, compounds XXXI of the present invention may also be prepared in accordance with Scheme VI below:

Scheme VI:

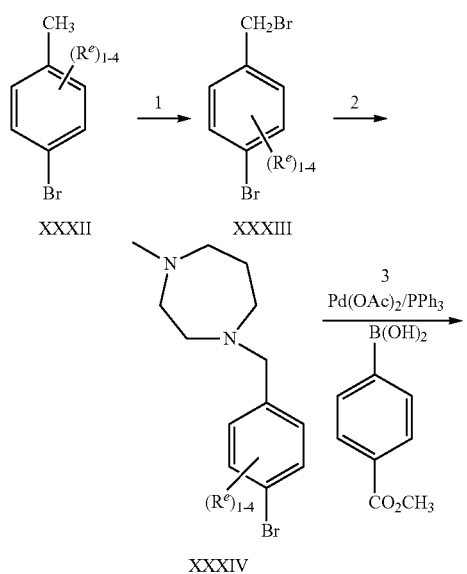

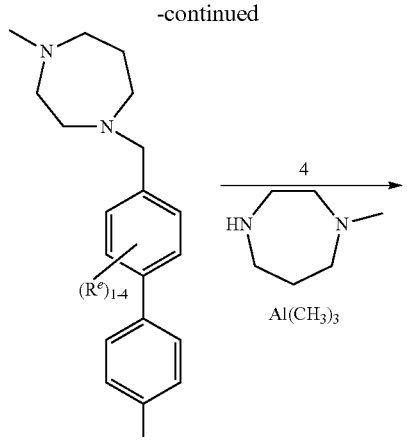

XXXV

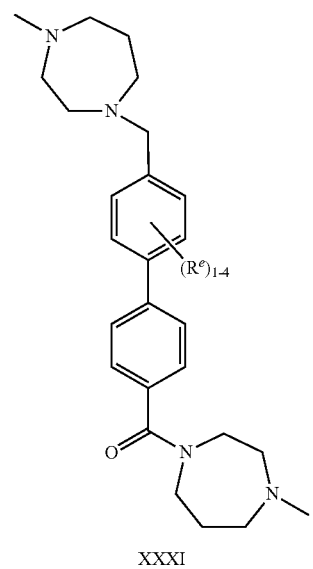

XXXI

Scheme VI is suitable for the preparation of compounds where both Ring A and Ring B form a biphenyl system and only one of the rings, Ring A, carries any substitution. Scheme V also finds use in preparing compounds XXXI of the present invention where any $R^e$ is a cyano group.

Scheme VI begins with the bromination Reaction 1 of a 4-bromotoluene XXXII with N-bromosuccinamide (NBS) and benzoyl peroxide in chloroform. The bromo compound XXXIII is then reacted with 1-methylhomopiperazine in Reaction 2 in DCM to give the bromobenzyldiazepan XXXIV. Intermediate XXXIV is then coupled with 4-methoxycarbonylphenylboronic acid in the presense of palladium diacetate and triphenylphosphine to give the biphenyl carboxylic acid ester XXXV, which is reacted with 1-methylhomopiperazine and trimethylaluminum to give compound XXXI.

The following exemplary compound, Example 33 (also discussed above), may be synthesized in accordance with Scheme VI beginning with 2-bromo-5-methylbenzonitrile XXXII:

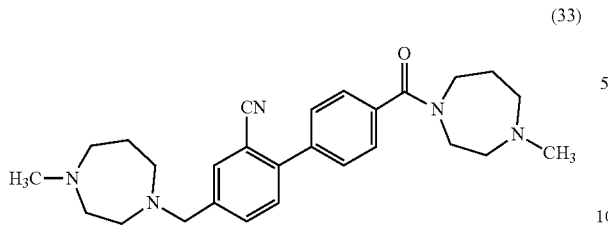

(33)

In various embodiments, compounds of the present invention may be prepared in accordance with Scheme VII:

Scheme VII:

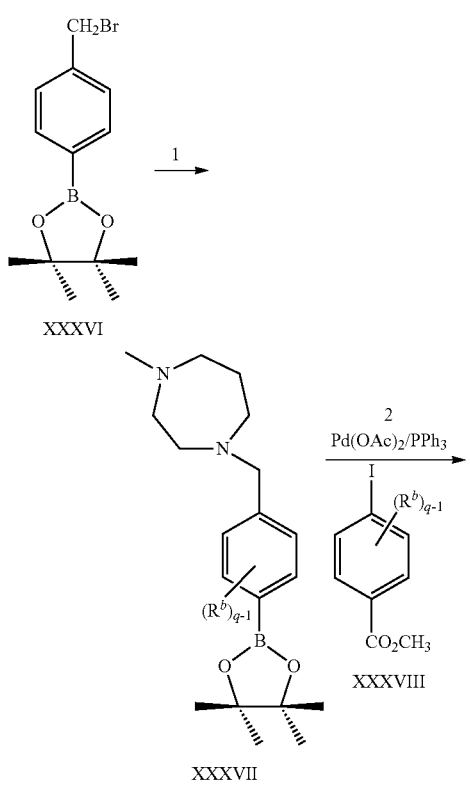

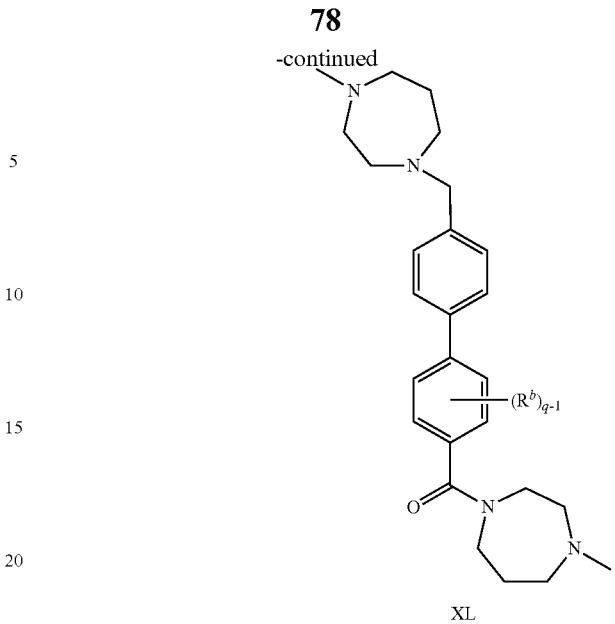

XL

Scheme VII is suitable for the preparation of compounds where both Ring A and Ring B form a biphenyl system and only one of the rings, Ring B, carries any substitution. Scheme VII also finds use in preparing compounds XL of the present invention where any $R^b$ is halogen.

Scheme VII begins with Reaction 1 between 4-bromomethylphenylboronic acid pinacol ester XXXVI and 1-methylhomopiperazine in acetonitrile to give the benzyldiazepan XXXVII. This intermediate is then coupled with a 4-iodobenzoic acid methyl ester XXXVIII in the presence of palladium diacetate and triphenylphosphine to give the biphenyl ester XXXIX. Intermediate XXXIX is then reacted with 1-methylhomopiperazine in DCE, in the presence of trimethylaluminum, to give the amide XL.

The following exemplary compound, provided in Example 59, may be prepared in accordance with Scheme VII.

Example 59

(2-fluoro-4'-((4-methyl-1,4-diazepan-1-yl)methyl)-[1,1'-biphenyl]-4-yl)(4-methyl-1,4-diazepan-1-yl)methanone

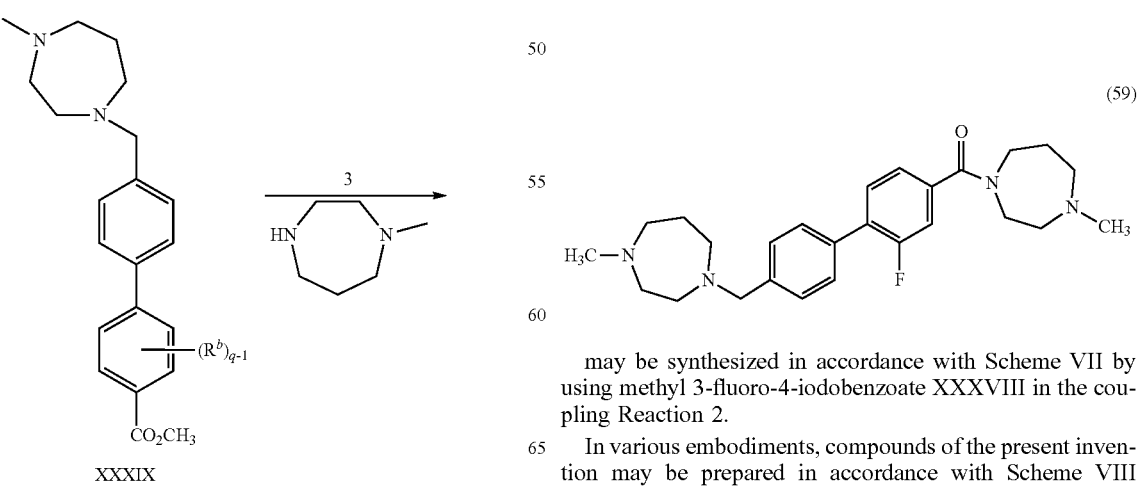

(59)

may be synthesized in accordance with Scheme VII by using methyl 3-fluoro-4-iodobenzoate XXXVIII in the coupling Reaction 2.

In various embodiments, compounds of the present invention may be prepared in accordance with Scheme VIII below:

Scheme VIII:

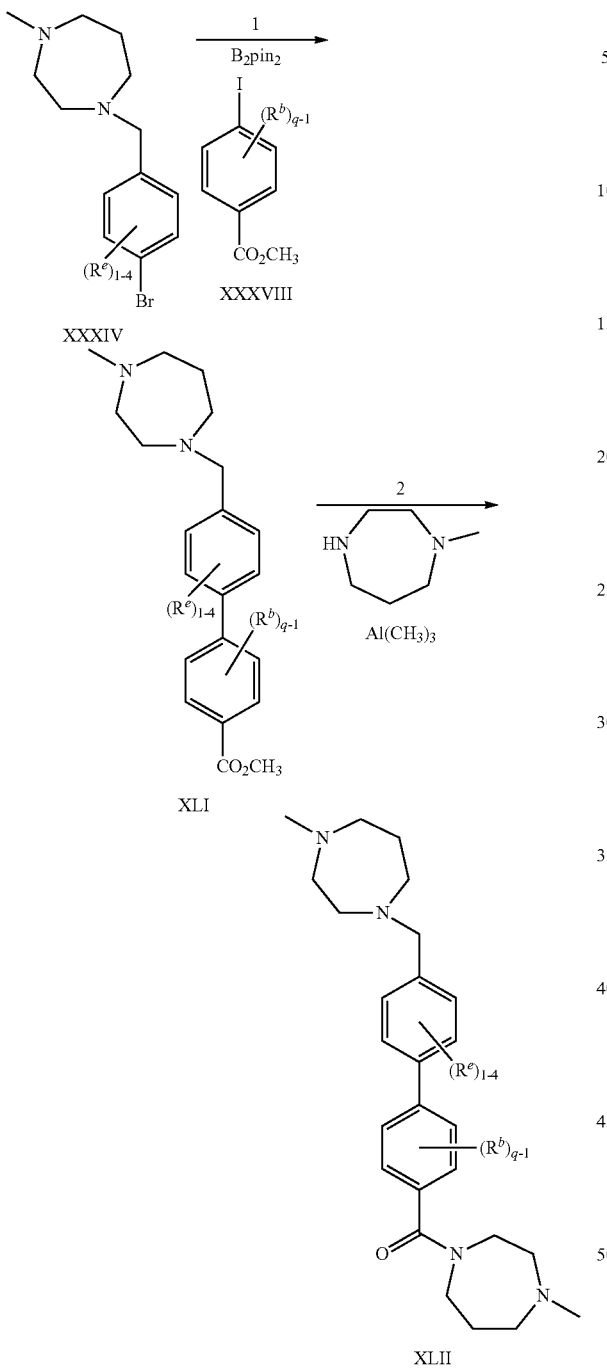

Scheme VIII is suitable for the preparation of compounds where both Ring A and Ring B form a biphenyl system and both Rings A and B are substituted. Scheme VIII also finds use in preparing compounds XLII of the present invention where any $R^b$ is halogen or alkyl, and any $R^e$ is a cyano group.

Scheme VIII begins with a substituted bromobenzyldiazepan XXXIV discussed above in the context of Scheme VI. In Scheme VIII, the bromobenzyldiazepan XXXIV is coupled with a substituted iodobenzoate ester XXXVIII (from Scheme VII) in the presence of diboron pinacol ester ($B_2pin_2$) to form the biphenyl ester XLI with substitution in both phenyl rings. The ester XLI is then reacted with 1-methylhomopiperazine in a direct amidation reaction to form the amide XLII. Trimethylaluminium may be used in the amidation reaction.

Depending on the particular substituents in the phenyl rings, Reaction 2 in Scheme VIII may be modified to a two-step sequence comprising: 1) prior alkaline hydrolysis of ester XLI to the biphenylcarboxylic acid; followed by, 2) reaction with 1-methylhomopiperazine in the presence of a peptide-coupling reagent such as O-(7-azabenzotriazole-1-yl)-N,N,N,N'-tetramethyluronium hexafluorophosphate (HATU) in diisopropylethylamine and DMF.

The following exemplary compounds, provided in Examples 60-61, may be synthesized by using a substituted benzyldiazepan XXXIV and a substituted 4-iodobenzoate ester XXXVIII in accordance with variations of Scheme VIII:

Example 60

2'-methyl-4-((4-methyl-1,4-diazepan-1-yl)methyl)-4'-(4-methyl-1,4-diazepane-1-carbonyl)-[1,1'-biphenyl]-2-carbonitrile (60)

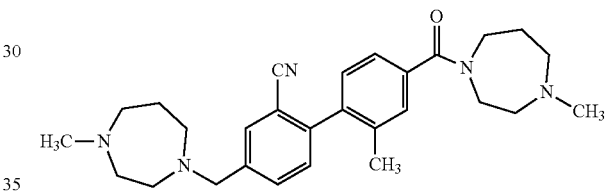

may be prepared from 2-bromo-5-((4-methyl-1,4-diazepan-1-yl)methylbenzonitrile and methyl 3-methyl-4-iodobenzoate in accordance with Scheme VIII.

Example 61

2'-bromo-4-((4-methyl-1,4-diazepan-1-yl)methyl)-4'-(4-methyl-1,4-diazepane-1-carbonyl)[1,1'-biphenyl]-2-carbonitrile (61)

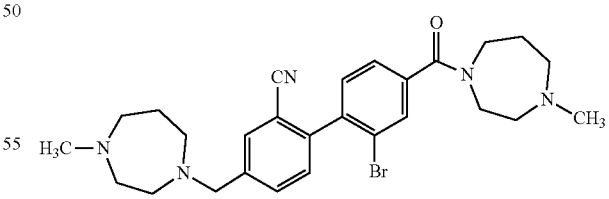

may be prepared from 2-bromo-5-((4-methyl-1,4-diazepan-1-yl)methylbenzonitrile and methyl 3-bromo-4-iodobenzoate in accordance with Scheme VIII, by using the two-step modification to Reaction 2 to preserve the aryl bromide substituent.

In various embodiments, exemplary compounds discussed above, or derivatives or precursors thereof, may be converted to other compounds in accordance with the present invention. The following exemplary compounds, provided in Examples 62-63, may be prepared by using the various synthetic methods indicated:

Example 62

2'-(dimethylamino)-4-((4-methyl-1,4-diazepan-1-yl)methyl)-4'-(4-methyl-1,4-diazepane-1-carbonyl)-[1,1'-biphenyl]-2-carbonitrile

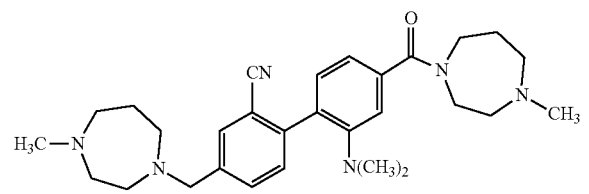
(62)

may be prepared by the palladium catalyzed amination of 2'-bromo-4-((4-methyl-1,4-diazepan-1-yl)methyl)-4'-(4-methyl-1,4-diazepane-1-carbonyl)-[1,1'-biphenyl]-2-carbonitrile, Example 61, with dimethylamine.

Example 63

4-((4-methyl-1,4-diazepan-1-yl)methyl)-4'-(4-methyl-1,4-diazepane-1-carbonyl)-[1,1'-biphenyl]-2,2'-dicarbonitrile

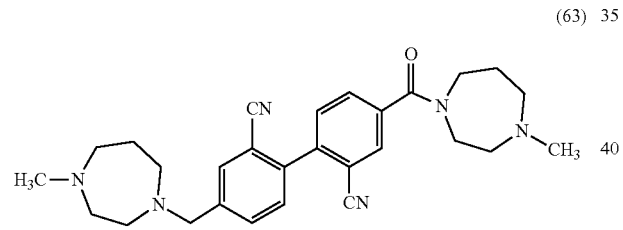
(63)

may be prepared by reacting 2'-bromo-4-((4-methyl-1,4-diazepan-1-yl)methyl)-4'-(4-methyl-1,4-diazepane-1-carbonyl)-[1,1'-biphenyl]-2-carbonitrile, Example 61, with CuCN in the presence of palladium diacetate, triphenylphosphine and potassium carbonate in DMF.

In various embodiments, compounds of the present invention may be prepared in accordance with Scheme IX below:

Scheme IX:

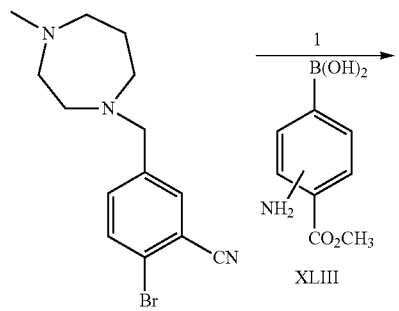

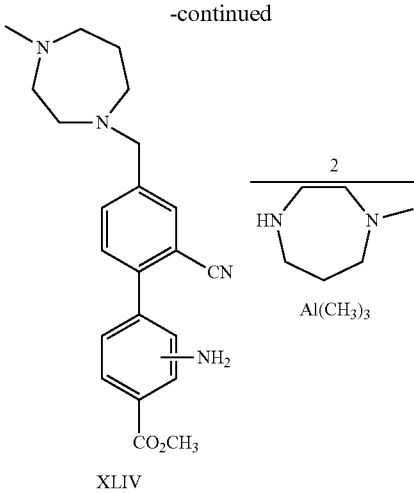

XLIV

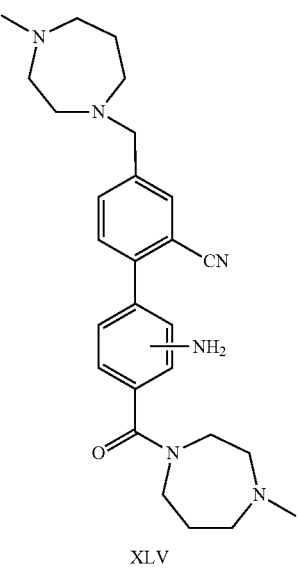

XLV

Scheme IX begins with a palladium catalyzed coupling reaction between 2-bromo-5-((4-methyl-1,4-diazepan-1-yl)methylbenzonitrile and an amino-4-methoxycarbonylphenylboronic acid XLIII to form the intermediate biphenyl ester XLIV. The ester XLIV is then reacted with 1-methylhomopiperazine in a direct amidation reaction catalyzed by trimethylaluminum to form compound XLV.

Example 64

2'-amino-4-((4-methyl-1,4-diazepan-1-yl)methyl)-4'-(4-methyl-1,4-diazepane-1-carbonyl)-[1,1'-biphenyl]-2-carbonitrile

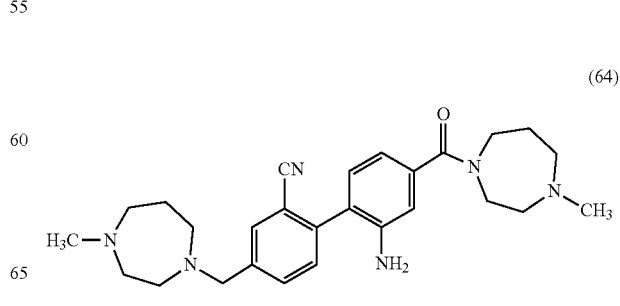
(64)

may be prepared in accordance with Scheme IX by using 2-amino-4-methoxycarbonylphenylboronic acid as the boronic acid XLIII.

In various embodiments, compounds of the present invention may be prepared in accordance with Scheme X below:

Scheme X:

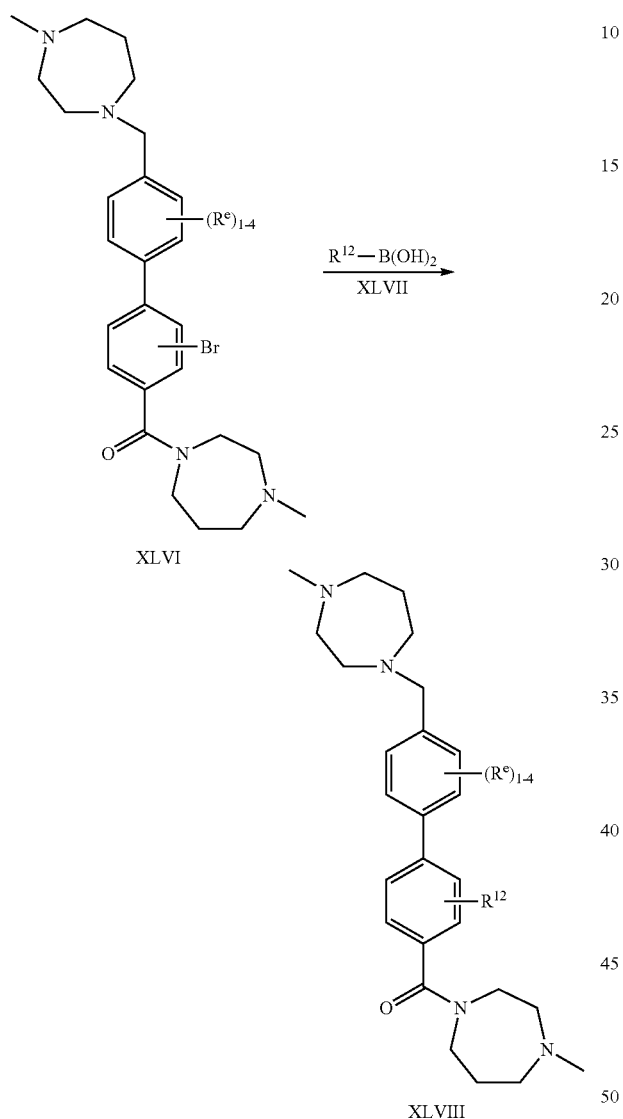

XLVI

XLVIII

Scheme X comprises the coupling reaction between a compound of the present invention XLVI, discussed in various embodiments above, and an aryl or heteroaryl boronic acid XLVII to form an aryl substituted biphenyl compound XLVIII. The coupling reaction may, for example, be conducted in aqueous DMF with palladium diacetate and triphenylphosphine as catalysts for the reaction. The reaction mixture may be filtered and purified by HPLC.

Exemplary compounds, provided in Examples 65-81 may be prepared from the same starting material, 2'-bromo-4-((4-methyl-1,4-diazepan-1-yl)methyl)-4'-(4-methyl-1,4-diazepane-1-carbonyl)-[1,1'-biphenyl]-2-carbonitrile, Example 61, as compound XLVI, using the aryl or heteroaryl boronic acid XLVII as indicated for the coupling reaction in accordance with Scheme X:

Example 65

4-((4-methyl-1,4-diazepan-1-yl)methyl)-4'-(4-methyl-1,4-diazepane-1-carbonyl)-[1,1':2',1''-terphenyl]-2-carbonitrile

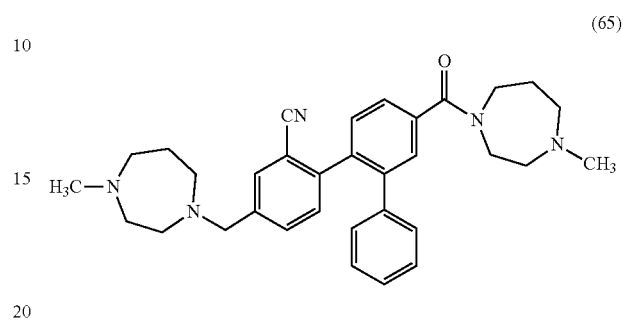

(65)

wherein the aryl or heteroaryl boronic acid XLVII was phenylboronic acid.

Example 66

4''-methoxy-4-((4-methyl-1,4-diazepan-1-yl)methyl)-4'-(4-methyl-1,4-diazepane-1-carbonyl)-[1,1':2',1''-terphenyl]-2-carbonitrile

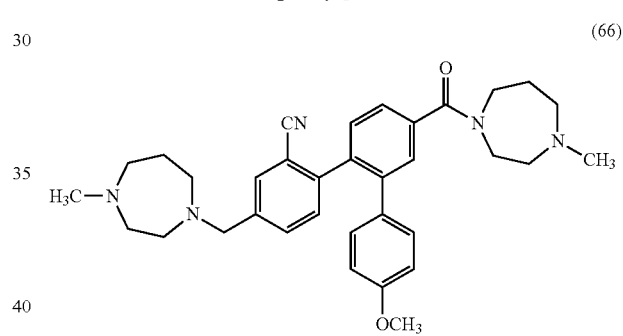

(66)

wherein the aryl or heteroaryl boronic acid XLVII was 4-methoxyphenylboronic acid.

Example 67

4''-(cyanomethyl)-4-((4-methyl-1,4-diazepan-1-yl)methyl)-4'-(4-methyl-1,4-diazepane-1-carbonyl)-[1,1':2',1''-terphenyl]-2-carbonitrile

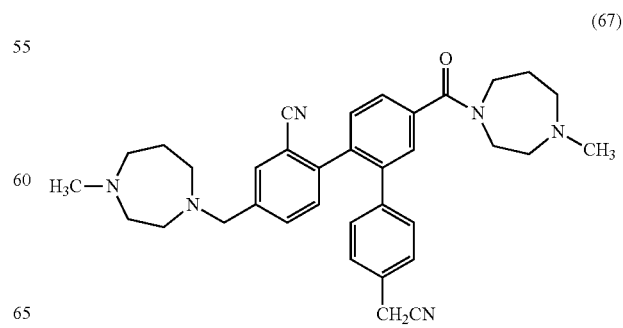

(67)

wherein the aryl or heteroaryl boronic acid XLVII was 4-(cyanomethyl)phenylboronic acid.

Example 68

4-((4-methyl-1,4-diazepan-1-yl)methyl)-4'-(4-methyl-1,4-diazepane-1-carbonyl)-[1:1':2',1''-terphenyl]-2,4''-dicarbonitrile (68)

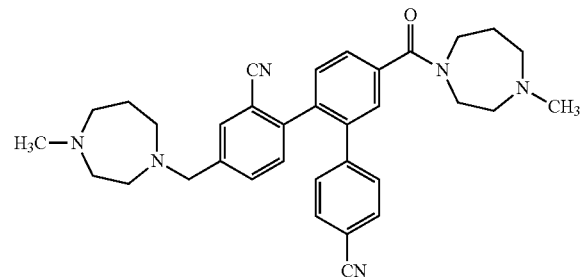

wherein the aryl or heteroaryl boronic acid XLVII was 4-cyanophenylboronic acid.

Example 69

4''-hydroxy-4-((4-methyl-1,4-diazepan-1-yl)methyl)-4'-(4-methyl-1,4-diazepane-1-carbonyl)-[1,1':2',1''-terphenyl]-2-carbonitrile (69)

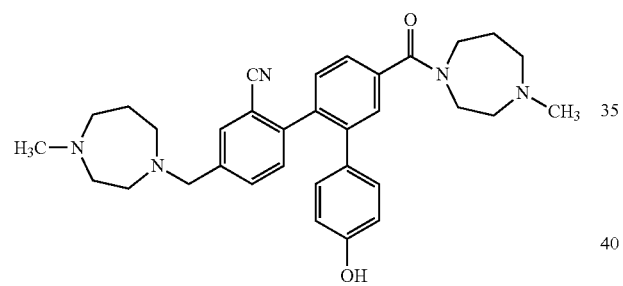

wherein the aryl or heteroaryl boronic acid XLVII was 4-hydroxyphenylboronic acid.

Example 70

4''-methyl-4-((4-methyl-1,4-diazepan-1-yl)methyl)-4'-(4-methyl-1,4-diazepane-1-carbonyl)-[1,1':2',1''-terphenyl]-2-carbonitrile (70)

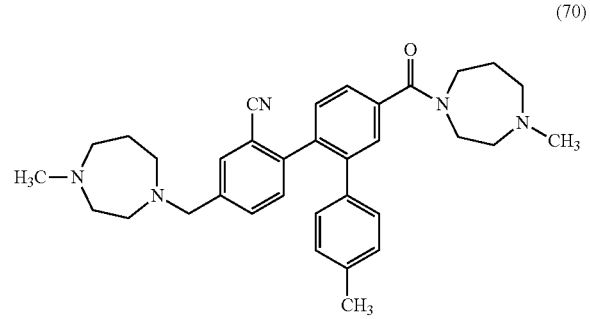

wherein the aryl or heteroaryl boronic acid XLVII was p-tolylboronic acid.

Example 71

4-((4-methyl-1,4-diazepan-1-yl)methyl)-4'-(4-methyl-1,4-diazepane-1-carbonyl)-2'-(1H-pyrazol-4-yl)-[1,1'-biphenyl]-2-carbonitrile (71)

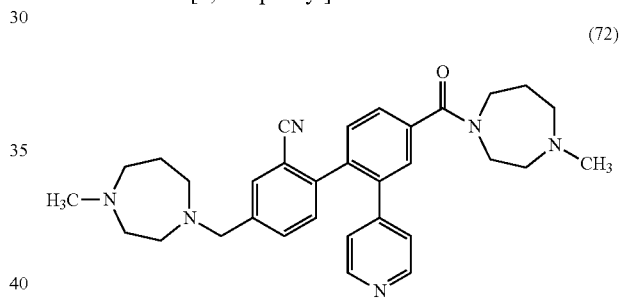

wherein the aryl or heteroaryl boronic acid XLVII was (1H-pyrazol-4-yl)boronic acid.

Example 72

4-((4-methyl-1,4-diazepan-1-yl)methyl)-4'-(4-methyl-1,4-diazepane-1-carbonyl)-2'-(pyridin-4-yl)-[1,1'-biphenyl]-2-carbonitrile (72)

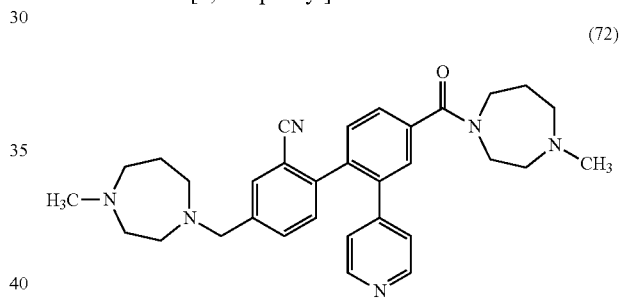

wherein the aryl or heteroaryl boronic acid XLVII was pyridine-4-ylboronic acid.

Example 73

4-((4-methyl-1,4-diazepan-1-yl)methyl)-4'-(4-methyl-1,4-diazepane-1-carbonyl)-4''-nitro-[1,1':2',1''-terphenyl]-2-carbonitrile (73)

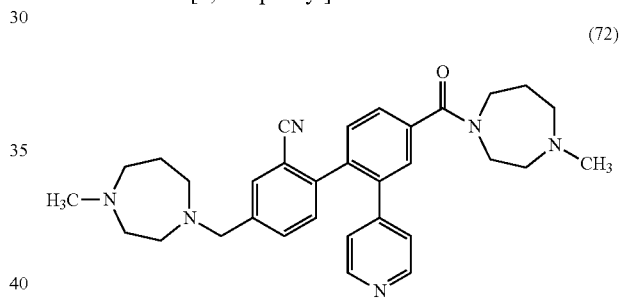

wherein the aryl or heteroaryl boronic acid XLVII was 4-nitrophenylboronic acid.

Example 74

3''-methoxy-4-((4-methyl-1,4-diazepan-1-yl)methyl)-4'-(4-methyl-1,4-diazepane-1-carbonyl)[1,1':2',1''-terphenyl]-2-carbonitrile (74)

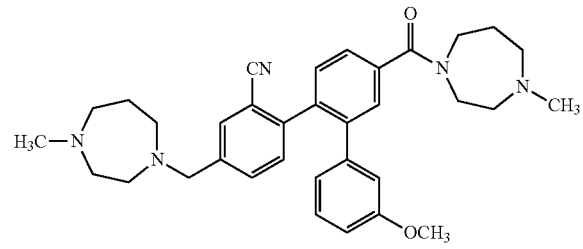

wherein the aryl or heteroaryl boronic acid XLVII was 3-methoxyphenylboronic acid.

Example 75

4-((4-methyl-1,4-diazepan-1-yl)methyl)-4'-(4-methyl-1,4-diazepane-1-carbonyl)-4''-(methylsulfonyl)-[1,1'1:2',1''-terphenyl]-2-carbonitrile (75)

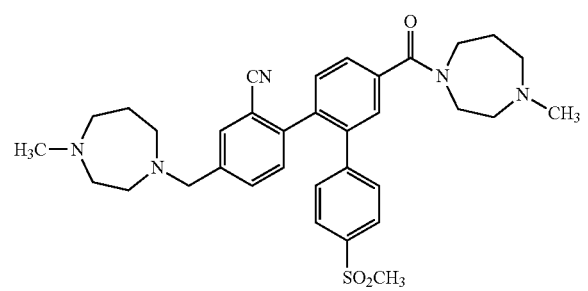

wherein the aryl or heteroaryl boronic acid XLVII was 4-(methylsulfonyl)phenylboronic acid.

Example 76

2''-cyano-N,N-dimethyl-4''-((4-methyl-1,4-diazepan-1-yl)methyl)-5-(4-methyl-1,4-diazepane-1-carbonyl)-[1,1':2',1''-terphenyl]-4-carboxamide (76)

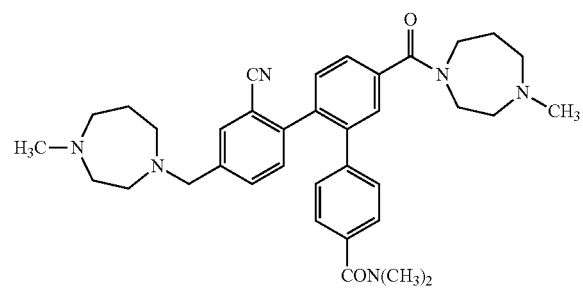

wherein the aryl or heteroaryl boronic acid XLVII was 4-(dimethylcarbamoyl)phenylboronic acid.

Example 77

4-((4-methyl-1,4-diazepan-1-yl)methyl)-4'-(4-methyl-1,4-diazepane-1-carbonyl)-3''-nitro-[1,1':2',1''-terphenyl]-2-carbonitrile (77)

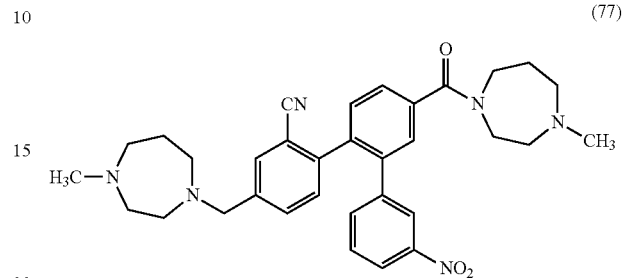

wherein the aryl or heteroaryl boronic acid XLVII was 3-nitrophenylboronic acid.

Example 78

3'',5''-difluoro-4-((4-methyl-1,4-diazepan-1-yl)methyl)-4'-(4-methyl-1,4-diazepane-1-carbonyl)-[1,1':2',1''-terphenyl]-2-carbonitrile (78)

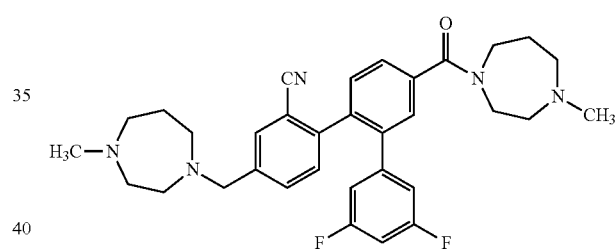

wherein the aryl or heteroaryl boronic acid XLVII was 3,5-difluorophenylboronic acid.

Example 79

4''-ethoxy-4-((4-methyl-1,4-diazepan-1-yl)methyl)-4'-(4-methyl-1,4-diazepane-1-carbonyl)-[1,1'1:2',1''-terphenyl]-2-carbonitrile (79)

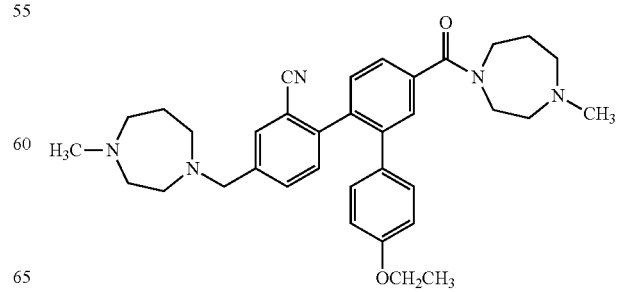

wherein the aryl or heteroaryl boronic acid XLVII was 4-ethoxyphenylboronic acid.

Example 80

4-((4-methyl-1,4-diazepan-1-yl)methyl)-4'-(4-methyl-1,4-diazepane-1-carbonyl)-4''-(morpholinomethyl)-[1,1':2',1''-terphenyl]-2-carbonitrile (80)

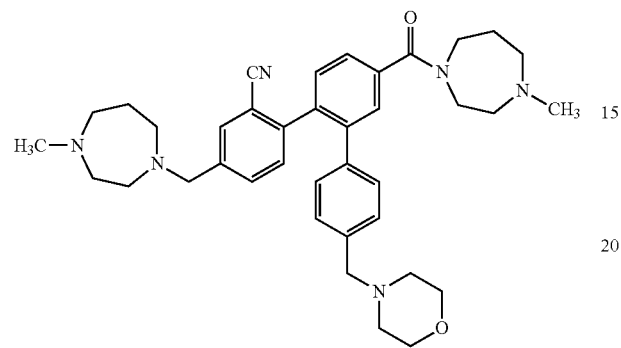

wherein the aryl or heteroaryl boronic acid XLVII was 4-(morpholinomethyl)phenylboronic acid.

Example 81

3'',4''-dimethoxy-4-((4-methyl-1,4-diazepan-1-yl)methyl)-4'-(4-methyl-1,4-diazepane-1-carbonyl)-[1,1':2',1''-terphenyl]-2-carbonitrile (81)

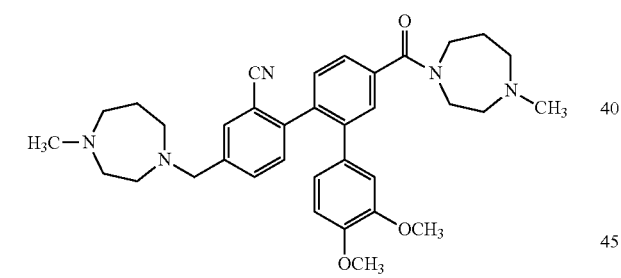

wherein the aryl or heteroaryl boronic acid XLVII was 3,4-dimethoxyphenylboronic acid.

Exemplary compounds, provided in Examples 82-127 may be prepared in accordance to Scheme XI below:

Scheme XI:

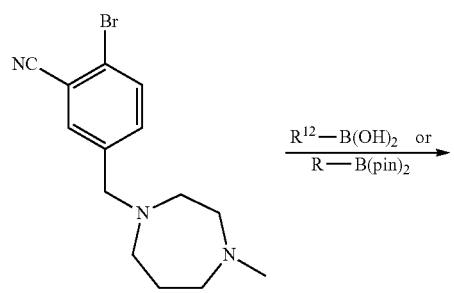

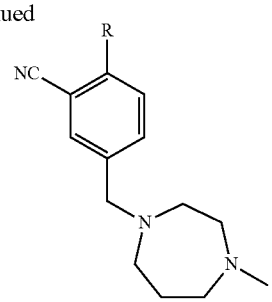

Example 82

N-(1-(2'-cyano-4'-((4-methyl-1,4-diazepan-1-yl)methyl)-[1,1'-biphenyl]-4-yl)cyclopropyl)methanesulfonamide (82)

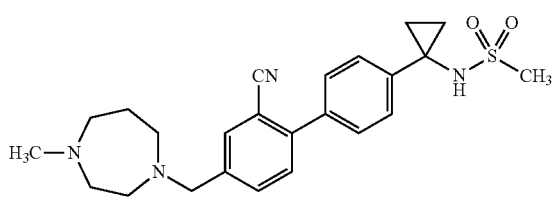

was prepared in using N-(1-(4-(4,4,5,5-tetramethyl-1,3,2-dioxaborolan-2-yl)penyl)cyclopropyl)methanesulfonamide.

Example 83

N'-acetyl-3-(2'-cyano-4'-((4-methyl-1,4-diazepan-1-yl)methyl)-[1,1'-biphenyl]-4-yl)propanehydrazide (83)

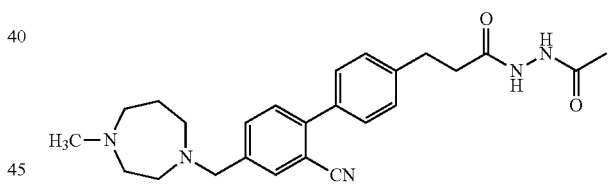

was prepared using 4-[3-(2-acetylhydrazino)-3-oxopropyl]benzeneboronic acid.

Example 84

4-((4-methyl-1,4-diazepan-1-yl)methyl)-4'-((4-methylpiperazin-1-yl)sulfonyl)-[1,1'-biphenyl]-2-carbonitrile (84)

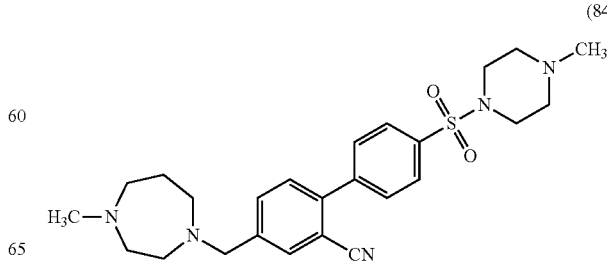

was prepared using 4-(4-methylpiperazin-1-ylsulfonyl) phenylboronic acid pinacol ester.

Example 85

2'-cyano-N-(2-hydroxyethyl)-4'-((4-methyl-1,4-diazepan-1-yl)methyl)-[1,1'-biphenyl]-4-sulfonamide

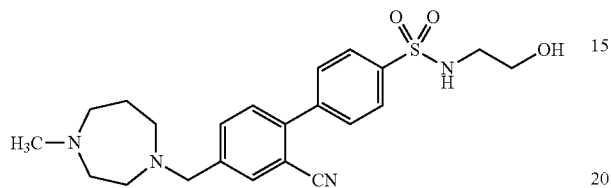

(85)

was prepared using 4-[N-(2-hydroxyethyl)sulfamoyl)benzeneboronic acid.

Example 86

2'-cyano-N-methyl-4'-((4-methyl-1,4-diazepan-1-yl)methyl)-[1,1'-biphenyl]-4-sulfonamide

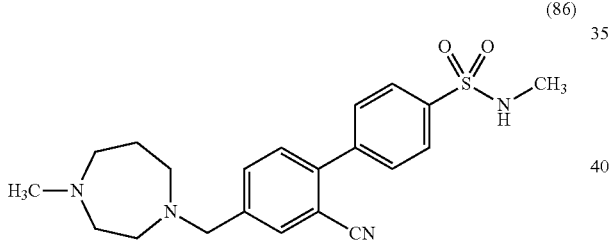

(86)

was prepared using (4-methylaminosulfonylphenyl)boronic acid.

Example 87

2'-cyano-4'-((4-methyl-1,4-diazepan-1-yl)methyl)-[1,1'-biphenyl]-4-sulfonamide

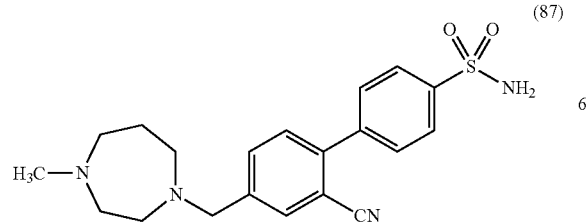

(87)

was prepared using (4-aminosulfonylphenyl)boronic acid.

Example 88

4-((4-methyl-1,4-diazepan-1-yl)methyl)-4'-(morpholinosulfonyl)-[1,1'-biphenyl]-2-carbonitrile

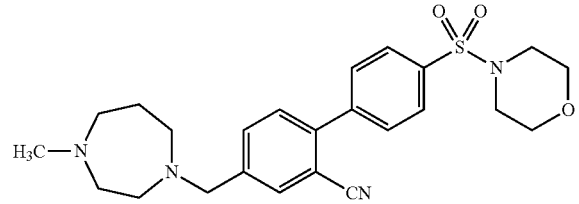

(88)

was prepared using 4-(4-morpholynylsulfonyl)phenylboronic acid.

Example 89

2-(1H-indazol-6-yl)-5-((4-methyl-1,4-diazepan-1-yl)methyl)benzonitrile

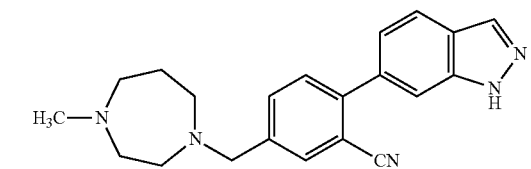

(89)

was prepared using indazole-6-boronic acid.

Example 90

1-(2'-cyano-4'-((4-methyl-1,4-diazepan-1-yl)methyl)-[1,1'-biphenyl]-4-yl)urea

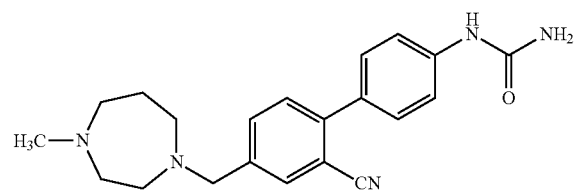

(90)

was prepared using 4-(ureido)phenylboronic acid

Example 91

2'-cyano-4'-((4-methyl-1,4-diazepan-1-yl)methyl)-[1,1'-biphenyl]-4-carbohydrazide

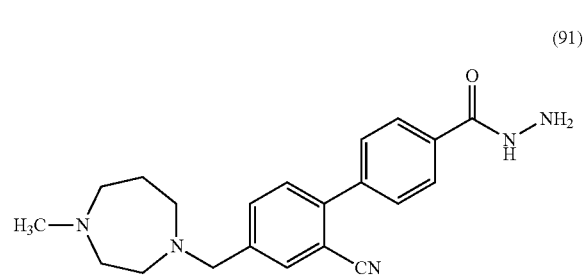 [SMILES: CN1CCCN(Cc2ccc(-c3ccc(C(=O)NN)cc3)c(C#N)c2)CC1]

(91)

was prepared using 3-fluoro-4-(hydrazinocarbonyl)benzeneboronic acid.

Example 92

2-(1H-indazol-5-yl)-5-((4-methyl-1,4-diazepan-1-yl)methyl)benzonitrile

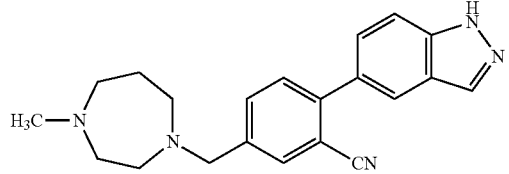
(92)

was prepared using 1H-indazole-5-boronic acid.

Example 93

4'-(cyanomethyl)-4-((4-methyl-1,4-diazepan-1-yl)methyl)-[1,1'-biphenyl]-2-carbonitrile

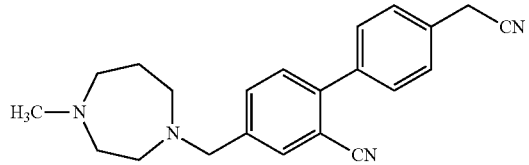
(93)

was prepared using 4-(cyanomethyl)benzeneboronic acid.

Example 94

4-((4-methyl-1,4-diazepan-1-yl)methyl)-4'-(methylsulfonyl)-[1,1'-biphenyl]-2-carbonitrile

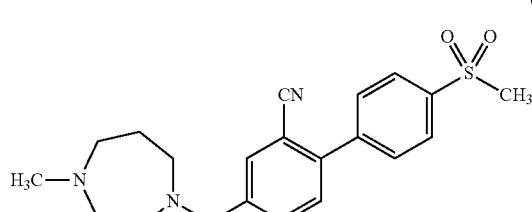
(94)

was prepared using 4-(methanesulfonyl)benzeneboronic acid.

Example 95

N-(2-(2'-cyano-4'-((4-methyl-1,4-diazepan-1-yl)methyl)-[1,1'-biphenyl]-4-yl)ethyl)acetamide

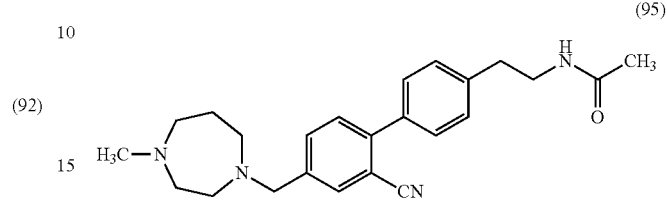
(95)

was prepared I using 4-(2-acetomidoethyl)phenylboronic acid.

Example 96

2'-cyano-2-fluoro-4'-((4-methyl-1,4-diazepan-1-yl)methyl)-[1,1'-biphenyl]-4-carboxamide (96)

was prepared using 4-carbamoyl-2-fluorobenzeneboronic acid.

Example 97

2'-cyano-N,2-dimethyl-4'-((4-methyl-1,4-diazepan-1-yl)methyl)-[1,1'-biphenyl]-4-sulfonamide (97)

was prepared using 2-methyl-4-(N-methylsulfamoyl)phenylboronic acid.

Example 98

2'-cyano-N,N,2-trimethyl-4'-((4-methyl-1,4-diazepan-1-yl)methyl)-[1,1'-biphenyl]-4-sulfonamide

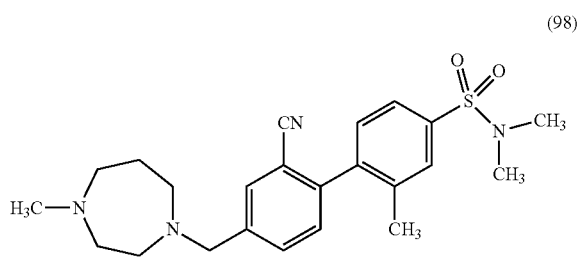

(98)

was prepared using 4-(N,N-dimethylsulfamoyl)-2-methylphenylboronic acid.

Example 99

(E)-2'-cyano-N'-hydroxy-4'-((4-methyl-1,4-diazepan-1-yl)methyl)-[1,1'-biphenyl]-4-carboximidamide

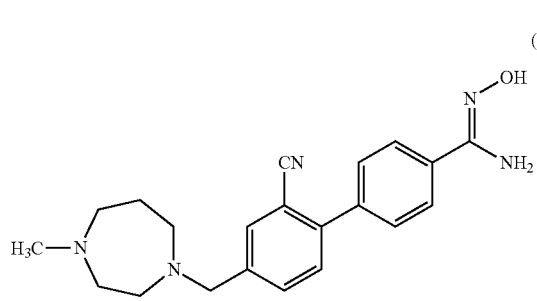

(99)

was prepared using 4-(N'-hydroxycarbamimidoyl)benzeneboronic acid.

Example 100

2-amino-3-(2'-cyano-4'-((4-methyl-1,4-diazepan-1-yl)methyl)-[1,1'-biphenyl]-4-yl)propanoic acid

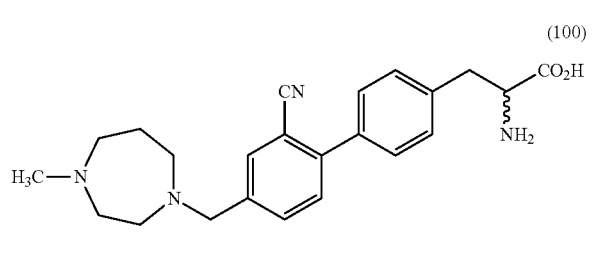 [SMILES: CN1CCCN(Cc2ccc(-c3ccc(CC(N)C(=O)O)cc3)c(C#N)c2)CC1]

(100)

was prepared using 4-borono-L-phenylalanine.

Example 101

4'-amino-4-((4-methyl-1,4-diazepan-1-yl)methyl)-3'-nitro-[1,1'-biphenyl]-2-carbonitrile

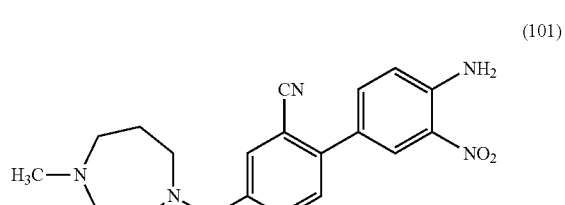

(101)

was prepared using 4-amino-3-nitrophenylboronic acid.

Example 102

N-(5-(2-cyano-4-((4-methyl-1,4-diazepan-1-yl)methyl)phenyl)pyridin-2-yl)acetamide (102)

was prepared using 2-acetomidopyridine-5-bornic acid pinacol ester.

In various embodiments, compounds 103-107 were prepared in accordance with Scheme XI using the appropriate boronic acid:

Example 103

2-(1-acetyl-1,2,3,6-tetrahydropyridin-4-yl)-5-((4-methyl-1,4-diazepan-1-yl)methyl)benzonitrile

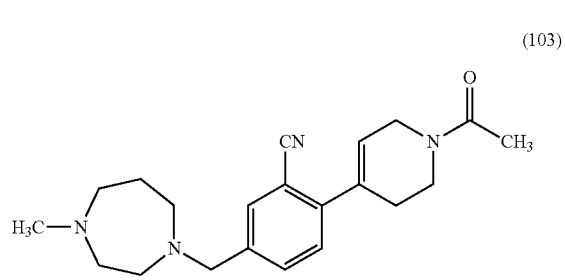 [SMILES: CC(=O)N1CC=C(c2ccc(CN3CCCN(C)CC3)cc2C#N)CC1]

(103)

Example 104

N-(2'-cyano-4'-((4-methyl-1,4-diazepan-1-yl)methyl)-[1,1'-biphenyl]-4-yl)methanesulfonamide

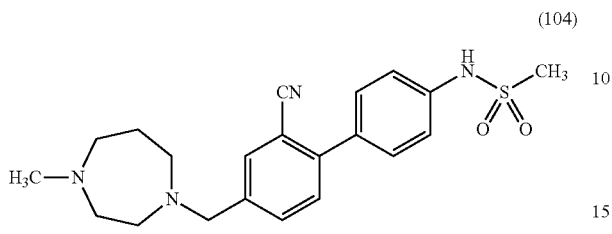
(104)

Example 105

4-((4-methyl-1,4-diazepan-1-yl)methyl)-[1,1'-biphenyl]-2,4'-dicarbonitrile

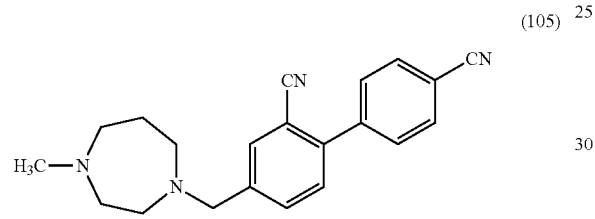
(105)

Example 106

4-((4-methyl-1,4-diazepan-1-yl)methyl)-4'-nitro-[1,1'-biphenyl]-2-carbonitrile

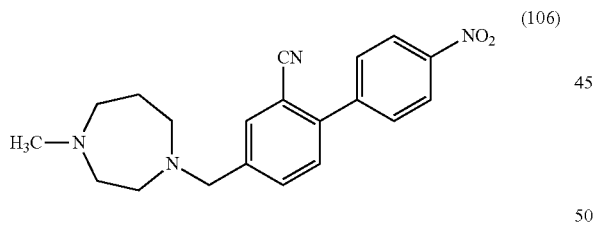
(106)

Example 107

4'-hydroxy-4-((4-methyl-1,4-diazepan-1-yl)methyl)-[1,1'-biphenyl]-2-carbonitrile

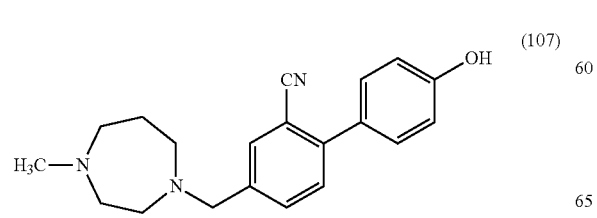
(107)

Example 108

4'-(hydroxymethyl)-4-((4-methyl-1,4-diazepan-1-yl)methyl)-[1,1'-biphenyl]-2-carbonitrile

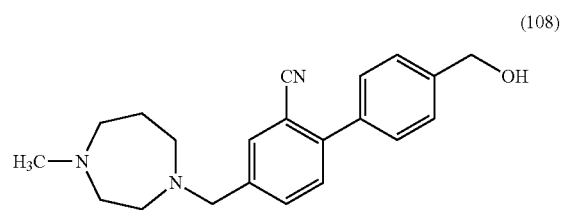 [SMILES: CN1CCCN(Cc2ccc(-c3ccc(CO)cc3)c(C#N)c2)CC1]
(108)

was prepared reduction of Example XII (Y=H) with sodium borohydride.

In various embodiments, compounds 109-115 were prepared in accordance with Scheme XI using the appropriate boronic acid:

Example 109

N-((2'-cyano-4'-((4-methyl-1,4-diazepan-1-yl)methyl)-[1,1'-biphenyl]-4-yl)sulfonyl)acetamide

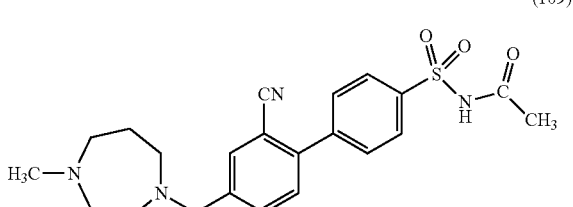
(109)

Example 110

N-(2'-cyano-4'-((4-methyl-1,4-diazepan-1-yl)methyl)-4-nitro-[1,1'-biphenyl]-3-yl)acetamide

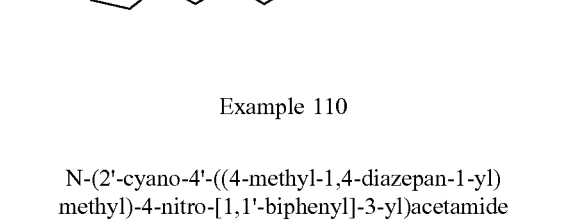
(110)

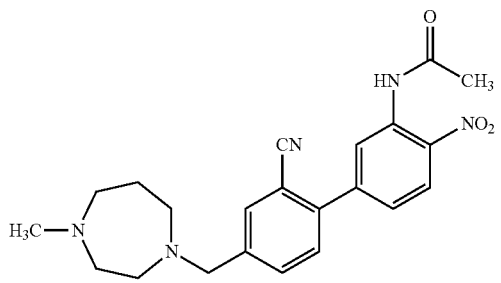

Example 111

2-(6-aminopyridin-3-yl)-5-((4-methyl-1,4-diazepan-1-yl)methyl)benzonitrile

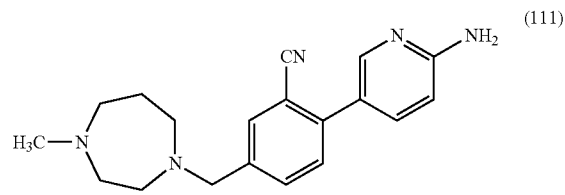 [SMILES: CN1CCCN(Cc2ccc(-c3ccc(N)nc3)c(C#N)c2)CC1]
(111)

Example 112

5-((4-methyl-1,4-diazepan-1-yl)methyl)-2-(1H-pyrazol-4-yl)benzonitrile

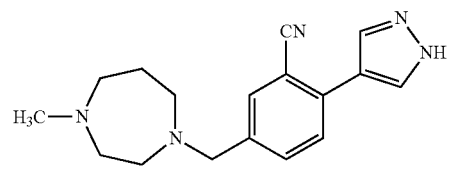
(112)

Example 113

4'-amino-4-((4-methyl-1,4-diazepan-1-yl)methyl)-[1,1'-biphenyl]-2-carbonitrile

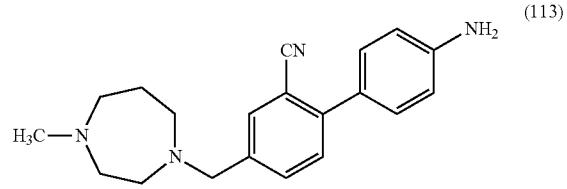 [SMILES: CN1CCCN(Cc2ccc(-c3ccc(N)cc3)c(C#N)c2)CC1]
(113)

Example 114

1-(2'-cyano-4'-((4-methyl-1,4-diazepan-1-yl)methyl)-[1,1'-biphenyl]-4-yl)-3-methylurea

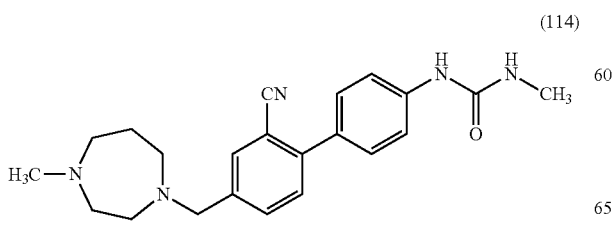
(114)

Example 115

4'-(2-aminophenoxy)-4-((4-methyl-1,4-diazepan-1-yl)methyl)-[1,1'-biphenyl]-2-carbonitrile

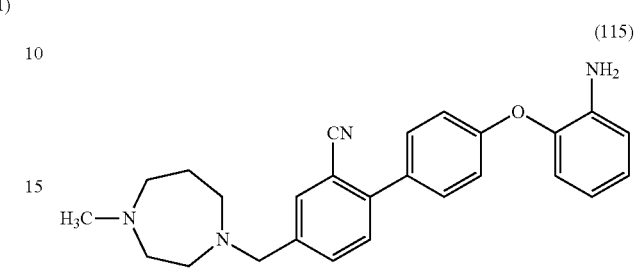
(115)

Example 116

5-(4'-((4-methyl-1,4-diazepan-1-yl)methyl)-[1,1'-biphenyl]-4-yl)-1,3,4-thiadiazol-2-amine

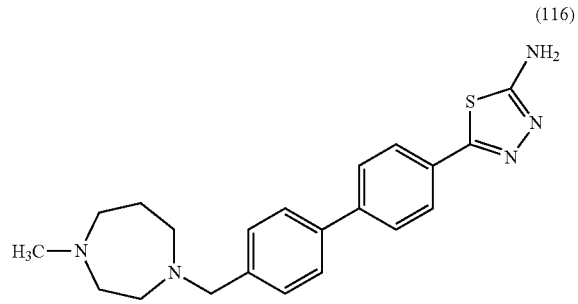 [SMILES: CN1CCCN(Cc2ccc(-c3ccc(-c4nnc(N)s4)cc3)cc2)CC1]
(116)

was prepared by a modification of Scheme XI beginning with 1-bromo-4-(4-methyl-1,4-diazepan-1-yl)methylbenzene.

In various embodiments, compounds 117-119 were prepared in accordance with Scheme XI using the appropriate boronic acid:

Example 117

5-((4-methyl-1,4-diazepan-1-yl)methyl)-2-(1H-pyrrol-3-yl)benzonitrile

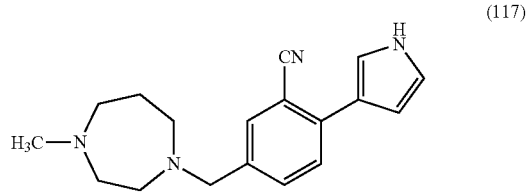 [SMILES: CN1CCCN(Cc2ccc(-c3cc[nH]c3)c(C#N)c2)CC1]
(117)

Example 118

2-(6-amino-5-methylpyridin-3-yl)-5-((4-methyl-1,4-diazepan-1-yl)methyl)benzonitrile

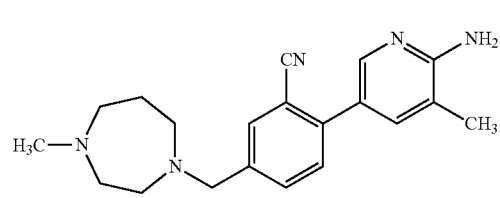
(118)

Example 119

2-(2-aminopyrimidin-5-yl)-5-((4-methyl-1,4-diazepan-1-yl)methyl)benzonitrile

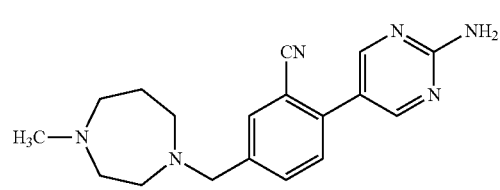
(119)

In various embodiments, compounds 120-123 were prepared as indicated or by variations of the above detailed reaction schemes in combination with standard synthetic organic reactions known in the art:

Example 120

1-(4-(5-(4-((4-methyl-1,4-diazepan-1-yl)methyl)phenyl)pyridin-2-yl)piperazin-1-yl)ethanone

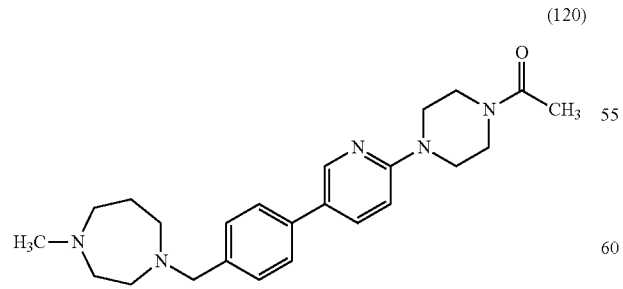
(120)

was prepared by a modification of Scheme XI beginning with 1-bromo-4-(4-methyl-1,4-diazepan-1-yl)methylbenzene.

Example 121

2'-methyl-4-((4-methyl-1,4-diazepan-1-yl)methyl)-[1,1'-biphenyl]-2,4'-dicarbonitrile

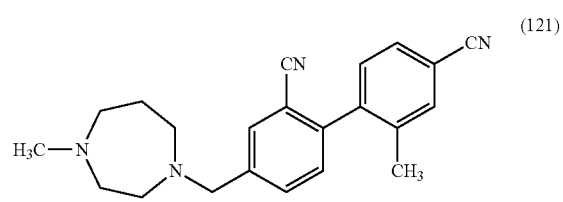 [SMILES: Cc1cc(C#N)ccc1-c1ccc(CN2CCCN(C)CC2)cc1C#N]
(121)

Example 122

N'-acetyl-3-(4'-((4-methyl-1,4-diazepan-1-yl)methyl)-[1,1'-biphenyl]-4-yl)propanehydrazide

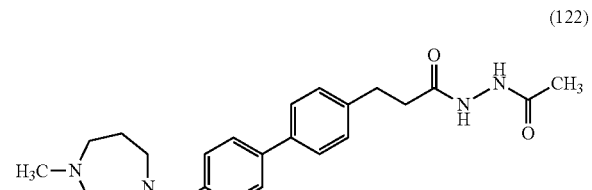
(122)

was prepared by a modification of Scheme XI beginning with 1-bromo-4-(4-methyl-1,4-diazepan-1-yl)methylbenzene.

Example 123

4'-((4-methyl-1,4-diazepan-1-yl)methyl)-3-(trifluoromethyl)-[1,1'-biphenyl]-4-carbaldehyde

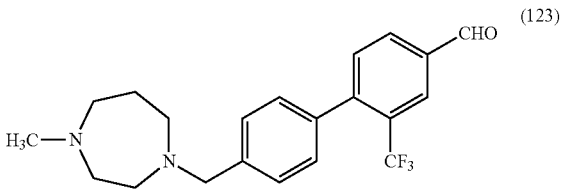 [SMILES: CN1CCCN(Cc2ccc(-c3ccc(C=O)cc3C(F)(F)F)cc2)CC1]
(123)

was prepared by a modification of Scheme XI beginning with 1-bromo-4-(4-methyl-1,4-diazepan-1-yl)methylbenzene.

In various embodiments, compounds 124-127 were prepared in accordance with Scheme XI using the appropriate boronic acid:

Example 124

2-(5-aminopyridin-3-yl)-5-((4-methyl-1,4-diazepan-1-yl)methyl)benzonitrile

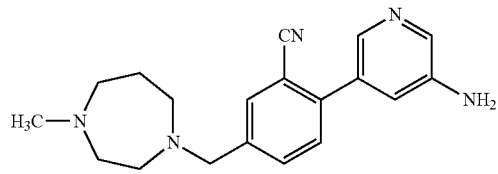

(124)

Example 125

5-((4-methyl-1,4-diazepan-1-yl)methyl)-2-(naphthalen-1-yl)benzonitrile

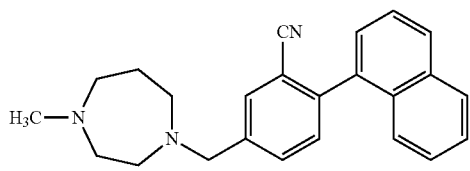

(125)

Example 126

5-((4-methyl-1,4-diazepan-1-yl)methyl)-2-(naphthalen-2-yl)benzonitrile

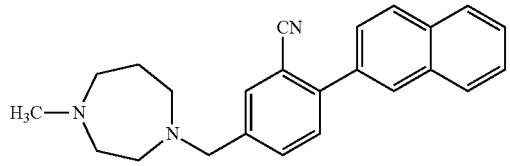

(126)

Example 127

2-(2'-cyano-4'-((4-methyl-1,4-diazepan-1-yl)methyl)-[1,1'-biphenyl]-4-yl)acetic acid

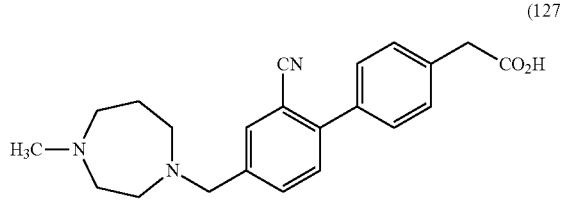

(127)

In various embodiments, compounds 128-133 were prepared in accordance with Scheme XI using the appropriate boronic acid.

Example 128

1-((4'-methoxy-[1,1'-biphenyl]-4-yl)methyl)-4-methyl-1,4-diazepane

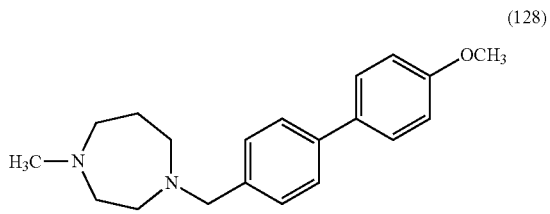 [SMILES: COc1ccc(-c2ccc(CN3CCCN(C)CC3)cc2)cc1]

(128)

Example 129

1-((4'-(1H-tetrazol-5-yl)-[1,1'-biphenyl]-4-yl)methyl)-4-methyl-1,4-diazepane

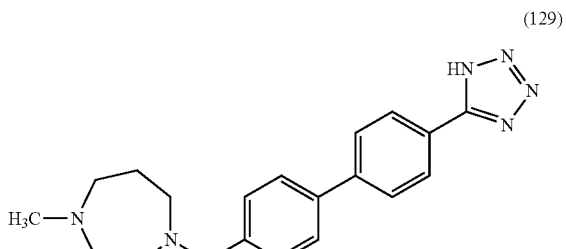

(129)

Example 130 ethyl 2-(4'-((4-methyl-1,4-diazepan-1-yl)methyl)-[1,1'-biphenyl]-4-yl)acetate

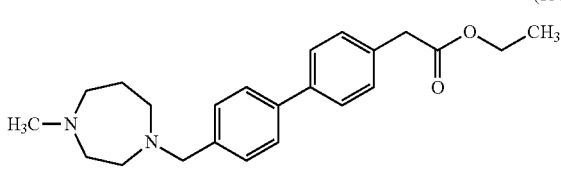

(130)

Example 131

(4'-((4-methyl-1,4-diazepan-1-yl)methyl)-4-(trifluoromethyl)-[1,1'-biphenyl]-2-yl)methanol

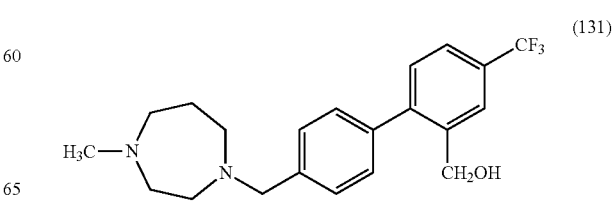

(131)

Example 132

3-(4'-((4-methyl-1,4-diazepan-1-yl)methyl)-[1,1'-biphenyl]-4-yl)propanoic acid

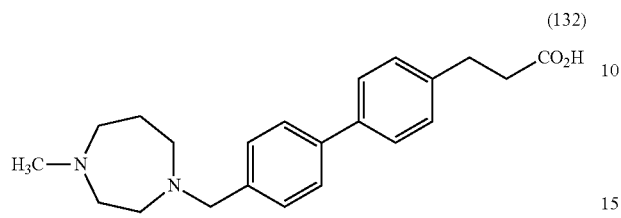

(132)

Example 133

4'-((4-methyl-1,4-diazepan-1-yl)methyl)-[1,1'-biphenyl]-2-carboxamide

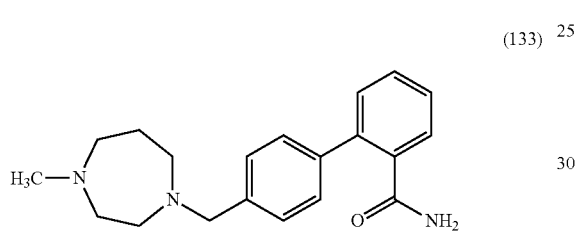

(133)

Exemplary compounds, provided in Examples 134-137 and 139-145, prepared in accordance to Scheme XII below:

Scheme XII:

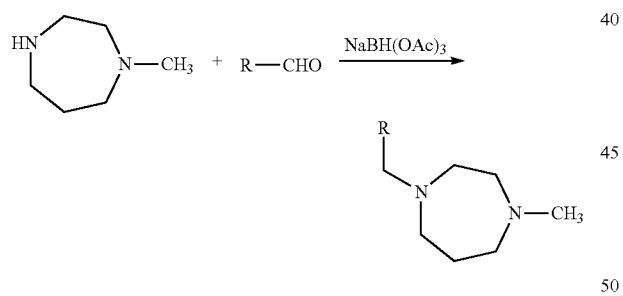

Example 134

1-((2-fluoro-[1,1'-biphenyl]-4-yl)methyl)-4-methyl-1,4-diazepane

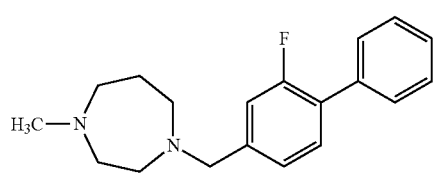

(134)

Example 135

1-((4'-fluoro-[1,1'-biphenyl]-4-yl)methyl)-4-methyl-1,4-diazepane

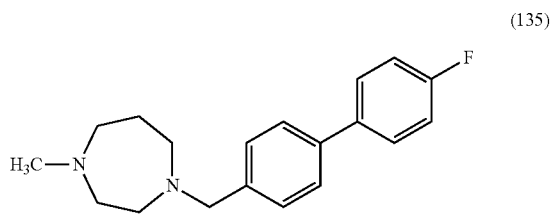 [SMILES: CN1CCCN(Cc2ccc(-c3ccc(F)cc3)cc2)CC1]

(135)

Example 136

1-methyl-4-(4-(naphthalen-1-yl)benzyl)-1,4-diazepane

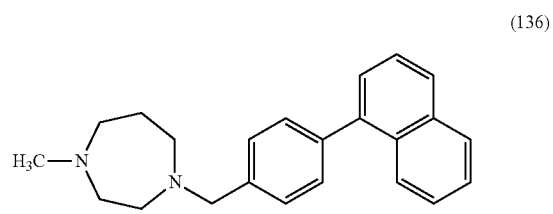 [SMILES: CN1CCCN(Cc2ccc(-c3cccc4ccccc34)cc2)CC1]

(136)

Example 137

1-methyl-4-((4'-(trifluoromethyl)-[1,1'-biphenyl]-4-yl)methyl)-1,4-diazepane

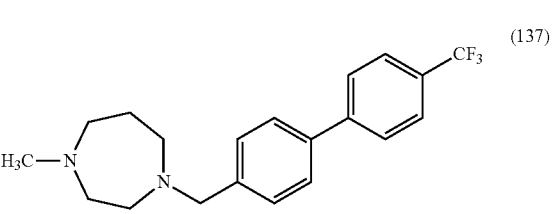 [SMILES: CN1CCCN(Cc2ccc(-c3ccc(C(F)(F)F)cc3)cc2)CC1]

(137)

Example 138

1-methyl-4-((4'-(4-methylpiperazin-1-yl)-[1,1'-biphenyl]-411)methyl)-1,4-diazepane

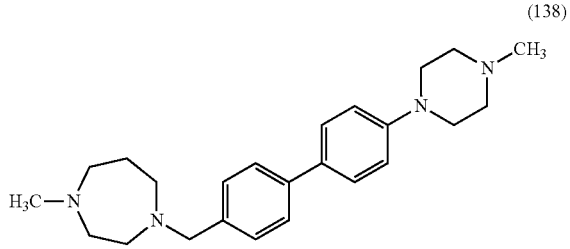

(138)

Compound 138 was prepared in accordance with Scheme XI using the appropriate boronic acid.

Example 139

1-(4-(1H-1,2,4-triazol-1-yl)benzyl)-4-methyl-1,4-diazepane

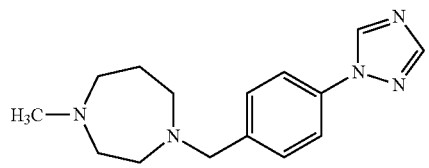
(139)

Example 140

1-methyl-4-(4-(pyridin-4-yl)benzyl)-1,4-diazepane

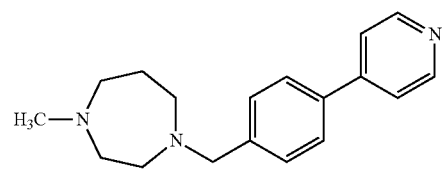
(140)

Example 141

1-methyl-4-(4-(pyridin-2-yl)benzyl)-1,4-diazepane

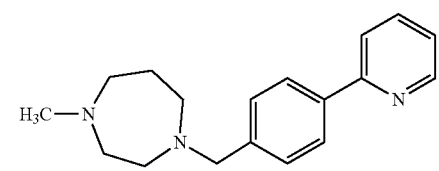
(141)

Example 142

1-(2-fluoro-4-(1H-pyrazol-1-yl)benzyl)-4-methyl-1,4-diazepane

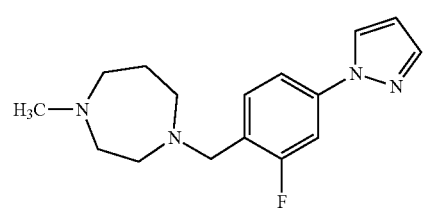
(142)

Example 143

1-(4-((1H-1,2,4-triazol-1-yl)methyl)benzyl)-4-methyl-1,4-diazepane

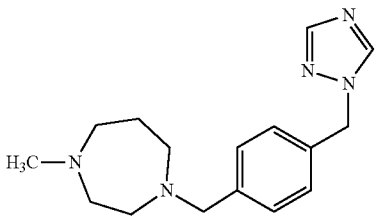
(143)

Example 144

1-(4-((4-methyl-1,4-diazepan-1-yl)methyl)phenyl)pyrrolidin-2-one

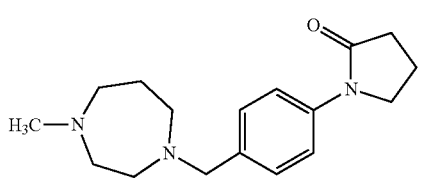
(144)

Example 145

4-(4-((4-methyl-1,4-diazepan-1-yl)methyl)phenyl)thiomorpholine 1,1-dioxide

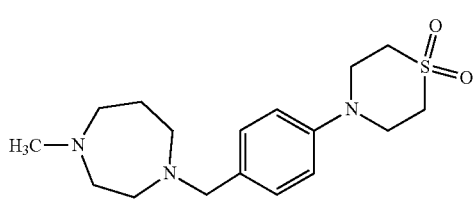
(145)

Exemplary compounds, provided in Examples 146-153, may be prepared in accordance with Scheme XIII below:

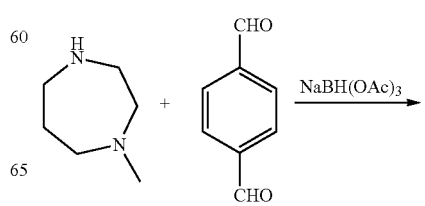

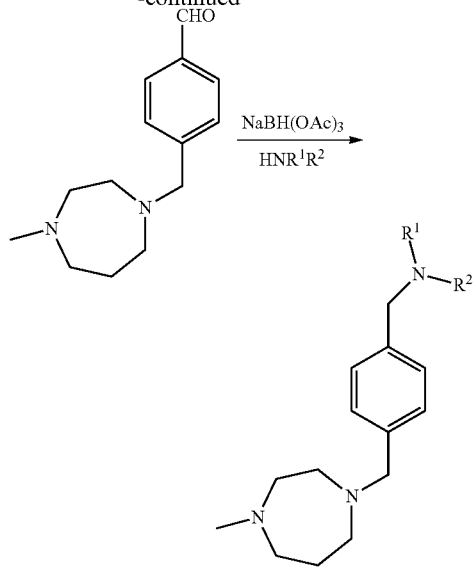

Example 146

1-(4-((4-allylpiperazin-1-yl)methyl)benzyl)-4-methyl-1,4-diazepane (146)

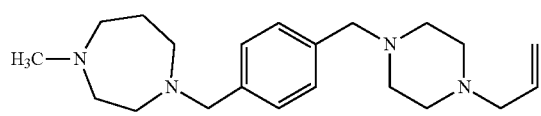

Example 147

2-(4-(4-((4-methyl-1,4-diazepan-1-yl)methyl)benzyl)piperazin-1-yl)ethanol (147)

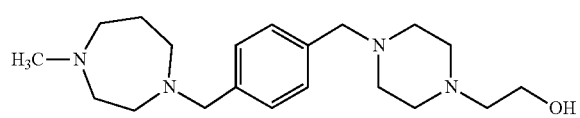

Example 148

1-methyl-4-(4-((4-(pyrrolidin-1-yl)piperidin-1-yl)methyl)benzyl)-1,4-diazepane (148)

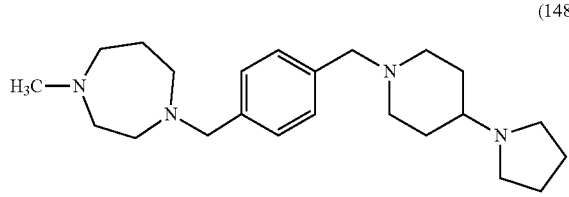

Example 149

1-methyl-4-(4-((4-(1-methylpiperidin-4-yl)piperazin-1-yl)methyl)benzyl)-1,4-diazepane (149)

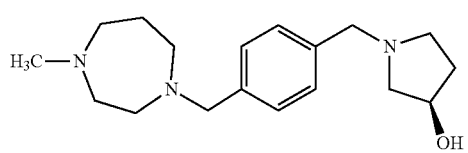

Example 150

(R)-1-(4-((4-methyl-1,4-diazepan-1-yl)methyl)benzyl)pyrrolidin-3-ol (150)

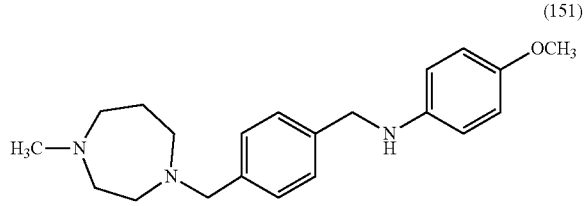 [SMILES: COc1ccc(NCc2ccc(CN3CCCN(C)CC3)cc2)cc1]

Example 151

4-methoxy-N-(4-((4-methyl-1,4-diazepan-1-yl)methyl)benzyl)aniline (151)

Example 152

3-((4-((4-methyl-1,4-diazepan-1-yl)methyl)benzyl)amino)benzamide (152)

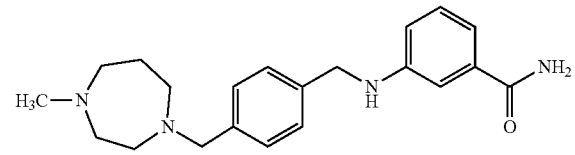

Example 153

N-(4-((4-methyl-1,4-diazepan-1-yl)methyl)benzyl)-4-(4-methylpiperazin-1-yl)aniline

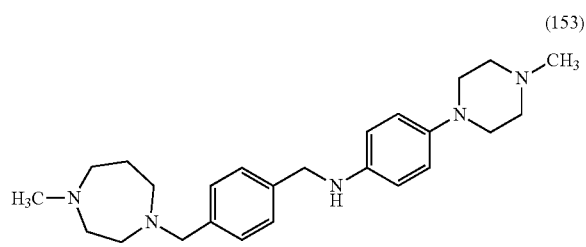

(153)

Example 154

1,4-bis(4-((4-methyl-1,4-diazepan-1-yl)methyl)phenyl)butane

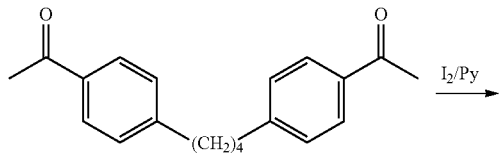

(154)

Example 154 may be prepared in accordance with the Scheme XIV below:

4,4'-Tetramethylenebis(acetophenone) was reacted with iodine to give 4,4'-Tetramethylenebis(triiodo-acetophenone), which may be hydrolyzed in sodium hydroxide to give 4,4'-(1,4-butanediyl)bisbenzoic acid. The di-acid was treated with oxalyl chloride and 1-methyl homopiperazine in sequence to give 1,4-bis(4-((4-methyl-1,4-diazepan-1-yl)carbonyl)phenyl)butane, which may be reduced with lithium aluminum hydride to give 1,4-bis(4-((4-methyl-1,4-diazepan-1-yl)methyl)phenyl)butane.

Example 155

4,4'-bis((4-methyl-1,4-diazepan-1-yl)methyl)-[1,1'-biphenyl]-3-carbonitrile

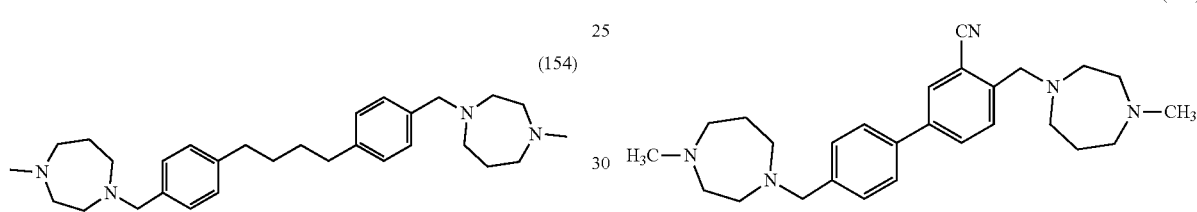

(155)

Example 155 may be prepared in accordance with the Scheme XV below:

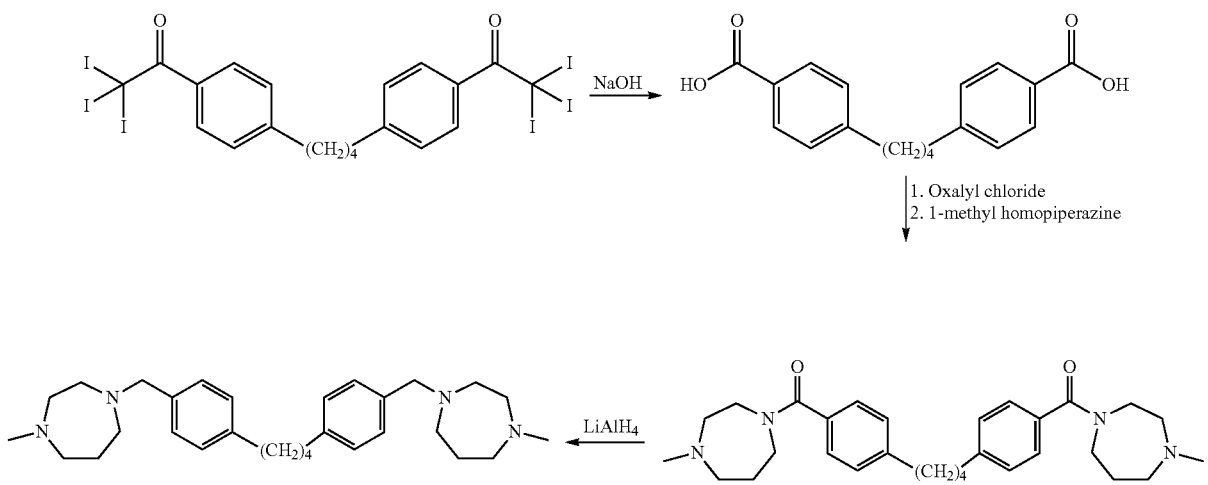

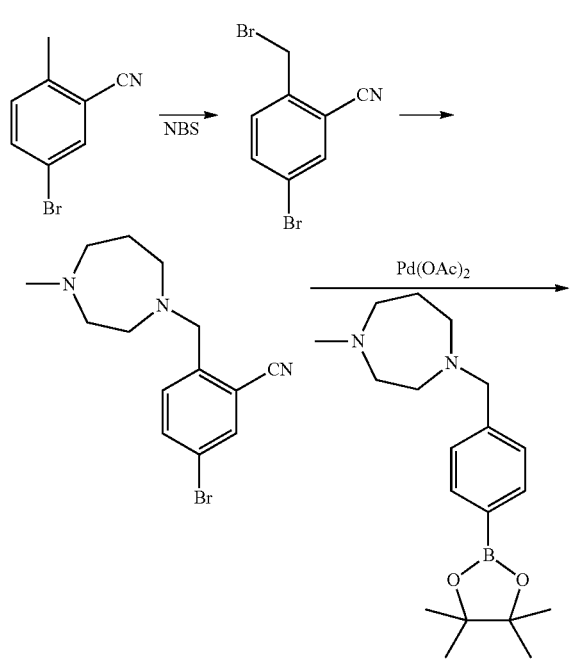

stituted benzyldiazepan XXXIV and methyl 3-bromo-4-iodobenzoate as the substituted 4-iodobenzoate ester XXXVIII, omitting any subsequent amidation or reductive amination step in accordance with a shortened variation of Scheme VIII.

Example 157

2-bromo-2'-cyano-4'-((4-methyl-1,4-diazepan-1-yl)methyl)-[1,1'-biphenyl]-4-carboxylic acid

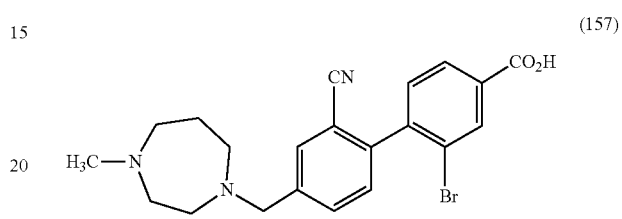

(157)

Example 157 may be prepared by alkaline hydrolysis of Example 156 discussed above.

Example 158 methyl 4'-((4-methyl-1,4-diazepan-1-yl)methyl)-[1,1'-biphenyl]-4-carboxylate

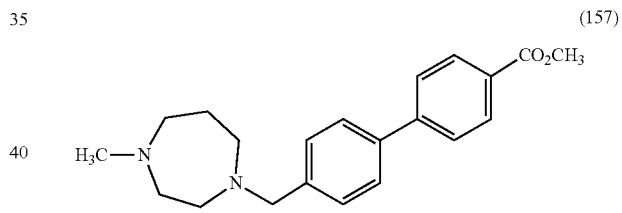

(157)

Example 158 XVII, of Scheme II, may be prepared in accordance with Scheme II by reductive amination reaction between 1-methylhomopiperazine XV and 4'-formylbiphenyl-4-carboxylic acid methyl ester XVI with sodium triethoxyborohydride and molecular sieves in DCM.

Example 159

4'-((4-methyl-1,4-diazepan-1-yl)methyl)-[1,1'-biphenyl]-4-carboxylic acid

Example 156 methyl 2-bromo-2'-cyano-4'-((4-methyl-1,4-diazepan-1-yl)methyl)-[1,1'-biphenyl]-4-carboxylate

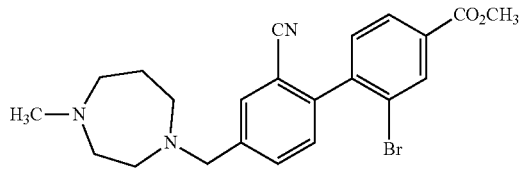

(156)

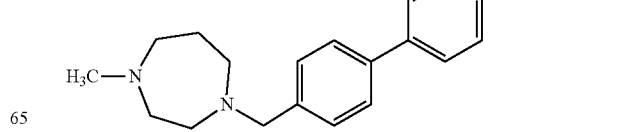

(159)

Example 156 may be synthesized by using 2-bromo-5-((4-methyl1,4-diazepan-1-yl)methyl)benzonitrile as the sub- Example 159 may be prepared by alkaline hydrolysis of Example 159 above.

Example 160

2-(4'-((4-methyl-1,4-diazepan-1-yl)methyl)-[1,1'-biphenyl]-4-yl)acetic acid

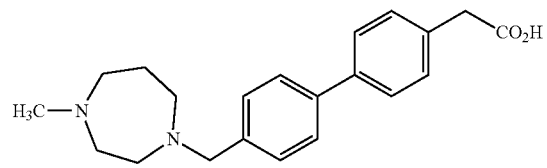

(160)

Example 160 may be prepared by alkaline hydrolysis of Example 130 above.

6. Biological Assays

This invention provides compounds having biological properties, which make them of interest for treating or ameliorating diseases in which kinases may be involved, symptoms of such disease, or the effect of other physiological events mediated by kinases. For instance, a number of compounds of this invention have been shown to inhibit choline kinase believed to mediate the growth, development and/or metastasis of cancer. A number of compounds of the invention have also been found to possess potent in vitro activity against cancer cell lines, as exemplified below.

Compounds of this invention are evaluated in a variety of assays to determine their biological activities. For example, the compounds of the invention can be tested for their ability to inhibit various protein kinases of interest, e.g. choline kinase. Some of the compounds tested displayed potent nanomolar activity against choline kinase.

The compounds can also be evaluated for their cytotoxic or growth inhibitory effects on tumor cells of interest, e.g., as described in more detail below and as shown above for some representative compounds. See e.g., WO 03/000188, pages 115-136, the full contents of which are incorporated herein by reference.

Example 161: Protein Expression

Human Choline kinase α1 (ChoKα1) that includes residues 75-457 (accession # NM_001277.2) was cloned into the pET28a expression vector (Novagene). The recombinant protein was purified via affinity, ion-exchange and size-exclusion chromatography with >95% purity.

Example 162: Kinase Assay

Enzyme inhibition measurements to obtain $IC_{50}$ values were made using a coupled a coupled (ATP regeneration) assay (Wittenberg, J. and Kornberg, A. *JBC*, 1953) with LDH/PK (5 U/4 U), choline chloride (200 μM), PEP (500 μM) and NADH (250 μM) in MOPS buffer (100 mM MOPS, pH=7, 150 mM NaCl, 10 mM $MgCl_2$, 0.1% Triton X-100). The reaction was initiated by adding 10 nM (in version 3 of the assay) of a truncated form of human Choline kinase α1 that includes residues 75-457 (accession # NM_001277.2). Version 1 of the assay utilized 200 nM of the truncated form of human Choline kinase α1 that includes residues 75-457 (accession # NM_001277.2). ΔN-ChoKα1 was cloned into the pET28a expression vector (Novagene). The recombinant protein was purified via affinity, ion-exchange and size-exclusion chromatography with >95% purity. Absorbance of NADH (340 nm) was measured over 30 min using a SpectraMax M5 (Molecular Devices). Initial reaction velocity (ΔA340/Δt) was calculated and plotted as a function of inhibitor concentration in a 2-fold dilution series. $IC_{50}$ values were obtained by fitting the relative velocities to a dose-response model. The $IC_{50}$ values are set out in TABLE 1, below.

Example 163: Cell Based Assays

Compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having antiproliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of this invention, the terms "anti-tumor" and "anti-cancer" activity are used interchangeably.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability) (e.g. using trypan blue exclusion) or measurement of DNA synthesis (e.g. by measuring incorporation of BrdU or 3H-thymidine).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

Cellular Growth Inhibition AssayVehicle or compound treated cells were assessed for cell growth after 72 hours of treatment using the CyQuant® Cell Proliferation Assay Kit (Life Technologies, Grand Island, N.Y.). To differentiate between a cytostatic and cytotoxic drug effect, the concentration that causes 50% cell growth inhibition ($GI_{50}$) was determined by correcting for the cell count at time zero (time of treatment), and plotting data as percent growth relative to vehicle-treated cells. Data are shown as mean (±SD) from ≥2 separate experiments. The GI$_{50}$ values are set out in TABLE 1, below.

Example 164: Phosphocholine Assay

5×10$^6$ cells of each line were grown in the presence of increasing concentration of the test compound or vehicle (DMSO) for 24 hours, then counted and viability checked by Trypan Blue Exclusion protocol. 5×10$^6$ viable cells were washed twice in ice cold D-PBS, then solubilized by vortexing for 30 seconds in 6 mL ice cold 100% methanol. 6 mL of chloroform and 6 mL of water were added and the mixture vortexed again. After centrifugation for 10 minutes @ 5,220 rpms, 10 mL of the aqueous phase is removed and lyophilized. The samples were analyzed by $^1$H-NMR to determine phosphocholine levels.

Dose dependent inhibition of phosphocholine levels in MDA-MB-415 cells by the compound provided in Example 55 was determined by $^1$H-NMR analysis after 24 hours of treatment with increasing concentrations consisting of 0.25 μM, 0.50 μM, 1.0 μM, 2.0 μM, 4.0 μM, 8.0 μM and 16 μM. By this method, the IC$_{50}$ of pCh was determined to be 0.75 μM of the compound provided in Example 55.

Similarly, dose dependent inhibition of phosphocholine levels in MDA-MB-468 cells by the compound provided in Example 45 was determined by $^1$H-NMR analysis after 24 hours of treatment with increasing concentrations consisting of 0.1 μM, 1.0 μM, 10 μM, 20 μM, and 80 μM. By this method, the IC$_{50}$ of pCh was determined to be 3 μM of the compound provided in Example 45.

Example 165: Binding Affinity

K$_D$ may be measured using surface plasmon resonance (BIAcore®) technology, see, e.g., Panayotou et al, *Mol. Cell. Biol.*, 13: 3567-3576 (1993)), or allied technologies (see, e.g., Malmqvist, M., *Current Opinions in Immunology* 5, 282-286; (1993); Malmqvist, M., *Nature* 361:186-187 (1993); Jonsson, U. and Malmqvist, M., *Advances in Biosensors*, JAI Press Ltd., London, 1992, pp. 291-336; Jonsson, U. et al., *Bio Techniques* 11(5):620-627 (1991)). ChoKα protein was immobilized by standard amine coupling methods on a COOH5 sensor chip installed in a SensiQ Pioneer system. Sensograms were measured using the FastStep™ screen method with an upper concentration of 500 nM. Kinetics and affinity were obtained from fits using a 1:1 binding model. As reference protein, carbonic anhydrase II at similar density was used. The binding affinity K$_D$ values are set out in TABLE 1, below.

Example 166

Mass spectrometry (MS) data, IC$_{50}$, K$_D$ and GI$_{50}$ are listed for selected compounds of the present invention in Table 1 below

TABLE 1

| Example Compound | MS | IC50 (nM) | Kd (nM) | GI50 (uM) |
|---|---|---|---|---|
| 1 | 419.2 | A | B | |
| 2 | 405.2 | A | A | |
| 3 | 462.3 | C | | |
| 4 | 419.2 | A | A | B |
| 5 | 419.3 | B | C | |
| 6 | 448.3 | B | B | |
| 7 | 418.2 | B | D | |
| 8 | 393.2 | A | A | |
| 9 | 405.2 | B | B | |
| 10 | 478.3 | C | | |
| 11 | 418.3 | B | C | |
| 12 | 363.2 | C | | |
| 13 | 403.2 | D | | |
| 14 | 432.3 | A | A | A |
| 15 | 488.3 | A | A | |
| 16 | 335.2 | B | C | |
| 17 | 407.3 | C | | |
| 18 | 462.3 | C | | |
| 19 | 433.2 | C | | |
| 20 | 377.2 | E | | |
| 21 | 476.3 | C | | |
| 22 | 433.2 | B | C | |
| 23 | 433.3 | C | | |
| 24 | 432.2 | C | | |
| 25 | 419.2 | C | | |
| 26 | 403.2 | D | | |
| 27 | 405.3 | B | C | |
| 28 | 349.2 | C | | |
| 29 | 363.2 | B | C | |
| 30 | 434.2 | A | A | |
| 31 | 431.2 | D | | |
| 32 | 389.2 | B | D | B |
| 33 | 446.3 | B | C | C |
| 34 | 417.3 | C | | |
| 35 | 393.2 | C | | |
| 36 | 419.2 | D | | |
| 37 | 421.3 | B | C | C |
| 38 | 435.2 | E | | |
| 39 | 477.3 | E | | |
| 40 | 443.3 | B | D | B |
| 41 | 443.2 | A | B | A |
| 42 | 425.3 | B | C | A |
| 43 | 441.2 | B | C | A |
| 44 | 425.3 | B | C | A |
| 45 | 407.3 | B | D | A |
| 46 | 411.2 | C | | |
| 47 | 392.2 | C | | |
| 48 | 413.2 | A | A | |
| 49 | 421.3 | C | | |
| 50 | 435.3 | B | D | A |
| 51 | 325.2 | B | D | |
| 52 | 436.3 | C | | |
| 53 | 464.3 | C | | |
| 54 | 421.3 | C | | |
| 55 | 450.3 | B | B | A |
| 56 | 457.3 | A | B | B |
| 57 | 452.3 | A | B | |
| 58 | 439.3 | C | | |
| 59 | 439.3 | D | | |
| 60 | 460.3 | D | | |
| 61 | 524.3 | C | | |
| 62 | 489.3 | C | | |
| 63 | 471.3 | B | C | |
| 64 | 461.3 | B | D | |
| 65 | 522.3 | C | | |
| 66 | 552.3 | A | A | B |
| 67 | 561.3 | C | | |
| 68 | 547.3 | C | | |
| 69 | 538.3 | A | A | |
| 70 | 536.4 | C | | |
| 71 | 512.3 | A | B | |
| 72 | 523.3 | B | C | |
| 73 | 567.3 | C | | |
| 74 | 552.3 | C | | |
| 75 | 600.2 | C | | |
| 76 | 593.3 | D | | |
| 77 | 567.3 | A | A | |
| 78 | 558.3 | A | A | |
| 79 | 566.3 | A | A | |
| 80 | 621.4 | A | A | |
| 81 | 582.3 | A | A | |
| 82 | 439.2 | A | A | B |
| 83 | 434.2 | A | A | C |

TABLE 1-continued

| Example Compound | MS IC50 (nM) | Kd (nM) | GI50 (uM) |
|---|---|---|---|
| 84 | 468.2 A | B | |
| 85 | 429.2 A | B | |
| 86 | 399.1 A | A | A |
| 87 | 584.2 A | B | C |
| 88 | 455.2 B | C | |
| 89 | 346.2 A | A | C |
| 90 | 364.2 B | C | |
| 91 | 364.2 B | C | |
| 92 | 346.2 A | A | C |
| 93 | 345.2 B | D | |
| 94 | 384.1 B | C | |
| 95 | 391.2 C | | |
| 96 | 367.1 C | | |
| 97 | 413.2 B | C | |
| 98 | 427.2 C | | |
| 99 | 364.2 C | | |
| 100 | 393.2 C | | |
| 101 | 366.1 C | | |
| 102 | 364.2 C | | |
| 103 | 353.2 C | | |
| 104 | 399.2 A | A | C |
| 105 | 331.2 C | | |
| 106 | 351.1 C | | |
| 107 | 322.1 C | | |
| 108 | 336.2 C | | |
| 109 | 427.1 C | | |
| 110 | 408.2 C | | |
| 111 | 322.2 C | | |
| 112 | 296.2 C | | |
| 113 | 321.2 D | | |
| 114 | 378.2 A | B | |
| 115 | 413.2 D | | |
| 116 | 380.1 D | | |
| 117 | 295.2 D | | |
| 118 | 336.2 D | | |
| 119 | 323.2 D | | |
| 120 | 408.2 D | | |
| 121 | 345.2 D | | |
| 122 | 409.2 D | | |
| 123 | 377.1 D | | |
| 124 | 322.2 E | | |
| 125 | 356.2 E | | |
| 126 | 356.2 E | | |
| 127 | 364.2 E | | |
| 128 | 311.2 B | D | |
| 129 | 349.2 E | | |
| 130 | 367.2 E | | |
| 131 | 379.1 E | | |
| 132 | 353.2 E | | |
| 133 | 324.2 E | | |
| 155 | 432.3 C | | |
| 156 | 442.1 D | | |
| 157 | 428.1 E | | |
| 158 | 339.2 B | D | |
| 134* | 299.2 B | D | |
| 135* | 299.2 E | | |
| 136* | 331.2 E | | |
| 137* | 349.1 B | D | |
| 138* | 379.2 B | D | |
| 139* | 272.2 C | D | |
| 140* | 282.2 B | D | |
| 141* | 282.2 E | | |
| 142* | 289.2 B | D | |
| 143* | 286.2 E | | |
| 144* | 288.2 E | | |
| 145* | 338.1 E | | |
| 146* | 343.3 E | | |
| 147* | 347.2 E | | |
| 148* | 371.3 B | D | |
| 149* | 400.3 E | | |
| 150* | 304.2 E | | |
| 151* | 340.2 E | | |
| 152* | 353.2 B | D | |
| 153* | 408.3 B | D | |
| 154* | 463.7 E | | |
| 159* | 325.1 E | | |
| 160* | 339.2 E | | |

TABLE 1-continued

| Example Compound | MS IC50 (nM) | Kd (nM) | GI50 (uM) |
|---|---|---|---|
| | Grouping IC50: | Grouping Kd | Grouping GI50 |
| | A is <100 nM | A is <50 | A is <5 |
| | B is <200 nM | B is <100 | B is <20 |
| | C is <500 nm | C is <200 | C is >20 |
| | D is <2000 nM | D is <60000 | |
| | E is <=50000 nM | | |

*IC50 data shown is from version 1 of the Kinase Assay as described herein. IC50 data for Examples not designated with an asterisk (*) is from version 1 of the Kinase Assay.

References to other documents, such as patents, patent applications, journals, books, etc., have been made throughout this disclosure. All such documents are hereby incorporated herein by reference in their entirety for all purposes.

It is to be understood that the foregoing description is exemplary and explanatory in nature, and is intended to illustrate the presently disclosed general inventive concept and its preferred embodiments. Through routine experimentation, those of skill in the art given the benefit of the present disclosure may recognize apparent modifications and variations without departing from the spirit and scope of the present disclosure. Thus, the present disclosure is not limited by the above description, but rather by the following claims and their equivalents.

What is claimed is:

1. A compound selected from:

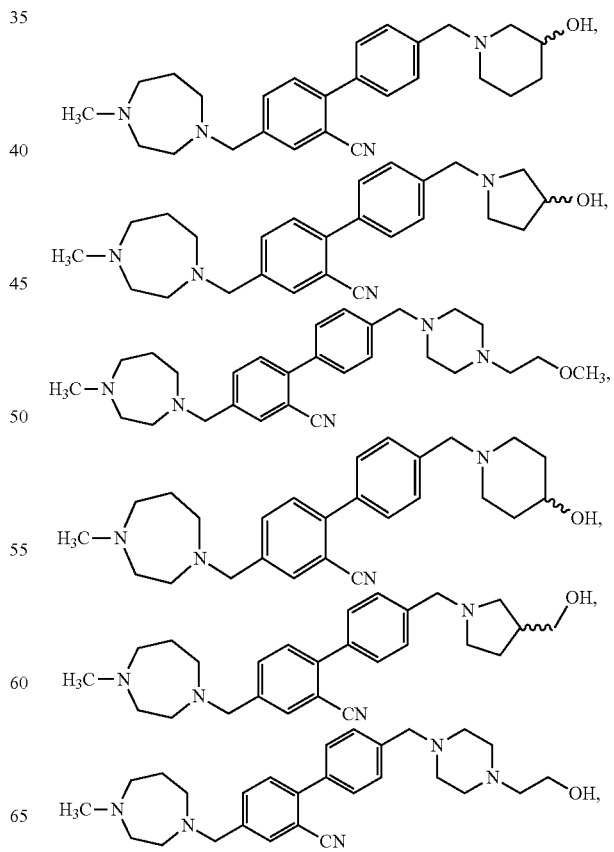

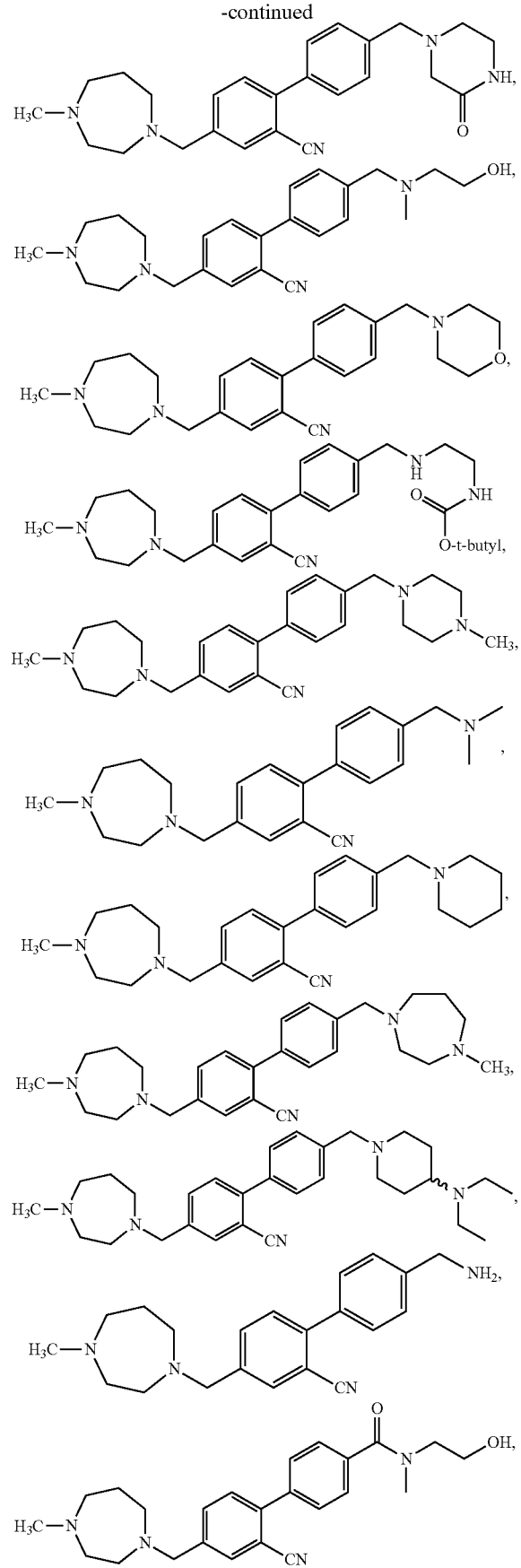
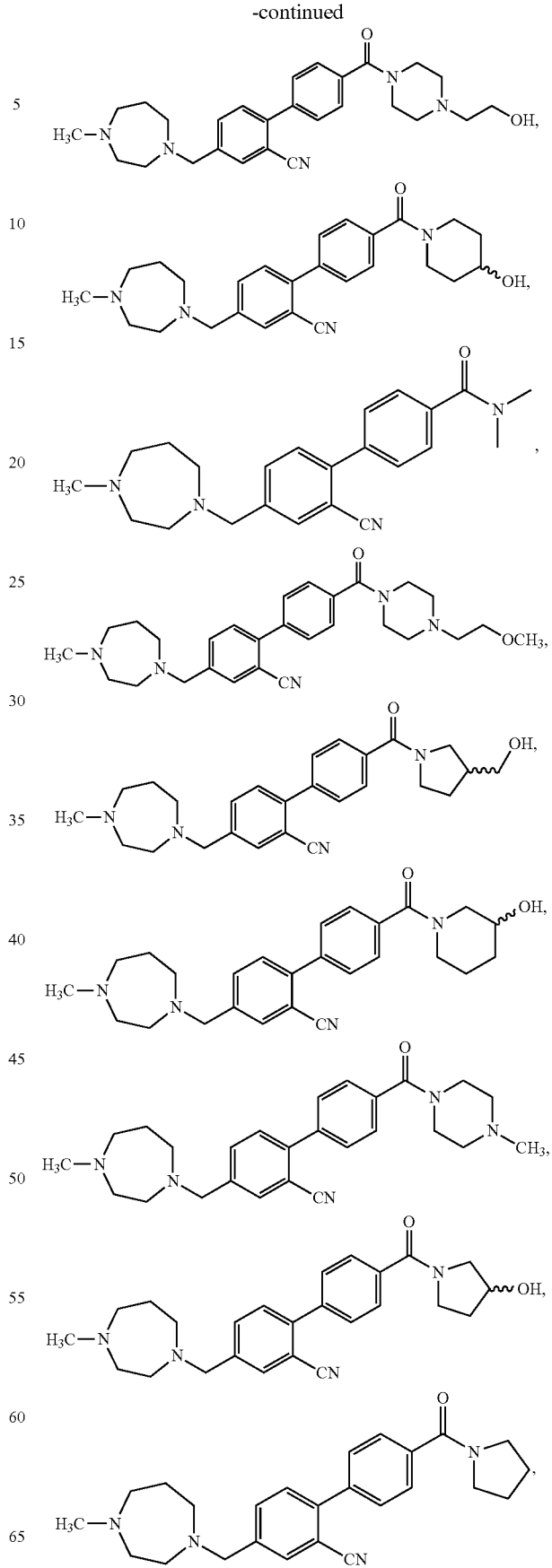

123
-continued
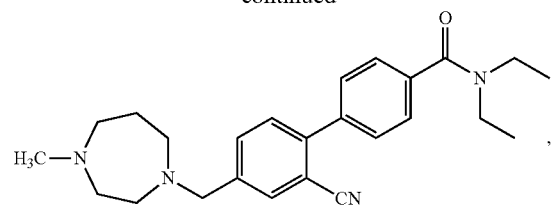
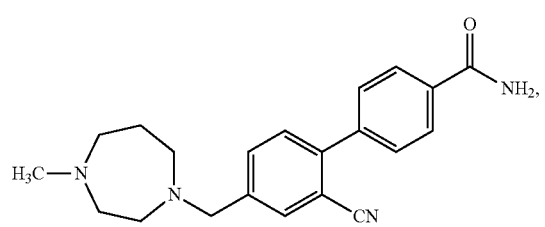
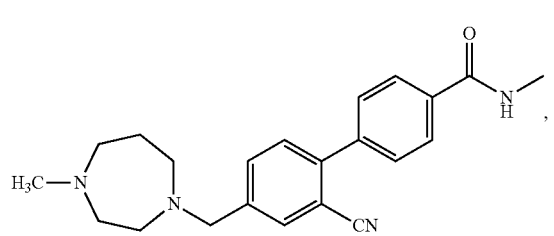
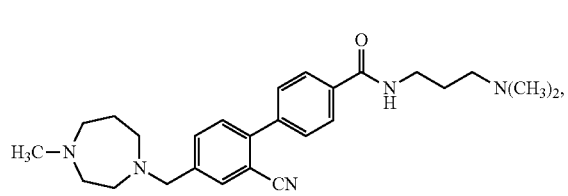
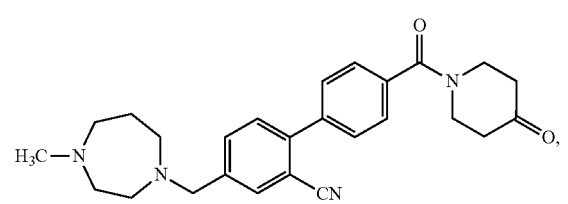
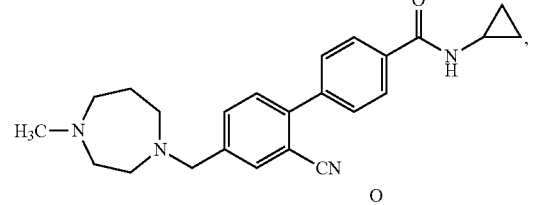
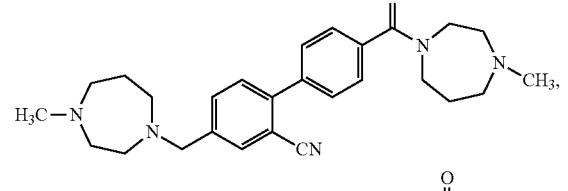
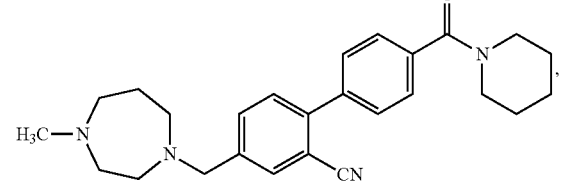
124
-continued
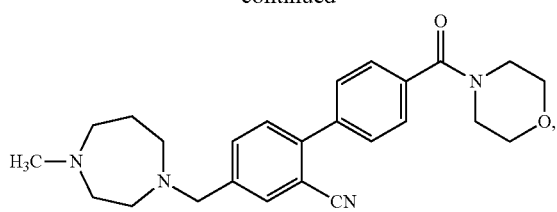
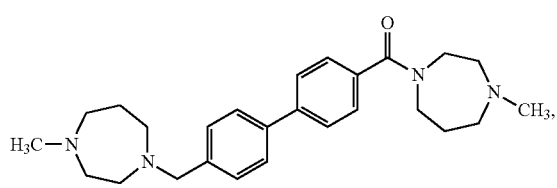
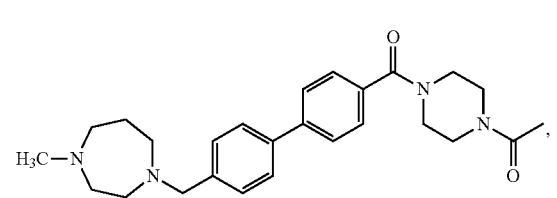
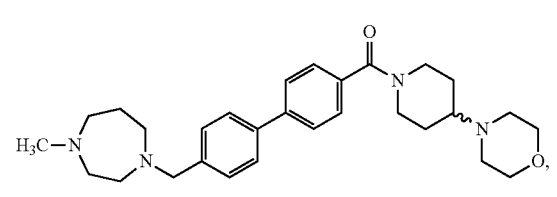
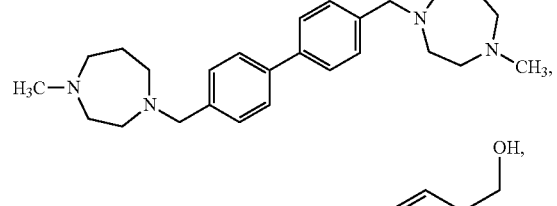
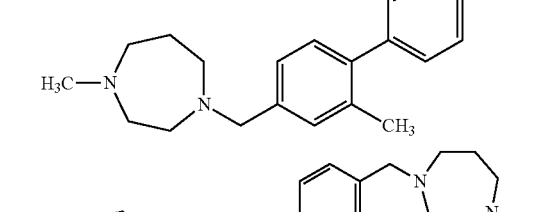
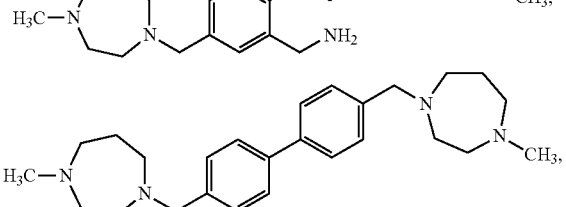
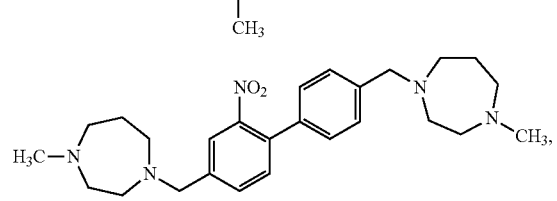

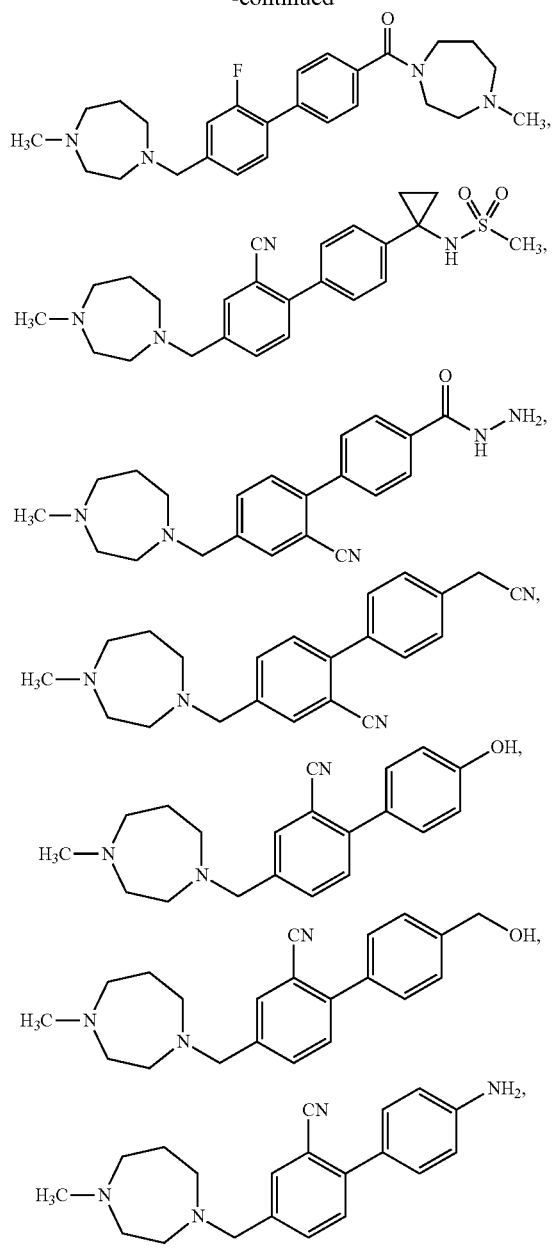
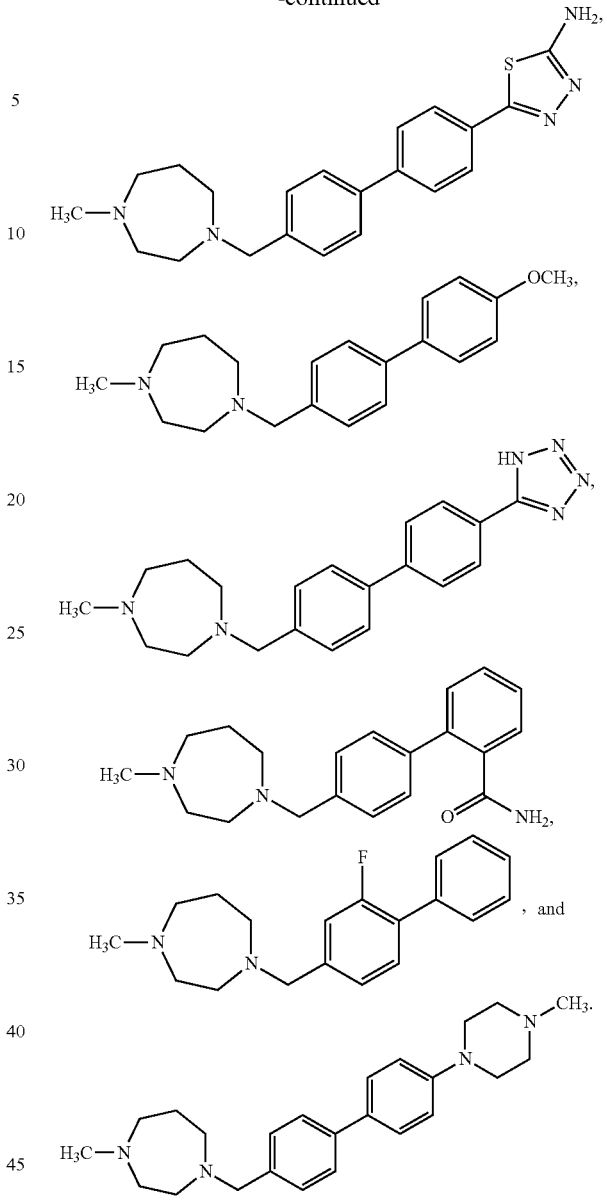

UNITED STATES PATENT AND TRADEMARK OFFICE
CERTIFICATE OF CORRECTION

PATENT NO. : 9,834,521 B2  
APPLICATION NO. : 14/774359  
DATED : December 5, 2017  
INVENTOR(S) : Zech et al.

Page 1 of 1

It is certified that error appears in the above-identified patent and that said Letters Patent is hereby corrected as shown below:

On the Title Page

Change the title to read as follows:
- NOVEL CHOLINE KINASE INHIBITORS -

Signed and Sealed this
Twenty-fourth Day of July, 2018

Andrei Iancu
*Director of the United States Patent and Trademark Office*